US012721907B2

(12) United States Patent
Taratula et al.

(10) Patent No.: US 12,721,907 B2
(45) Date of Patent: Sep. 1, 2026

(54) COBALT-DOPED IRON OXIDE NANOPARTICLES AND METHODS FOR MAKING AND USING

(71) Applicants: Oregon State University, Corvallis, OR (US); Oregon Health & Science University, Portland, OR (US)

(72) Inventors: Olena Taratula, Corvallis, OR (US); Oleh Taratula, Corvallis, OR (US); Ananiya A. Demessie, Corvallis, OR (US); Ov Slayden, Portland, OR (US); Youngrong Park, Corvallis, OR (US)

(73) Assignees: Oregon State University, Corvallis, OR (US); Oregon Health & Science University, Portland, OR (US)

( * ) Notice: Subject to any disclaimer, the term of this patent is extended or adjusted under 35 U.S.C. 154(b) by 728 days.

(21) Appl. No.: 18/186,606

(22) Filed: Mar. 20, 2023

(65) Prior Publication Data

US 2023/0338575 A1 Oct. 26, 2023

Related U.S. Application Data

(60) Provisional application No. 63/322,038, filed on Mar. 21, 2022.

(51) Int. Cl.

| | |
|---|---|
| ***A61K 47/69*** | (2017.01) |
| ***A61K 33/26*** | (2006.01) |
| ***A61K 47/64*** | (2017.01) |
| ***B82Y 5/00*** | (2011.01) |
| ***B82Y 30/00*** | (2011.01) |

(52) U.S. Cl.
CPC .......... *A61K 47/6935* (2017.08); *A61K 33/26* (2013.01); *A61K 47/6425* (2017.08); *B82Y 5/00* (2013.01); *B82Y 30/00* (2013.01)

(58) Field of Classification Search
CPC ................ A61K 47/6935; A61K 33/26; A61K 47/6425; A61K 41/0052; A61K 47/62; A61K 49/14; A61K 49/1857; A61K 49/186; A61K 49/1866; B82Y 5/00; B82Y 30/00
See application file for complete search history.

(56) References Cited

PUBLICATIONS

Hou et al., Deformable Block Copolymer Microparticles by Controllable Localization of pH-Responsive Nanoparticles, Macromolecules 2020, vol. 53, Iss. 1, pp. 473-481 (Year: 2020).*
Li et al. LHRH-Targeted Drug Delivery Systems for Cancer Therapy. Mini Rev Med Chem. 2017;17(3):258-267 (Year: 2017).*
Lukasiewicz et al. Polycaprolactone Nanoparticles as Promising Candidates for Nanocarriers in Novel Nanomedicines. Pharmaceutics. Feb. 1, 2021;13(2):191 (Year: 2021).*
Moses et al. Nanomedicines for Endometriosis: Lessons Learned from Cancer Research. Small. Feb. 2021;17(7) (Year: 2021).*
El-Shahawy et al. Bimodal Approach for the Use of Co Doped Magnetite as MRI Contrat Agent and Potential Antitumor, Journal of Magnetics 25(4), 540-546 (2020) (Year: 2020).*
Fantechi et al. Influence of cobalt doping on the hyperthermic efficiency of magnetite nanoparticles, Journal of Magnetism and Magnetic Materials, vol. 380, 2015, pp. 365-371 (Year: 2015).*
Lee et al. Exchange-coupled magnetic nanoparticles for efficient heat induction. Nature Nanotech 6, 418â422 (2011) (Year: 2011).*
Revia et al. Magnetite nanoparticles for cancer diagnosis, treatment, and treatment monitoring: recent advances, Materials Today, vol. 19, Iss. 3, 2016, pp. 157-168 (Year: 2016).*
Surendra et al. Realization of highest specific absorption rate near superparamagnetic limit of CoFe2O4 colloids for magnetic hyperthermia applications, 2014 Mater. Res. Express , vol. 1, No. 2, 026107 (Year: 2014).*
Venkatesan et al. Structural and magnetic properties of cobalt-doped iron oxide nanoparticles prepared by solution combustion method for biomedical applications. Int J Nanomedicine. 2015;10(Supplement 1 Challenges in biomaterials research):189-198 (Year: 2015).*
Demessie et al., "An Advanced Thermal Decomposition Method to Produce Magnetic Nanoparticles with Ultrahigh Heating Efficiency for Systemic Magnetic Hyperthermia," *Small Methods* 6(12):e2200916, 2022 (12 pages).
Albarqi et al., "Biocompatible Nanocluster with High Heating Efficiency for Systemically Delivered Magnetic Hyperthermia," *ACS Nano* 13:6383-6395, 2019 published online May 13, 2019.
Albarqi, "Systemically Delivered Magnetic Hyperthermia for Cancer Treatment," *An Abstract of the Thesis of Assan Ahmad M. Albarqi* (133 pages), Jun. 12, 2019.
Albarqi et al., "Systemically Delivered Magnetic Hypertherrnia for Prostate Cancer Treatment," *Pharmaceutics* 12(1020) (14 pages), 2020, published online Oct. 25, 2020.
Han et al., "Applications of nanoparticles in biomedical imaging," *Nanoscale* 11:799-819, 2019, published online Dec. 24, 2018.
Lee et al., "Ultrasmall superparamagnetic iron oxides enhanced MR imaging in rats with experimentally induced endometriosis," *Magnetic Resonance Imaging* 30(6):860-868, Jul. 2012.
Moses et al., "Nanomedicines for Endometriosis: Lessons Learned from Cancer Research," *Small* 17(2004975 (28 pages), 2021, published online Jan. 25, 2021.
Taratula et al., "Abstract 2875: Intravascular delivery of nanoclusters for treatment of prostate cancer with magnetic hyperthermia," *Poster Presentations—Proffered Abstracts* Aug. 15, 2020; *Cancer Research* 80(16_Supplemental):2875, 2020 (4 pages).
Zhang et al., "Hyaluronic Acid-Modified Magnetic Iron Oxide Nanoparticles for MR Imaging of Surgically Induced Endometriosis Model in Rats," *PLoS One* 9(4):e94718 (6 pages), Apr. 10, 2014.

* cited by examiner

*Primary Examiner* — Joanne Hama
*Assistant Examiner* — Emmanuel Led Youtchom Pendie
(74) *Attorney, Agent, or Firm* — Klarquist Sparkman, LLP

(57) ABSTRACT

Disclosed herein are embodiments of a nanoparticle suitable for use in providing hyperthermia treatment. The nanoparticle may be a cobalt-doped iron oxide nanoparticle. Also disclosed are compositions comprising the nanoparticle. The composition may further comprise a polymer and/or a targeting moiety. Further disclosed and methods for making the nanoparticle and the composition, and embodiments of a method for using the nanoparticle or a composition thereof. The nanoparticle may be useful for treating cancer, and/or endometriosis.

20 Claims, 38 Drawing Sheets

Specification includes a Sequence Listing.

50 ml/min 14 nm

Before
AMF
23 days
32 days 21.6 ± 2.05
0
5
10
15
20
25
14
16
18
20
22
24
26
28
Size (nm)
FIG. 45
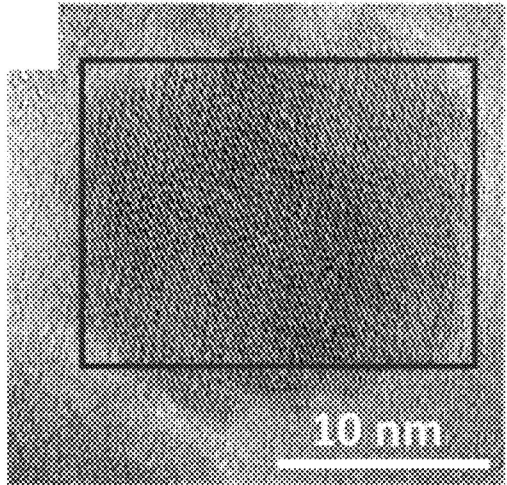
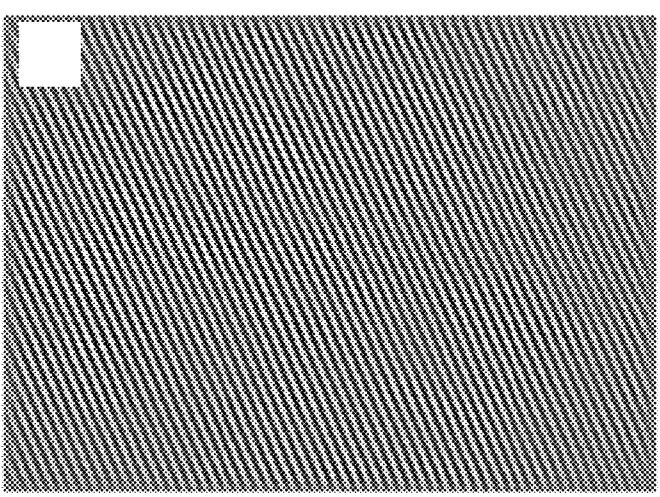
FIG. 46

COBALT-DOPED IRON OXIDE NANOPARTICLES AND METHODS FOR MAKING AND USING

CROSS REFERENCE TO RELATED APPLICATION

This application claims the benefit of the earlier filing date of U.S. Provisional Application No. 63/322,038, filed on Mar. 21, 2022, which is incorporated herein by reference in its entirety.

ACKNOWLEDGMENT OF GOVERNMENT SUPPORT

This invention was made with government support under Awards 1R15EB020351-01A1, 1R01CA237569-01A1 and R21HD098642 awarded by National Institutes of Health. The government has certain rights in the invention.

FIELD

The field of this disclosure generally relates to nanoparticles and compositions thereof, methods of making the nanoparticles and compositions, and methods of using the nanoparticles and compositions in certain medical applications, such as medical hyperthermia treatment.

REFERENCE TO AN ELECTRONIC SEQUENCE LISTING

The contents of the electronic sequence listing ("Sequence.xml", created on May 11, 2023, 12,288 bytes) is herein incorporated by reference in its entirety.

BACKGROUND

Magnetic hyperthermia mediated by iron oxide nanoparticles (IONPs) has attracted much attention for cancer therapy. It may also be used for other lesions considered non-cancerous, for example, endometriosis. It is a novel approach for minimally invasive treatment with heat produced under tissue-penetrating magnetic field. The rationale for this treatment is that tumors are less resistant to heat due to several physiological conditions, including, but not limited to, hypoxic conditions, insufficient nutrients, disorganized vascular networks, low blood flood, and low tissue conduction. Hyperthermia can be effective as a standalone treatment or adjunct to chemotherapy and/or radiotherapy to eradicate cancer cells by enhancing their vulnerability with produced heat. In one example, a clinical trial has confirmed that an external alternating magnetic field (AMF) can remotely generate therapeutic temperatures on the order of 42° C. in deep-lying tumors containing IONPs without causing severe side effects to healthy tissue.

However, one of the major hurdles of using conventional IONPs for magnetic hyperthermia treatments is that, at least in their current state, nanoparticles are inefficient at converting magnetic energy into heat energy. One study suggests that in order to achieve therapeutic temperature, conventional IONPs must be injected systemically at the extremely high dose of 1,700 mg Fe/kg of body weight. This amount of foreign material introduced to the body results in systemic toxicity, making the magnetic hyperthermia treatment not viable for many, if not all, potential applications.

SUMMARY

Disclosed herein are embodiments of a nanoparticle that are useful for hyperthermia treatment and imaging applications. In some embodiments, the nanoparticle comprises from greater than zero to 5 atom % cobalt, from 18 atom % to 60 atom % iron, and from greater than 35 atom % to 82 atom % oxygen, in amounts relative to each other, such that the total amount of cobalt, iron and oxygen is 100 atom %. The nanoparticle may comprise from 1 atom % to 5 atom % cobalt, such as from 1 atom % to 3 atom % cobalt. In some embodiments, the nanoparticle comprises from 18 atom % to atom % iron, and/or from 35 atom % to 80 atom % oxygen. In one embodiment, the nanoparticle comprises from 2 atom % to 4 atom % cobalt, from 30 atom % to 45 atom % iron, and from 51 atom % to 65 atom % oxygen. And in another embodiment, the nanoparticle comprises from 2 atom % to 4 atom % cobalt, from 18 atom % to 25 atom % iron, and from 60 atom % to 80 atom % oxygen.

In any embodiments, the nanoparticle may have a non-spherical shape. And in some embodiments, the nanoparticle has an irregular hexagon shape. In such embodiments, the size may be measured as the longest distance between two opposite vertices.

In some embodiments, the nanoparticle is substantially free of crystalline defects as observed by high-resolution TEM. Additionally, or alternatively, the nanoparticle may have a specific absorption rate of from 2,500 W $g^{-1}$ to 20,000 W $g^{-1}$, such as from 2,500 W $g^{-1}$ to 15,000 W $g^{-1}$.

The nanoparticle may have a size of from 4 nm to less than 50 nm, such as from nm to 50 nm, or from 14 nm to 30 nm. In a particular embodiment, the nanoparticle is substantially defect-free, comprises from 2 atom % to 4 atom % cobalt, from 30 atom % to 35 atom % iron and sufficient oxygen to make a total amount of cobalt, iron and oxygen is 100 atom %, and has a size of from 10 nm to 14 nm. In another particular embodiment, the nanoparticle is substantially defect free, comprises from 2 atom % to 4 atom % cobalt, from 40 atom % to 50 atom % iron and sufficient oxygen to make a total amount of cobalt, iron and oxygen is 100 atom %, and has a size of 21 nm.

Also disclosed herein are embodiments of a method for making the nanoparticle. In some embodiments, the method comprises combining a first cobalt compound and a first iron compound in a first solvent system to form a first mixture, and heating the first mixture to a first temperature under a first nitrogen flow. The method further comprises cooling the first mixture to room temperature and precipitating a solid intermediate. The solid intermediate then is heated with a second cobalt compound and a second iron compound in a second solvent system to a second temperature and under a second nitrogen flow, before cooling and isolating the nanoparticle. The first cobalt compound and the second cobalt compound independently may be selected from cobalt (II) chloride ($CoCl_2$), cobalt (II) chloride hexahydrate ($CoCl_2$ $6H_2O$), cobalt (II) sulphate ($CoSO_4$), cobalt (II) sulphate heptahydrate ($CoSO_4$ $7H_2O$), cobalt (II) nitrate hexahydrate ($Co(NO_3)_2$ $6H_2O$), cobalt (II) carbonate ($CoCO_3$), or a combination thereof. In some embodiments, the first cobalt compound and the second cobalt compound are the same, but in other embodiments, they are different. And in certain embodiments, the first cobalt compound and the second cobalt compound are both cobalt (II) chloride hexahydrate The first iron compound and the second iron compound independently may be selected from (Zero-valent) $Fe(CO)_5$, iron (III) acetylacetonate ($Fe(acac)_3$), iron (II) sulfate (ferrous sulfate, $FeSO_4$), iron (II) chloride ($FeCl_2$, ferrous chloride), iron (III) nitrate ($Fe(NO_3)_3$, ferric nitrate), iron (III) sulfate ($Fe(SO_4)_3$, ferric sulfate), iron (III) chloride ($FeCl_3$, ferric chloride), or a combination thereof. In some embodiments, the first iron compound and the second iron compound are the same but in other embodiments, they are different. And in certain embodiments, the first iron compound and the second iron compound are both iron (III) acetylacetone.

In any embodiments, the first solvent system and the second solvent system independently may comprise a solvent selected from trioctylamine, docosane, n-octylether, benzyl ether, or a combination thereof. And/or the first solvent system and the second solvent system independently may comprise a surfactant selected from oleic acid, oleylamine, 1-octadecane, or a combination thereof. In some embodiments, the first solvent system and the second solvent system are the same but in other embodiments, they are different. And in certain embodiments, the first solvent system and the second solvent system are both oleic acid, oleylamine and n-octyl ether.

In some embodiments, each of the first temperature and the second temperature independently is from 180° C. to 900° C., such as from 180° C. to 500° C., or from 250° C. to 400° C. In certain embodiments, the first temperature and the second temperature both are 300° C.

In some embodiments, each of the first nitrogen flow and the second nitrogen flow independently is from greater than zero to 900 mL/min nitrogen, such as from 1 mL/min to 400 mL/min nitrogen, or from 1 mL/min to 100 mL/min nitrogen. In certain embodiments, each of the first nitrogen flow and the second nitrogen flow independently is from 10 mL/min to 50 mL/min.

Also disclosed herein are embodiments of a composition comprising the disclosed nanoparticle and a polymer. The polymer may be selected from polyethylene glycol-block-polycaprolactone (PEG-b-PCL), methoxy polyethylene glycol-block-polycaprolactone (mPEG-b-PCL), polyethylene glycol-block-polyvalerolactone (PEG-b-PVL), polyethylene glycol-block-polylactic acid (PEG-b-PLA) or polyethylene glycol-block-poly(lactic acid-co-glycolic acid) (PEG-b-PLGA). In some embodiments, the polymer comprises a PEG moiety, and/or may be a PEG-PCL polymer.

The polymer may have a molecular weight of from 10,000 Da to 20,000 Da, such as from 13,000 Da to 17,000 Da. In some embodiments, the polymer has a molecular weight of about 15,000 Da.

In any embodiments, the nanoparticle may be encapsulated in the polymer.

The composition may further comprise a targeting moiety, which may be conjugated to the polymer. The targeting moiety may be selected from a peptide, protein, small molecule, nucleic acid sequence, antibody, or a combination thereof. In some embodiments, the targeting moiety is an EGFR (Epidermal growth factor receptor), Integrin $\alpha v\beta 6$, Neuropilin-1, PD-L1, a HER2 receptor, or a combination thereof.

In some embodiments, the targeting moiety is a targeting moiety for ovarian cancer, and/or may be a LHRH peptide, $\alpha$-3 integrin receptor, ROR1 (Receptor tyrosine kinase-like orphan receptor1), HE4 (Human epididymis protein 4), 5-Protein signature (OVA1), or a combination thereof. In some embodiments, the targeting moiety is a targeting moiety for endometriosis, and/or may be CD44, EphB4, CXCL13, CTLA4, CD10, vascular endothelial growth factor receptor 2 (KDR) or a combination thereof. In certain embodiments, the targeting moiety is a KDR targeting peptide.

A method for making the composition also is disclosed herein. In some embodiments, the method comprises forming a solution or suspension comprising a nanoparticle disclosed herein and a first organic solvent, forming a mixture comprising the solution or suspension and a polymer in a second organic solvent, and isolating a composition comprising the nanoparticle and the polymer. The first and second organic solvents may be the same solvent, or they may be different solvents. And/or the polymer may comprise a targeting moiety as disclosed herein.

In some embodiments, isolating the composition comprises adding water and evaporating the first and second organic solvents. Additionally, or alternatively, isolating the composition may comprise separating the composition from any non-encapsulated nanoparticles and any non-soluble polymer molecules.

A method of using the nanoparticles also is disclosed. In some embodiments, the method comprises administering a nanoparticle as disclosed herein, or a disclosed composition comprising the nanoparticle, to a subject in need thereof. In some embodiments, the method is a method of treating cancer, for example, ovarian cancer. In other embodiments, the method is a method of treating non-cancerous lesions. In certain embodiments, the method is a method of treating endometriosis. In any embodiments, the method may be a method hyperthermia treatment method.

In some embodiments, administering the nanoparticle or the composition comprising the nanoparticle comprises injecting the nanoparticle or the composition. The nanoparticle or the composition may be injected systemically, or it may be injected locally.

In any embodiments, the method may further comprise applying an alternating magnetic field to the nanoparticle or composition. The alternating magnetic field may have a field strength of from 1 kA/m to 100 kA/m, a frequency of from 50 kHz to 900 kHz, or a combination thereof.

In some embodiments, the nanoparticle or composition is administered in an amount sufficient to provide from 1 mg to 100 mgs of iron per kg weight of the subject, such as an amount sufficient to provide from 1 mg to 50 mgs of iron per kg weight of the subject, or an amount sufficient to provide from 1 mg to 10 mgs of iron per kg weight of the subject.

The foregoing and other objects, features, and advantages of the invention will become more apparent from the following detailed description, which proceeds with reference to the accompanying figures.

BRIEF DESCRIPTION OF THE DRAWINGS

FIG. 45 is a TEM image of seed mediated growth of Cobalt doped iron oxide nanoparticles at a nitrogen flow rate of 10 mL/min, and the corresponding size distribution histogram.

FIG. 46 is a high-resolution TEM image and the inverse FFT lattice fringe image of the Cobalt doped iron oxide nanoparticles from FIG. 45.

SEQUENCE LISTING

Figure 1:
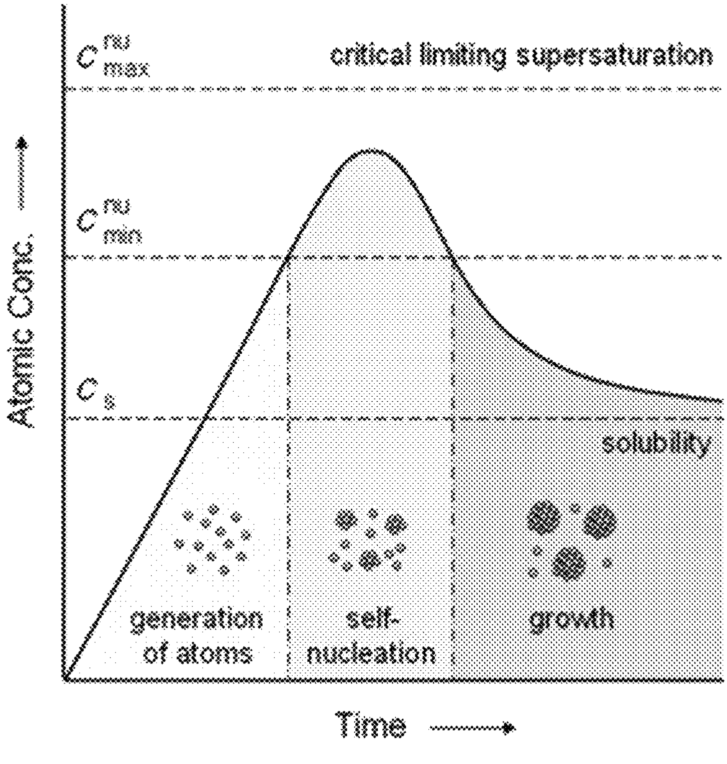
FIG. 1 is a prior art graph of atomic concentration versus time, illustrating typical generation of atoms, nucleation, and subsequent growth of nanoparticles.

The amino acid sequences listed in the accompanying sequence listing are shown using standard three letter code for amino acids, as defined in 37 C.F.R. 1.822. The Sequence Listing is submitted as a .xml file named "Sequence.xml", created on May 11, 2023, 12,288 bytes, which is incorporated by reference herein.

SEQ ID NOS. 1-3 are exemplary LHRH targeting peptides.

SEQ ID NO. 4 is an exemplary vascular endothelial growth factor receptor 2 (KDR) targeting moiety.

SEQ ID NO. 5 is an exemplary α-3 integrin receptor targeting protein.

SEQ ID NO. 6 is an exemplary ROR1 targeting protein.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

The terms "administer," "administering," "administration," and the like, as used herein, refer to methods that may be used to enable delivery of compositions to the desired site of biological action. These methods include, but are not limited to, intraarticular (in the joints), intravenous (i.v.), intramuscular, intratumoral, intradermal, intraperitoneal, subcutaneous, orally, topically, intrathecally, inhalationally, transdermally, rectally, direct injection into a tumor, and the like. Administration techniques that can be employed with the agents and methods described herein are found in e.g., Goodman and Gilman, The Pharmacological Basis of Therapeutics, current ed.; Pergamon; and Remington's, Pharmaceutical Sciences (current edition), Mack Publishing Co., Easton, Pa.

"Nanoparticle" refers to a particle having a size of from 1 to less than 1000 nm, typically, from 1 to 500 nm or from 1 to 100 nm, unless otherwise specified herein.

"Nucleic acid" refers to a polynucleotide molecule. The polynucleotide may be a naturally occurring polynucleotide or a synthetic polynucleotide. A nucleic acid may be a DNA, RNA or mixture of DNA and RNA nucleotides. Typically, the nucleic acid contains from 20 to 10,000 nucleotides or more, such as from 100, 200, 300, 400, 500, 600, 700, 800, 900, 1000, 2000, 3000, 4000, or 5000 nucleotides to 10,000 nucleotides.

Exemplary nucleic acids include, but are not limited to, single stranded DNA, single stranded RNA, double stranded DNA, RNA-RNA hybrid, DNA-RNA hybrid, shortmer, antagomir, antisense, ribozyme, small interfering RNA (siRNA), asymmetrical interfering RNA (aiRNA), microRNA (miRNA), Dicer-substrate RNA (dsRNA), small hairpin RNA (shRNA), sgRNA/pegRNAs, transfer RNA (tRNA), messenger RNA (mRNA), or a combination thereof.

"Peptide" refers to a compound comprising amino acid residues connected by peptide bonds. Typically a peptide compound has from 2 to about 50 amino acid residues.

"Pharmaceutically acceptable excipient" and "pharmaceutically acceptable carrier" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

"Polypeptide" refers to a compound comprising amino acid residues connected by peptide bonds. When the amino acids are alpha-amino acids, either the L-optical isomer or the D-optical isomer can be used. In some embodiments, a polypeptide has from about 50 amino acid residues to 2000 or more amino acid residues.

"Protein" refers to a molecule or complex comprising one or more polypeptides having secondary, tertiary and/or quaternary structure. The secondary, tertiary and/or quaternary structure of a protein typically is stabilized using non-covalent bonds, such as ionic bonds, hydrogen bonds, hydrophobic interactions, and/or van der Walls interactions. Additionally, or alternatively, a protein may include disulfide bonds, such as between the thiol groups of cysteine residues.

"Size" and "average size" as used herein with respect to nanoparticle size, refers to the mode average size of the nanoparticles, that is the size with the greatest number of nanoparticles in a sample, or the peak of a distribution curve. For example, a size distribution histogram, the mode average is the size with the highest bar in the histogram. Unless otherwise specified, the nanoparticle size is measured as the longest distance between two opposite sides or vertices of the nanoparticle.

"Small Molecule" refers to a organic molecule having a molecular weight of about 2000 Daltons or less. In some embodiments, the term "small molecule" refers to a compound that is not a polypeptide, protein, or nucleic acid molecule. A small molecule may be a small molecule therapeutic and/or prophylactic, such as an antibiotic, anti-inflammatory, anticancer, antiviral, immunosuppressant, analgesic, antifungal, antiparasitic, anticonvulsants, antidepressant, anti-anxiety, anti-psychotic, and the like. "Subject" refers to mammals and other animals, particularly humans. Thus disclosed methods are applicable to both human therapy and veterinary applications. In some embodiments, the subject is a human.

II. Overview

Numerous synthetic routes have been reported for the synthesis of iron oxide nanoparticles. However, thermal decomposition method was the preferred method in this work as it facilitates the synthesis of well-defined and colloidally stable nanoparticles, which are suitable for magnetic hyperthermia application. Furthermore, it results with a narrow size distribution among nanoparticles due to the separation of nucleation and growth steps.

In thermal decomposition synthesis, iron precursors are decomposed at high temperatures leading to the accumulation of iron based monomers that in turn triggers nucleation, which is the initial stage for any type of crystal formation. Although the early stages of nuclei formation is not fully understood, its self-assembly to form higher order crystals are thought to follow LaMer's principle as described in the 1950s (LaMer, V. K.; Dinegar, R. H., Theory, production and mechanism of formation of monodispersed hydrosols. Journal of the American Chemical Society 1950, 72 (11), 4847-4854) (FIG. 1). Even though this principle was based on the synthesis of sulfur colloids, its 3 major steps (monomer generation, nucleation, and growth) have been widely adopted to describe the nucleation and growth steps for metal nanocrystals. As shown in FIG. 1, the concentration of metal increases as the precursor decomposes at high temperatures. Those metal ions then react with nearby atoms, such as oxygen, to form monomers. Next, the monomers aggregate into miniscule clusters to form nuclei. The nuclei then grows as more monomers join the structure.

This means that if the amount of monomers at the initial steps is increased, it might lead to an increase in the overall diameter of the final crystal in the growth step. Disclosed herein is data demonstrating that increasing the presence of oxygen in the system led to an increase in the number of monomers formed, which in turn led to increased nanoparticle size.

III. Nanoparticles

Disclosed herein are embodiments of a nanoparticle suitable for magnetic hyperthermia applications. In some embodiments, the nanoparticles are substantially free of crystalline defects. In some embodiments, the nanoparticle is a cobalt iron oxide nanoparticle (Co-IONP). In some embodiments, the nanoparticle comprises, consists essentially of, or consists of, cobalt, iron, and oxygen. In some embodiments, there are no additional elements in the nanoparticle. The nanoparticle may have from greater than zero to 5 atom % cobalt, such as from 1 atom % to 5 atom % or from 1 atom % to 3 atom %. The nanoparticle may have from 18 atom % to 60 atom % iron, such as from 18 atom % to 45 atom %. And nanoparticle also has sufficient oxygen to make the total amount of cobalt, iron and oxygen be 100%. In certain embodiments, a nanoparticle has from 35 atom % to 82 atom % oxygen, such as from 35 atom % to 81 atom %, or from 50 atom % to 80 atom %.

In certain embodiments, the nanoparticle comprises, consists essentially of, or consists of 2 atom % to 4 atom % cobalt, from 30 atom % to 45 atom % iron, and from 51 atom % to 65 atom % oxygen. In other embodiments, the nanoparticle comprises, consists essentially of, or consists of 2 atom % to 4 atom % cobalt, from 18 atom % to 25 atom % iron, and from 60 atom % to 80 atom % oxygen.

In some embodiments, the nanoparticle has a non-spherical shape. In certain embodiments, the nanoparticle has a hexagonal shape, and may be a regular or an irregular hexagonal shape. That is, when viewed by transmission electron microscopy (TEM) a majority (i.e., greater than 50%) of the nanoparticles appear as to have the specified shape, such as irregular hexagons.

The nanoparticles may have a size of from 4 nm or less to 50 nm or more, such as from 10 nm to 50 nm, from 14 nm to 30 nm, from 14 nm to 25 nm, from 19 nm to 30 nm or from 19 nm to 30 nm. The size of the nanoparticles is an average size measured as the longest distance between two opposite sides or vertices, for example, from a TEM image.

In some embodiments, the nanoparticle has a specific absorption rate (SAR) of from 2,500 W $g^{-1}$ to 20,000 W $g^{-1}$ or more, such as from 2,500 W $g^{-1}$ to 15,000 w $g^{-1}$, from 3,000 W $g^{-1}$ to 15,000 W $g^{-1}$, from 4,000 W $g^{-1}$ to 15,000 W $g^{-1}$, or from 4,500 W $g^{-1}$ to 15,000 W $g^{-1}$.

In some embodiments, the nanoparticle has a substantially consistent composition throughout the nanoparticle. However, in other embodiments, the nanoparticle's composition may vary from the center to the outer surface. In certain embodiments, iron and/or oxygen concentrations are highest at the core and gradually drop as the particle approached its outer surface. In other embodiments, the iron and/or oxygen concentrations are highest at the outer surface and concentrations decrease towards the core. Because of the compositional changes between the core and the outer surface of certain nanoparticles, such nanoparticles may be considered core/shell nanoparticles.

IV. Compositions

Also disclosed herein are embodiments of a composition comprising the disclosed nanoparticles. The composition may further comprise a polymer and/or a targeting moiety, such as a peptide.

A. Polymer

The polymer may be any polymer suitable to encapsulate the Co-IONP into a polymer, such as by forming a polymer nanoparticle around the nanoparticle. Additionally, or alternatively, the polymer might be selected to facilitate improving the water solubility of the nanoparticle and/or to facilitate conjugating a targeting moiety. The polymer may be a block copolymer. At least one monomer of the copolymer may be selected to enhance or improve the water solubility of the polymer nanoparticle, and/or at least one monomer of the copolymer may be selected to provide an environment in the polymer nanoparticle suitable for encapsulating inorganic nanoparticles, such as the disclosed Co-IONP. The copolymer may be selected such that it forms a polymer nanoparticle comprising a core suitable to encapsulate Co-IONP. In some embodiments, the copolymer is selected such that it forms a polymer nanoparticle comprising a hydrophobic core and a hydrophilic outer surface.

In some embodiments, the copolymer comprises a polyethylene glycol (PEG) moiety. The copolymer may also comprise one or more additional monomers. The additional monomer(s) may be selected to provide an environment suitable to encapsulate the photosensitive compound. Suitable additional monomers include, but are not limited to, polyesters, polyacids and polylactones.

In certain embodiments, the copolymer is polyethylene glycol-block-polycaprolactone (PEG-b-PCL), methoxy polyethylene glycol-block-polycaprolactone (mPEG-b-PCL), polyethylene glycol-block-polyvalerolactone (PEG-b-PVL), polyethylene glycol-block-polylactic acid (PEG-b-PLA) or polyethylene glycol-block-poly(lactic acid-co-glycolic acid) (PEG-b-PLGA). In certain embodiments, the polymer is mPEG-b-PCL. In particular embodiments, the mPEG-b-PCL comprises an mPEG moiety of from 2,000 Da to 8,000 Da, such as from 3,000 Da to 7,000 Da, or from 4,000 Da to 6,000 Da, and a PCL moiety of from 7,000 Da to 13,000 Da, such as from 8,000 Da to 12,000 Da, or from 9,000 Da to 11,000 Da. In one embodiments, the mPEG-b-PCL polymer comprises an mPEG moiety of 5,000 Da and a PCL moiety of 10,000 Da.

In other embodiments, the PEG-b-PVL comprises a PEG moiety of from 1,000 Da to 7,000 Da, such as from 2,000 Da to 5,000 Da, and a PVL moiety of from 8,000 Da to 25,000 Da or more, such as from 10,000 Da to 20,000 Da.

In certain disclosed embodiments, the polymer is

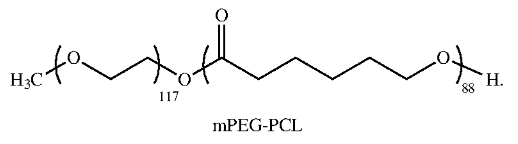

mPEG-PCL

The polymer may be selected to have a molecular weight suitable to form a polymer nanoparticle and encapsulate the Co-IONP. In some embodiments, the polymer has a molecular weight of from about 10,000 Da to 20,000 Da, such as from 13,000 Da to 17,000 Da. As used herein, the "molecular weight" is a weight averaged molecular weight determined by proton NMR and size exclusion chromatography. In certain embodiments, the copolymer had an average molecular weight that is from 13,500 Da to 16,500 Da, such as about 15,000 Da.

B. Targeting Moiety

In some embodiments, the composition comprises a targeting moiety. The targeting moiety is any moiety that can target or direct the composition to a particular site of action, thereby promoting accumulation at that site, and/or reducing systemic distribution. Suitable targeting moieties include, but are not limited to, peptides, proteins, small molecules (for example, folic acid), nucleic acid sequences or antibodies. In some embodiments, the targeting moiety is covalently attached to the polymer nanoparticle. However, in alternative embodiments, the composition does not comprise a targeting moiety.

In some embodiments, the targeting moiety is covalently attached to the polymer nanoparticle. In certain embodiments, the targeting moiety is attached to a PEG moiety on the polymer. There are numerous methods to attach the targeting moiety to the polymer nanoparticle, as a person of ordinary skill in the art will understand. Additional information concerning coupling techniques is provided by Greg T. Hermanson in Bioconjugate Techniques; Academic Press, 1996, which is incorporated herein by reference. The percentage of targeting moiety attached to the polymer nanoparticle may be any amount suitable to facilitate targeting the polymer nanoparticle to a desired organ or tumor. In some embodiments, the amount of targeting moiety attached to the polymer nanoparticle is from greater than zero to 50% or more, weight/weight (weight of polymer labeled with targeting moiety/weight of non-labeled polymer), such as from 1% to 50%, from 1% to 10%, from 1% to less than 5%, or in other embodiments, from 5% to 25%. That is, from greater than zero to 50% of the polymer present in the polymer nanoparticle is labeled with the targeting moiety. In particular embodiments, the amount of targeting moiety used was 1%, 5%, 10%, 25% or 50% w/w targeting moiety-polymer/non-labeled polymer, and in certain embodiments, about 1% w/w targeting moiety-polymer/non-labeled polymer is used.

In some embodiments, the targeting moiety provides at least a 25% increase in the uptake of the composition into the cells, such as from 25% to 200% or more, from 30% to 175%, from 40% to 175%, or from 50% to 175%, compared to the uptake into the cells of a composition that does not comprise a targeting moiety.

1) Cancer

In some embodiments, the targeting moiety is a peptide that preferentially targets the composition to cancer cells. In some embodiments, the peptide is targeted to a receptor that is overexpressed in cancer cells, is not detectably expressed in non-cancer cells, is mutated in cancer cells, or any combination thereof.

In some embodiments, the cancer targeting moiety is an EGFR (Epidermal growth factor receptor), Integrin αvβ6, Neuropilin-1, PD-L1, a HER2 receptor, or a combination thereof.

In some embodiments, the cancer is ovarian cancer. In such embodiments, the peptide may be a luteinizing-hormone-releasing hormone (LHRH). Exemplary LHRH peptides suitable for use in any disclosed embodiments include, but are not limited to, Gln-His-Trp-Ser-Tyr-DLys(DCys)-Leu-Arg-Pro-$NH_2$ (SEQ ID NO. 1); Glp-His-Trp-Ser-Tyr-D-Lys-Leu-Arg-Pro-Gly-$NH_2$ (SEQ ID NO. 2); and Glp-His-Trp-Ser-His-Asp-Trp-Lys-Pro-Gly-$NH_2$ (SEQ ID NO. 3).

Other targeting moieties suitable for targeting ovarian cancer include, but are not limited to, α-3 integrin receptor (for example, cyclic peptide cDGWGPNc, SEQ ID NO. 5), ROR1 (Receptor tyrosine kinase-like orphan receptor1) (for example VATNGKEVVSSTGVLFVKFGP, SEQ ID NO. 6), HE4 (Human epididymis protein 4), 5-Protein signature (OVA1), or a combination thereof.

2) Endometriosis

In some other embodiments, the targeting moiety is a peptide that preferentially targets the composition to endometrium. In such embodiments, the composition may be useful for treating endometriosis. Targeting moieties suitable for targeting the composition to the endometrium include, but are not limited to, CD44, EphB4, CXCL13, CTLA4, CD10, vascular endothelial growth factor receptor 2 (KDR) targeting moiety (such as ATWLPPR, SEQ ID NO. 4), or a combination thereof.

V. Heat Generation

Exposure of the disclosed nanoparticles to a magnetic field, such as an alternating magnetic field (AMF) leads to heat generation, possibly through Brownian relaxation. The movement of these nanoparticles in a suspension generates frictional loss with the environment if the viscosity of the environment allows free rotation. In this regard, it has been reported that one of the highest SAR values is 2453 W $g^{-1}$ at 29 kA $m^{-1}$ and 520 kHz for water suspended 19 nm cubic iron oxide nanoparticle nanoclusters.

Magnetic nanoparticles with a high SAR are highly attractive for magnetic hyperthermia application as higher intra-tumoral temperatures can be achieved with a lower nanoparticle concentration in a short period of time.

Heating capacity of magnetic nanoparticles is measured in terms of specific absorption rate (SAR), which describes the power generated by magnetic nanoparticles (MNPs) per unit mass.

$$SAR = \text{Power/m} = C(\triangle T/\triangle\ t)\ (1/m)$$

Where C is the specific heat capacity, m is the mass concentration of magnetic nanoparticles, and delta T/t is the temperature increase over time.

Bulk materials have several magnetic domains, with each of these domains having their own orientation. In smaller magnetic nanoparticles with mean particle diameter greater than 30 nm, there is only a single domain (mono domain), but larger nanoparticles up to 100 nm can have several magnetic domains. For mono domain nanoparticles, heat generation occurs mainly through Brownian relaxation. The movement of these nanoparticles in a suspension generates frictional loss with the environment. However, this is only if the viscosity of the environment allows free rotation. In the case of restrained physical rotation, the most prevalent heat generation is primarily through Neel relaxation, which is the rotation of the magnetic moments inside the magnetic nanoparticle.

Figure 5:
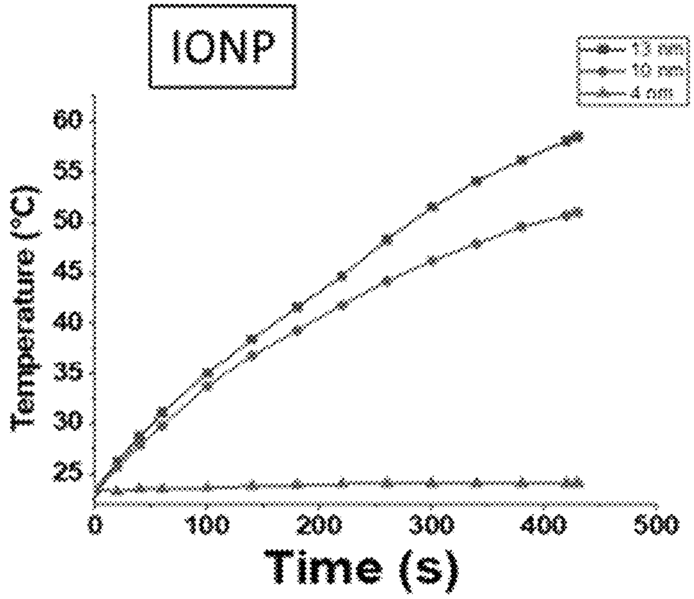
FIG. 5 is a graph of temperature versus time illustrating the increase of temperature as a function of time for iron nanoparticle samples dissolved in THF under the influence of alternating magnetic fields (420 kHz, 26.9 kA/m), and providing a graph of SAR versus size, illustrating the SAR for the different sizes of iron oxide nanoparticles.
Figure 5:
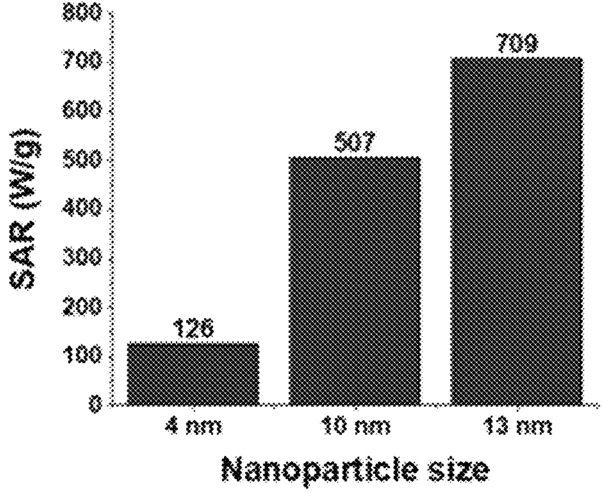
Figure 6:
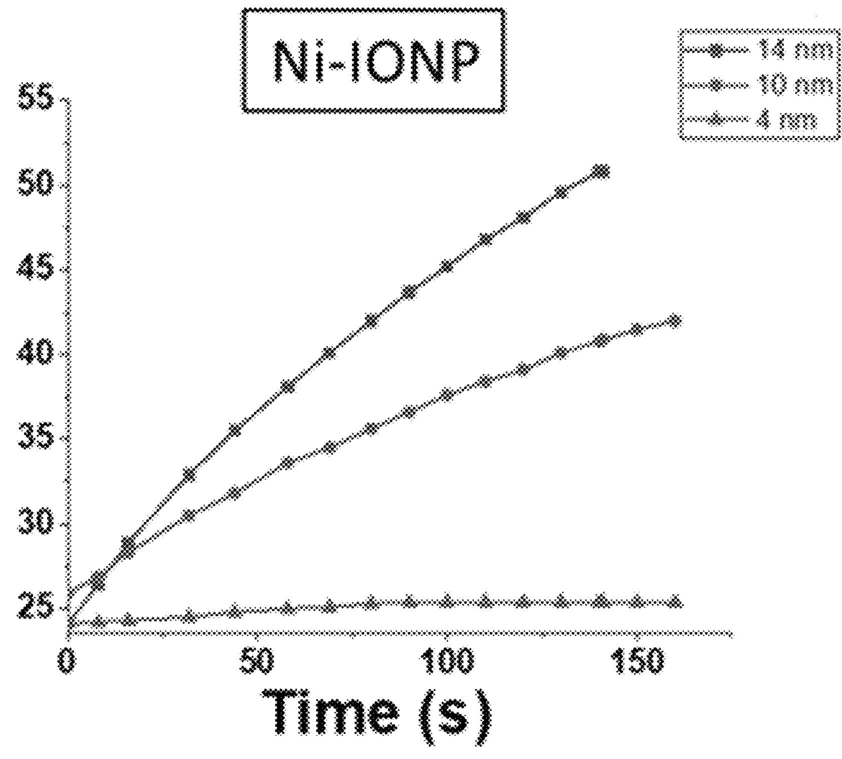
FIG. 6 is a graph of temperature versus time illustrating increment of the temperature as a function of time for nickel-doped iron nanoparticle samples dissolved in THE under the influence of alternating magnetic fields (420 kHz, 26.9 kA/m), and providing a graph of SAR versus size, illustrating the SAR for the different sizes of nickel-doped iron oxide nanoparticles.
Figure 6:
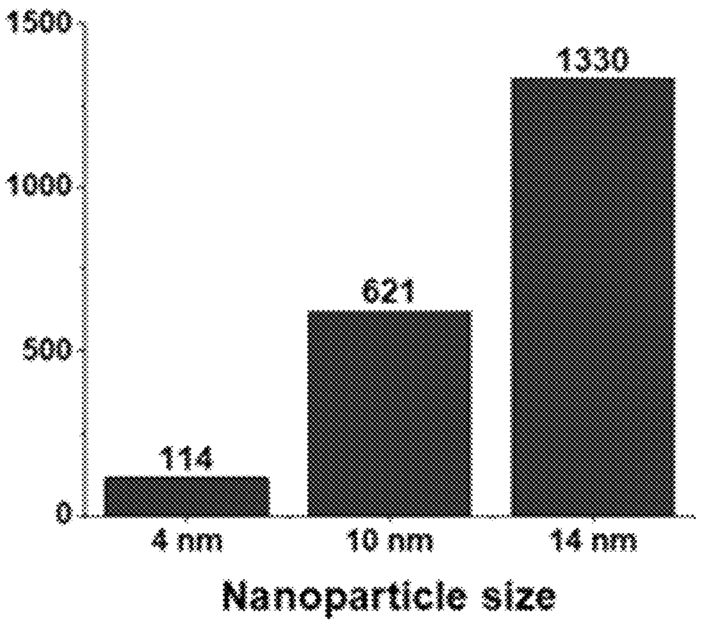
Figure 7:
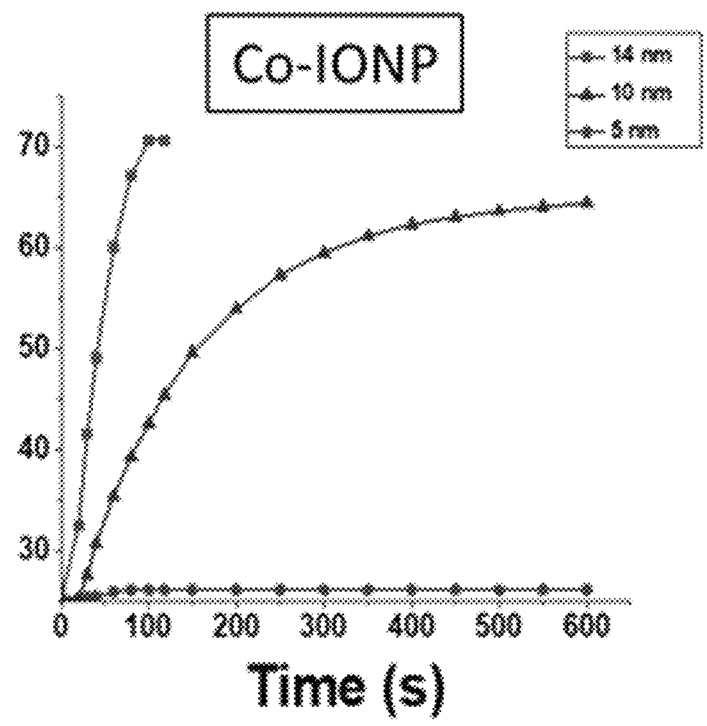
FIG. 7 is a graph of temperature versus time illustrating increment of the temperature as a function of time for cobalt-doped iron nanoparticle samples dissolved in THF under the influence of alternating magnetic fields (420 kHz, 26.9 kA/m), and providing a graph of SAR versus size, illustrating the SAR for the different sizes of cobalt-doped iron oxide nanoparticles.
Figure 7:
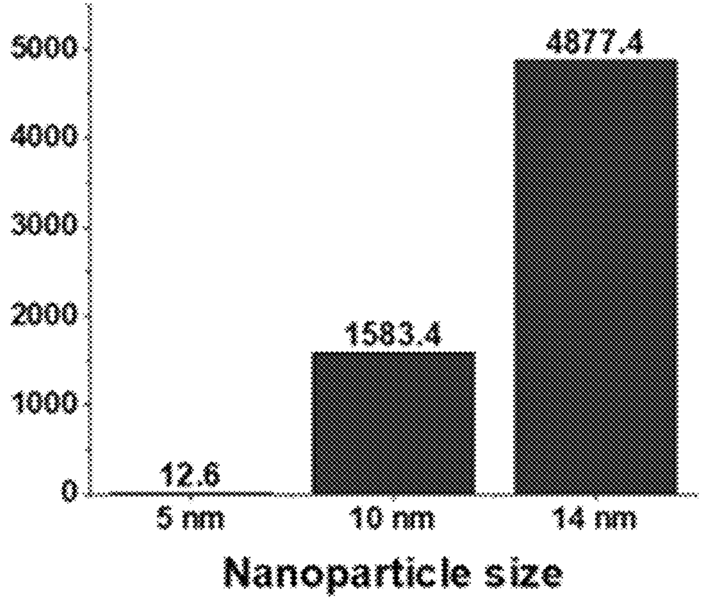

The disclosed cobalt doped iron oxide nanoparticles have an SAR that is higher than SAR values reported in the literature for iron oxide nanoparticles. The literature does not suggest that cobalt doping would produce such an increase in SAR values. A relationship between nanoparticle size and improved SAR for doped and un-doped nanoparticles as shown in FIGS. 5-7. FIGS. 6 and 7 also demonstrate the surprising increase in SAR due to cobalt doping compared to nickel doping.

As these results demonstrate, 14 nm Co-IONPs possessed a high SAR of 4877 W $g^{-1}$. This value was further optimized to 7158 W $g^{-1}$ by growing the nanoparticles to 19 nm using a 50 ml/min nitrogen flow rate and to 14,581 W $g^{-1}$ by growing the nanoparticles to 21 nm using a 10 ml/min nitrogen flow rate. However, attempts to further increase 19 nm or 21 nm Co-IONPs to higher sizes yielded less favorable results.

Figure 52:
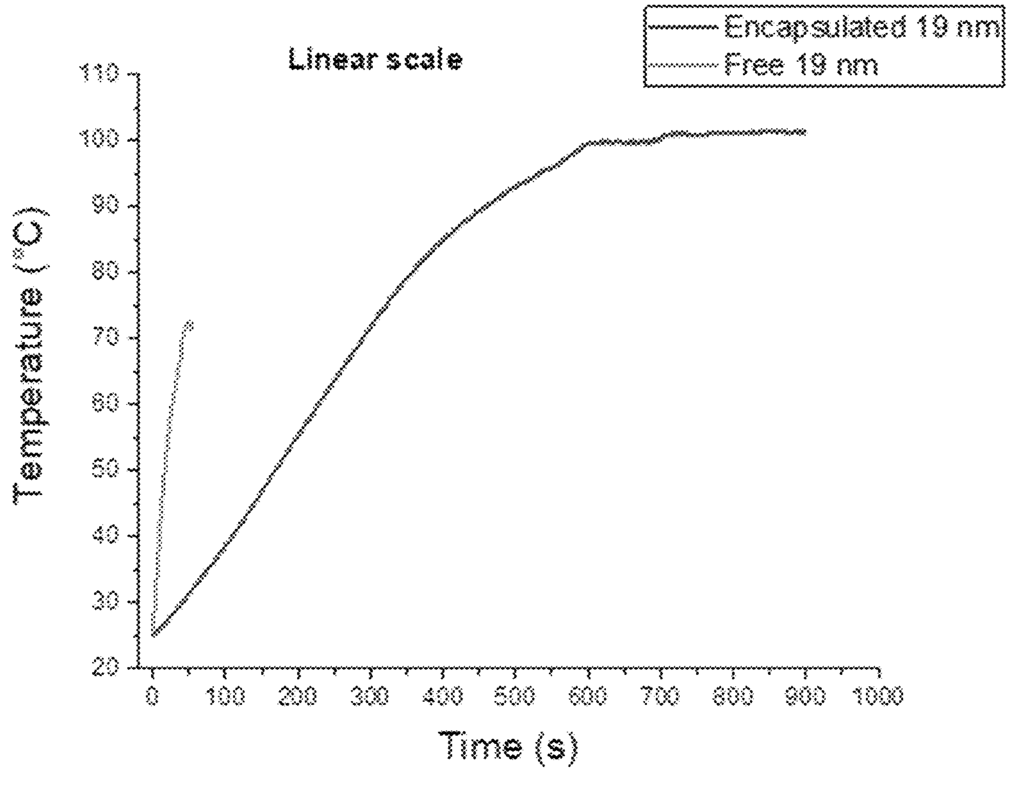
FIG. 52 is a graph of temperature versus time, illustrating the heating profiles of free 19 nm Co-doped hexagonal magnetic nanoparticles (free 19 nm) in THF and encapsulated 19 nm Co-doped hexagonal magnetic nanoparticles (encapsulated 19 nm) in water, both at 1.0 mg of Fe/mL subjected to AMF (f=420 kHz, H=26.9 kA/m).

Without being bound to a particular theory, this high heat production in organic suspension may be primarily attributed to Brownian relaxation and Néel relaxation as the nanoparticles have relatively less restricted motion. In order to make these hydrophobic 19-21 nm Co-IONPs hydrophilic and compatible for intravenous delivery, they were encapsulated in mPEG-PCL. This process will also facilitate their entry into tumor tissue through gaps on the wall of the blood vessels. However, post mPEG-PCL encapsulation, the SAR calculation showed a significant drop to ~419 $Wg^{-1}$. This decrease in the SAR value does not imply any intrinsic changes to the nanoparticle, rather it is due to the extension in the time to start frictional rotation, which is caused by the additional polymeric weight and increased viscosity of water (FIG. 52). Since SAR measurement typically is taken at the early stages of data collection, there can be large variations between same nanoparticle with different hydrodynamic size, but they both reach the boiling point of their respective solvent. As shown by the slope of the graphs in FIG. 52, the free (i.e., not encapsulated) nanoparticles produce an increase in temperature more rapidly that the nanoparticles that are encapsulated in the polymer. However, the encapsulated nanoparticle still achieves the same temperature increases, but over a slightly longer time period.

VI. Synthesis

A. Nanoparticle Formation

In some embodiments, hydrophobic Co-IONPs with sizes of from about 5 to about 14 nm were produced through decreased inert gas ($N_2$) input (from 900 to 10 ml/min, respectively) in a single reaction without the need for precursor or any post-synthesis modifications. Reactions were conducted using a modified thermal decomposition method. Briefly, a cobalt compound and an iron compound are mixed in a solvent system and heated to a temperature suitable to facilitate nanoparticle formation under a flow of an inert gas. The cobalt compound can be any cobalt compound suitable to be a cobalt source for nanoparticle formation, such as, but not limited to, cobalt (II) chloride ($CoCl_2$), cobalt (II) chloride hexahydrate ($CoCl_2$ $6H_2O$), cobalt (II) sulphate ($CoSO_4$), cobalt (II) sulphate heptahydrate ($CoSO_4$ $7H_2O$), cobalt (II) nitrate hexahydrate ($Co(NO_3)_2$ $6H_2O$), cobalt (II) carbonate ($CoCO_3$), or a combination thereof. In certain embodiments, cobalt (II) chloride hexahydrate was used as the cobalt source. The iron compound can be any iron compound suitable to be an iron source for nanoparticle formation, such as, but not limited to, (Zero-valent) $Fe(CO)_5$, iron (III) acetylacetonate ($Fe(acac)_3$), iron (II) sulfate (ferrous sulfate, $FeSO_4$), iron (II) chloride ($FeCl_2$, ferrous chloride), iron (III) nitrate ($Fe(NO_3)_3$, ferric nitrate), iron (III) sulfate ($Fe(SO_4)_3$, ferric sulfate), iron (III) chloride ($FeCl_3$, ferric chloride), or a combination thereof. In certain embodiments, iron (III) acetylacetonate was used as the iron source.

The solvent system can be any solvent system suitable to facilitate the nanoparticle formation reaction. In some embodiments, the solvent system is a mixture of one or more solvents and one or more surfactants. Suitable solvents include, but are not limited to, trioctylamine, docosane, n-octylether, benzyl ether, or a combination thereof. Suitable surfactants include, but are not limited to, oleic acid, oleylamine, 1-octadecane, or a combination thereof. In certain embodiments, the solvent system comprised n-octylether, oleic acid and oleylamine. In some embodiments, a ratio of the surfactant to solvent in the solvent system is from 1:4 to 1:15, such as from 1:5 to 1:8, or from 1:6 to 1:7.5.

The reaction may proceed under a flow of an inert gas, such as nitrogen or argon. In certain embodiments, nitrogen is used. The flow rate of the inter gas is from greater than zero to 900 mL/min or more, such as from 1 mL/min to 500 mL/min, from 1 mL/min to 250 mL/min, from 1 mL/min to 200 mL/min, from 1 mL/min to 100 mL/min, from 5 mL/min to 75 mL/min, or from 10 mL/min to 50 mL/min.

The reaction is heated at a temperature suitable to facilitate nanoparticle formation. The temperature may be from 180° C. or less to 900° C. or more, such as from 180° C. to 750° C., from 180° C. to 500° C., from 200° C. to 400° C., from 250° C. to 400° C., or from 250° C. to 325° C., or about 300° C. The reaction may be heated at a ramp rate of from 250° C./hour to 1000° C./hour, such as from 500° C./hour to 1000° C./hour, from 750° C./hour to 900° C./hour or from 800° C./hour to 850° C./hour. And the reaction may be heated for from 1 minutes or less to 12 hours or more, such as from 10 minutes to 6 hours, from 30 minutes to 3 hours, or from 1 hour to 2 hours. In some embodiments, the reaction is heated for about 1 hour 30 minutes.

After heating, the reaction is allowed to cool to room temperature and a solid is collected. The solid may be an intermediate, and in such embodiments, the reaction proceeds with a second heating step. The second heating step may comprise re-dispersing the intermediate solid in a suitable solvent, such as hexanes or THF, and combining it with a second cobalt compound, and a second iron compound in a second solvent system. The second cobalt compound, the second iron compound, and the second solvent system may be as previously described for the first heating step. In certain embodiments, the same cobalt compound and iron compound are used for both heating steps, but in other embodiments, one or both are different. And in some embodiments, the same solvent system is used in both heating steps, but in other embodiments, a different solvent system is used in the second heating step. In certain embodiments, the same cobalt compound, the same iron compound, and the same solvent system are used in both heating steps.

The reaction mixture is heated at a temperature, at a heating ramp rate, and for a time period as previously described for the first heating step, and under an inert gas flow as previously described. In some embodiments, the same temperature, heating ramp rate, time period and inert gas flow rate are used for both heating steps, but in other embodiments, one or more of the temperature, heating ramp rate, time period or inert gas flow are different in the second heating step from the first heating step.

After cooling the cobalt iron oxide nanoparticles are isolated.

In a typical thermal decomposition synthesis, oxygen is displaced out of the system due to safety concerns linked to ignition and fire. However, this oxygen deprived environment not only leads to smaller nanoparticle size (≤6 nm), which further require multiple seeded mediated growth in order to be used for theranostic applications, but also leads to the formation of defective nanoparticles that are not suitable for magnetic hyperthermia application. However, to the inventors' knowledge, molecular oxygen's ability to influence nucleation steps and produce iron oxide nanoparticles with specific size has not been previously reported.

Figure 2:
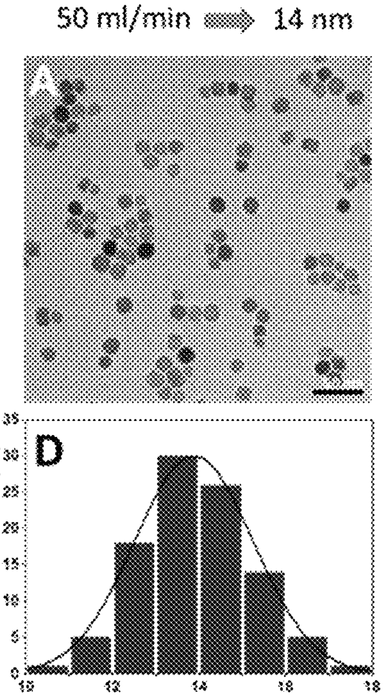
FIG. 2 is a TEM image of exemplary cobalt-doped iron oxide nanoparticles (Co-IONPs) produced with a nitrogen flow of 50 mL/min, and a graph of relative count versus size, providing the size distribution of the nanoparticles and indicating that the nanoparticles have an average size of 14 nm.
Figure 3:
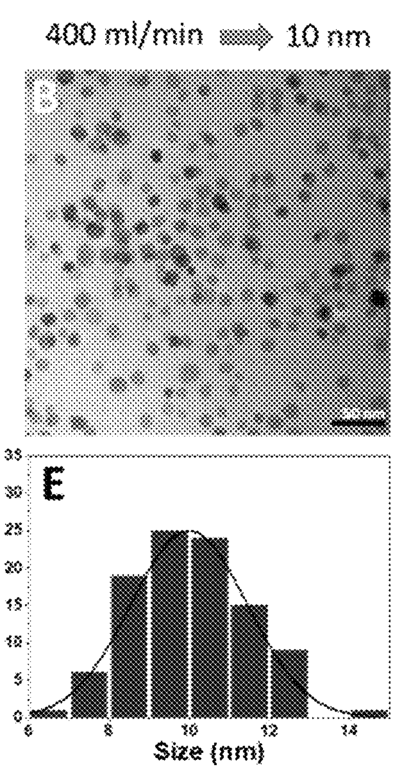
FIG. 3 is a TEM image of exemplary Co-IONPs produced with a nitrogen flow of 400 mL/min, and a graph of relative count versus size, providing the size distribution of the nanoparticles and indicating that the nanoparticles have an average size of 10 nm.
Figure 4:
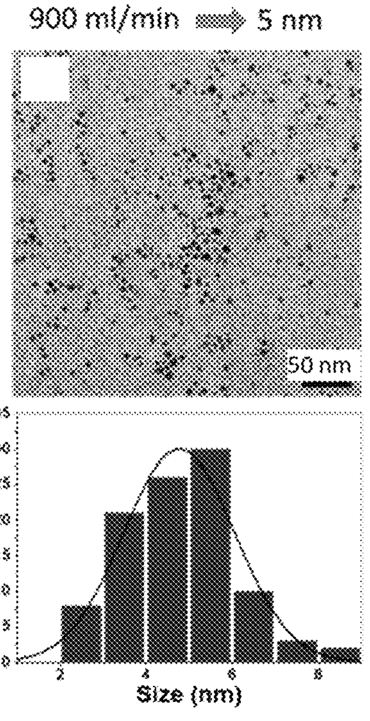
FIG. 4 is a TEM image of exemplary Co-IONPs produced with a nitrogen flow of 900 mL/min, and a graph of relative count versus size, providing the size distribution of the nanoparticles and indicating that the nanoparticles have an average size of 5 nm.

In some embodiments of the nanoparticle compositions, cobalt doped nanoparticles are prepared using different amount of an inert gas, such as nitrogen, input during synthesis to reduce the amounts of molecular oxygen. In some embodiments, the rate of inert gas flow used during the synthesis is from greater than zero to 900 mL/min, such as from 1 mL/min to 500 mL/min, from 1 mL/min to 100 mL/min, or from 10 mL/min to 50 mL/min. In some embodiments, 50 mL/min, 400 mL/min, and 900 ml/min were used. Lower inert gas input allows for increased oxygen presence in the system as compared to higher inert gas input. As shown in FIGS. 2-4, nanoparticle size was reproducibly increased from about 5 nm to about 14 nm only through decreased displacement of molecular oxygen from the system and without the need for post synthesis modifications.

Furthermore, energy dispersive X-ray spectroscopy (EDS) mapping analysis indicated that Co-IONPs synthesized at higher nitrogen input exhibited decreased oxygen concentration.

B. Composition

Embodiments of a method for preparing a composition comprising the disclosed nanoparticles, and a polymer and/or a targeting moiety also is disclosed herein. In some embodiments, the method comprises forming a suspension comprising the cobalt iron oxide nanoparticles in a suitable solvent, such as tetrahydrofuran (THF). A solution comprising the desired polymer in a suitable solvent, such as THE, also is prepared. The nanoparticle suspension and the polymer solution then are combined to facilitate forming polymer nanoparticles encapsulating at least some of the Co-IONP. In some embodiments, the nanoparticle suspension is added to the polymer solution. Dextrose solution in water may be added and the organic solvent is evaporated. Any non-encapsulated, hydrophobic Co-IONPs and non-soluble polymer molecules are separated from the polymer nanoparticles loaded with Co-IONP, such as by centrifuging, filtering, and/or using a magnetic field. The size of final nanoparticles was determined using Dynamic Light Scattering (DLS) spectra and Cryo-TEM.

In embodiments comprising a targeting moiety, the targeting moiety may be conjugated to the polymer. In some embodiments, the targeting moiety is attached to the polymer before the polymer nanoparticle is formed. In certain embodiments, the polymer comprises a PEG moiety and the targeting moiety is conjugated to a PEG moiety in the polymer. In some embodiments, the polymer, such as a PEG-containing polymer, is treated with a carbodiimide reagent, such as N,N'-dicyclohexylcarbodiimide (DCC), and N-hydroxysuccinimide (NHS) in a suitable solvent, such as an aprotic solvent, for example, acetonitrile.

VII. Applications and Dosage

The disclosed nanoparticles and compositions thereof are useful to treat diseases and conditions where hyperthermia treatment is useful. In some embodiments, the disclosed nanoparticles or compositions thereof, are useful to treat cancer, for example, solid tumor cancers, such as, but are not limited to, ovarian cancer, breast cancer, prostate cancer, pancreatic cancer, head and neck cancer, liver cancer and skin melanomas. In certain embodiments, the cancer is ovarian cancer.

In other embodiments, the disease or condition is non-cancerous, such as non-cancerous lesions. In some embodiments, the disease or condition is endometriosis.

In any embodiments, the nanoparticle, or a composition thereof, is administered to a subject in need thereof in an amount sufficient to treat the disease or condition. The subject may be a human or animal subject, such as a mammal. In some embodiments, the subject is a human. In any embodiments, the nanoparticle, or a composition thereof, is administered in an amount sufficient to administer from 1 mg or less to 100 mgs or more iron to the subject, such as from 1 mg to 50 mgs iron, from 1 mg to 25 mgs iron or from 1 mg to 10 mgs iron.

After administration, the subject is exposed to a magnetic field, such as an alternating magnetic field. In some embodiments, the magnetic field is applied by an MRI machine. The magnetic field may have a field strength of from 1 kA/m or less to 100 kA/m or more. And/or the magnetic field may have a frequency of from 50 kHz or less to 900 kHz or more.

The magnetic field may be applied at any time period after the nanoparticle, or a composition thereof, is administered sufficient to provide a beneficial effect to the subject. In some embodiments, the magnetic field is applied from substantially immediately after the nanoparticle, or a composition thereof, is administered to the subject, to 7 days or more after administration, such as from 1 minute after administration to 5 days after administration.

The nanoparticle, or a composition thereof, may be administered to the subject by any suitable route. In some embodiments, the nanoparticle, or a composition thereof, is administered by injection. In any embodiments, administration may be systemic, or the administration may be a local administration, such as injecting directly into a tumor and/or tissue that is to be treated.

The nanoparticle, or a composition thereof, may be administered as a pharmaceutical composition comprising the nanoparticle, or a composition thereof, and a pharmaceutically acceptable excipient. The pharmaceutically acceptable excipient may be any excipient suitable to formulate the nanoparticle, or a composition thereof, for administration by a desired route. In some embodiments, the pharmaceutical composition is formulated for administration by injection. In some embodiments, the pharmaceutically acceptable excipient is water, a PBS buffer, 5% dextrose solution or saline solution.

VIII. EXAMPLES

Example 1

Cobalt (II) chloride hexahydrate ($CoCl_2$ 6H2O, 1.5 mmol) and iron (III) acetylacetone (Fe(acac) 3, 5.00 mmol) were added to a solution containing oleic acid (2.5 mL), oleylamine (2.2 mL), and n-octyl ether (30 mL) in a 250 mL three-neck round-bottom flask and heated to 300° C. at a ramping rate of 840° C./hr under controlled nitrogen or argon flow and vigorous stirring. After 1 hour and 30 minutes, the mixture was cooled to room temperature and the product was precipitated with ethanol (30 mL), followed by centrifugation at 7830 rpm for 10 minutes. The obtained precipitate of 14 nm (for example) cobalt doped iron oxide nanoparticles (Co-IONP) were re-dispersed in hexane (10 mL), and used for the next step to produce 19 nm Co-IONPs.

In the second step, the same precursors as above were combined in a 250 mL three-neck round-bottom flask with freshly made 14 nm $CoFe_2O_4$ nanoparticles suspended in 10 mL of hexane (8 mg/mL). The reaction was then heated to 300° C. at a ramping rate of 840° C./hr under controlled nitrogen (50 ml/min to produce 19 nm, or ml/min to produce 21 nm) or argon flow and vigorous stirring. Subsequently, the resulting reaction mixture was cooled to room temperature, ethanol (30 mL) was added, 10 followed by centrifugation at 7830 rpm for 10 minutes.

The obtained precipitate was washed and purified in a 1:4 THF: EtOH (25 ml) two times. The obtained 19 or 21 nm Co-IONPs were used in subsequent experiment to produce the water soluble nanoparticles.

Example 2

Water Soluble Nanoparticles

Polymeric nanoparticles loaded with Co-IONPs were prepared by a solvent evaporation method. Briefly, to Co-IONPs suspended in 1 mL of THF (2 mg Fe/mL) were added to 1 mL of THE solution containing m-PEG-PCL (5 kDa PEG-10 kDa PCL, 100 mg/mL) followed by constant stirring for 2 minutes. Next, 2 mL of 5% dextrose solution in water was added to the reaction mixture and stirred for 10 seconds and the remaining THF was air dried. To remove any non-encapsulated, hydrophobic Co-IONPs and non-soluble PEG-PCL molecules, the prepared aqueous solution was centrifuged at 1,000 g for 5 minutes and filtered through a 0.2 μm cellulose acetate filter (cellulose acetate, VWR International, Radnor, PA). To remove self-assembled empty PEG-PCL nanoparticles (without Co-IONP), the filtered solution was subsequently placed on a strong magnet (SuperMag Separator, Ocean NanoTech) for 6 hours and PEG-PCL nanoparticles loaded with magnetic Co-IONPs (nanoclusters) were separated and re-dispersed in 5% dextrose. The size of final nanoparticles was determined using Dynamic Light Scattering (DLS) spectra and Cryo-TEM.

Example 3

A. Materials

Iron (III) acetylacetonate (($Fe(acac)_3$) was purchased from ACROS Organics (Fair Lawn, NJ, USA). Oleylamine was purchased from Sigma-Aldrich (St. Louis, MO, USA). Oleic acid and cobalt (II) chloride hexahydrate ($CoCl_2$ $6H_2O$) was obtained from Alfa Aesar (Ward Hill, MA, USA). n-Octyl ether was purchased from Tokyo Chemical Industry Co. (Tokyo, Japan). SiNc (silicon 2,3-naphthalocyanine bis (trihexylsilyloxide)) was purchased from Alfa Chemistry (Ronkonkoma, NY, USA). PEG-PCL (methoxy poly(ethylene glycol)-b-poly(ε-caprolactone), MW: PEG (5k)-PCL(10k)) and Carboxyl PEG-PCL (MW: HOOC-PEG (5k)-PCL(10k))) were purchased from Advanced Polymer Materials Inc. (Montreal, Canada). KDR peptide (ATWLPPR) was purchased from Biomatik (Wilmington, DE, USA). N,N'-dicyclohexylcarbodiimide (DCC) was purchased from Oakwood Products, Inc (West Columbia, SC, USA). N-hydroxysuccinimide (NHS) was purchased from Sigma Aldrich (St. Louis, MO, USA). A quantitative fluorometric peptide assay was purchased from Pierce (Waltham, MA, USA). Spherical iron oxide nanoparticles dispersed in chloroform were obtained from Ocean NanoTech (San Diego, CA, USA).

B. Methods

Synthesis of Cobalt-Doped Hexagonal Nanoparticles:

A modified thermal decomposition method was used to prepare cobalt-doped iron oxide nanoparticles with a hexagonal shape. Briefly, cobalt (II) chloride hexahydrate ($CoCl_2$ $6H_2O$, 1.5 mmol) and iron (III) acetylacetone ($Fe(acac)_3$, 5.00 mmol) were added to a solution containing oleic acid (2.5 mL), oleylamine (2.2 mL), and n-octyl ether (30 mL) in a 250 mL three-neck round-bottom flask and heated to 300° C. at a ramping rate of 840° C./h under 50 mL/min nitrogen flow (for example, 0.1 to 50 ml/min) and 300 rpm stirring. After 90 minutes, the reaction mixture was cooled down to room temperature and the reaction product was precipitated with ethanol (30 mL), followed by centrifugation at 7830 rpm for 10 minutes. The obtained precipitate was re-dispersed in 10 mL hexane (8 mg/mL) and added to a 250 mL three-neck round-bottom flask containing the same precursors concentrations (e.g., $CoCl_2$ $6H_2O$, $Fe(acac)_3$, oleic acid, oleylamine and n-octyl ether.) that were used in the initial reaction. Under controlled nitrogen flow and vigorous stirring, the reaction mixture was heated to 300° C. at a rate of 840° C./h. After 90 minutes, it was cooled down to room temperature and precipitated with ethanol as described above. The obtained precipitate was washed twice with a 1:4 THF:ethanol (25 mL) to obtain the final nanoparticles dispersed in THF.

Characterization of Hexagonal and Spherical Nanoparticles:

The size and morphology of the synthesized nanoparticles were evaluated using FEI Tecnai™ Spirit Transition Electron Microscope equipped with an Eagle™ 2K CCD multiscan camera (FEI, Hillsboro, OR, USA). Chemical composition of the nanoparticles was analyzed by energy dispersive X-ray spectroscopy (EDX) using an FEI 80-300 kV Titan Analytical Transmission Electron Microscope (FEI, Hillsboro, OR, USA). The heating efficiency of hexagonal and spherical nanoparticles in the presence of AMF was measured and compared in terms of specific absorption rate (SAR) by using the equation below:

$$SAR = (CVs/\mathrm{m}) \times (dT/dt),$$

where C is the specific heat capacity of the medium, Vs is the sample volume, m is the mass of magnetic nanoparticle suspended in the medium, and dT/dt is the initial slope of the time-dependent temperature curve.

Vials containing tested nanoparticles in THF (1 mg Fe/mL) were thermally insulated using styrofoam and inserted in a water-cooled 6-turn copper coil (4 cm inner diameter). Each vial was then exposed to AMF (420 kHz, 26.9 kA/m) generated by an induction heating system (MSI Automation, Wichita, KS, USA) and temperature changes were measured by placing a fiber optic probe (Neoptix Inc., QC, Canada) in the center of the solution. The first few points (for example, 6 points) of the temperature vs time graph were used to generate the slope (dT/dt) which was then multiplied by specific heat capacity of the solvent (C), sample volume (1 ml), and divided by mass of Fe(1 mg). Additional information concerning measuring SAR can be found in Albarqi, et al., *ACS Nano* 2019, 13, 6, 6383-6395.

Conjugation of KDR Targeting Peptide to PEG-PCL Polymer:

N,N'-dicyclohexylcarbodiimide (DCC) (2 equivalents to carboxyl PEG-PCL) and N-hydroxysuccinimide (NHS) (4 equivalents to carboxyl PEG-PCL) were added to a solution of Carboxyl PEG-PCL (32 mg, 2.1 μmol) in 1.5 mL acetonitrile. After 1 hour of mixing, KDR peptide (2 mg, 2.4 μmol) was added to the reaction mixture, which was stirred overnight at room temperature. The conjugation was confirmed using quantitative fluorometric peptide assay according to the manufacturer's protocol. The fluorescence of the product mixed with the amine-reactive fluorescent detection reagent was measured at 475 nm. The amine-reactive reagent specifically labeled the N-terminus of unconjugated peptides. The conjugation yield was 89.2%.

Synthesis and Characterization of Non-Targeted and KDR-Targeted Magnetic Nanoparticles:

Non-targeted and KDR-targeted magnetic nanoparticles (MN) were prepared using the modified solvent evaporation method. To prepare non-targeted MN, PEG-PCL (50 mg/mL) and synthesized MN (1 mg/mL) were mixed in THF (1 mL). Then, dextrose 5% in water (1 mL) was added to the prepared THF mixture and stirred for 3 minutes. The resulting solution was left overnight at room temperature to slowly evaporate THF. To prepare KDR-modified MN, a mixture of the synthesized KDR-PEG-PCL (5 mg/mL) and PEG-PCL (45 mg/mL) was used in the first step of the above-described procedure. Finally, non-targeted and KDR-targeted nanoparticles loaded with a fluorescence dye (Nile Red or SiNc) were prepared by introducing either Nile Red (0.2 mg/mL) or SiNc (0.2 mg/mL) to the THE mixture as described above. To remove any non-encapsulated hydrophobic CoMn-IONP and non-soluble PEG-PCL molecules, the prepared aqueous solution was centrifuged at 1000 g for 5 minutes and filtered through a 0.2 μm cellulose acetate filter (VWR International).

Cryogenic transmission electron (cryo-TEM) microscope, Glacios™ Cryo-TEM with Gatan K3 Camera (Thermo Fisher Scientific, Waltham, MA), was employed to assess the morphology of the prepared non-targeted and KDR-MN. Their hydrodynamic size, PDI and zeta potential were determined by ZetaSizer NanoSeries (Malvern, Worcestershire, UK). Finally, to confirm encapsulation of a corresponding dye, fluorescence spectra of both non-targeted and KDR-modified nanoparticles were recorded and analyzed using a Cary Eclipse R3896 fluorescence Varian spectrophotometer (Mulgrave, Victoria, Australia).

Primary Tissue Culture:

Endometriosis, endometrium and kidney tissues were collected from rhesus macaques at necropsy. Random samples of the endometrium and endometriosis lesions were frozen, cryosectioned, and the expression of KDR by these tissues was tested by immunohistochemistry (AB #PA5-16487; Thermo Fisher). Macaque primary cells were isolated from the collected tissues according to published protocols. These cells were propagated in Modified Eagle's Medium supplemented with 10% Fetal Bovine Serum, antibiotic and antimycotic and allocated to treatments. The KDR expression in the collected tissues and isolated cells was evaluated by qPCR.

Cellular Internalization of Non-Targeted and KDR-Targeted Nanoparticles:

Primary macaque endometriosis, endometrium, and kidney cells were seeded in 6-well plates (30,000 cells/well) and incubated with non-targeted and KDR-targeted nanoparticles loaded with Nile red NP (0.5 μg/mL) for 24 hours. Afterward, the medium was removed, cells were washed with DPBS three times and collected. Cell fluorescence generated by internalized Nile red was measured using a BD Accuri C6 flow cytometer (BD Biosciences, CA, USA).

In Vitro Magnetic Hyperthermia Generated by Non-Targeted and KDR Targeted Magnetic Nanoparticles:

Monolayers of primary macaque endometriosis cells seeded in 100 mm dishes (200,000 cells/well) were incubated with non-targeted MN and KDR-MN (25 μg Fe/mL) for 24 hours, respectively. Cells were washed with DPBS, detached by 0.25% trypsin/EDTA, and centrifuged at 10,000 rpm for 1 minute to form cell pellets. The pellets were maintained in a constant volume of 0.1 mL cell culture media in 0.6 mL microcentrifuge tubes. Samples were then placed in the center of a six-turn copper coil (inner diameter 4 cm) and exposed to AMF (420 kHz, 26.9 kA/m) for 30 minutes. The temperature changes were measured by placing a fiber optic probe (Neoptix Inc., QC, Canada) inside the cell pellets. The water jacket inside the coil was maintained at about 37° C., and the samples were allowed to equilibrate to this temperature before exposure to AMF. Controls were carried out with non-treated cells exposed to AMF alone and with treated cells exposed to no field. Then, treated cells were re-suspended in media and seeded in 96-well plates at a density of 10,000 cells/well and cultured for an additional 48 hours. Finally, cell viability was assessed using a calcein-AM assay.

A Mouse Model for Endometriosis:

The macaque endometriotic tissues were obtained from monkeys in the mid secretory phase of the menstrual cycle and transplanted into subcutaneous pockets of 3-week old female ICR SCID mice (Taconic Biosciences, Germantown, NY, USA) according to the procedure described by Moses, et al. *Small,* 2020, vol. 16 (18) e 1906936 (up to 5 grafts/mouse). The mice were treated sequentially with estradiol ($E_2$; 90 day release) plus progesterone (P; 14 day release) delivered by implants (Innovative Research of America). The implants produce primate levels of $E_2$ (100-120 μg/ml) and P (10-15 ng/ml) in the mice. P implants were replaced after 28 days to create human-length artificial menstrual cycles in the mice. Under these conditions, the grafts develop into lesions that grow in response to $E_2$ and bleed in response to P withdrawal similar to endometriosis in women and monkeys.

Evaluation of KDR-MN Biodistribution:

Mice with multiple endometriotic xenografts were IV injected with 200 μL of KDR-MN (3 mg Fe/kg) loaded with a NIR dye (SiNc). The Pearl Impulse Small Animal Imaging System (LI-COR, Lincoln, NE) was used to record the NIR fluorescence signal generated by SiNc in the mouse body. Endometriotic grafts and various organs were collected 5 days post-euthanasia, sectioned and stained with Prussian blue using the iron stain kit (Polysciences, Inc., Warrington, PA, USA). The stained tissues were imaged with a Keyence BZ-X Fluorescence Microscope (Keyence, Osaka, Japan).

Evaluation of Nanoparticles Heating Efficiency:

Mice were IV injected with non-targeted MN (3 mg Fe/kg), KDR-targeted MN (3 mg Fe/kg) or saline and exposed to the AMF (420 kHz, 26.9 kA/m) at 24 hours and 5 days after nanoparticles administration. Before AMF exposure, mice were anesthetized with isoflurane and Neoptix T1 temperature probes were placed into the core of the endometriotic graft or adjacent to the graft. Each animal was placed inside the round induction coil (6 turns, 4 cm inner diameter), and temperature measurements were taken during animal exposure to the AMF for up to 30 minutes.

Evaluation of the Therapeutic Efficacy of Magnetic Hyperthermia:

Two groups of mice (5 animals per group) bearing 3-4 endometriotic grafts were injected IV with a single dose of KDR-MN (3 mg Fe/kg) or saline, respectively. The rear third of each mouse (including 2-3 grafts) was placed inside the round induction coil at day 5 post-injection and exposed to the AMF (420 kHz, 26.9 kA/m) for 20 minutes. The growth of each graft was measured by caliper for four weeks after treatment. Measured parameters were used to calculate graft volumes according to the following Equation:

$$V = W^2 \times L/2,$$

where V, W, and L are volume, width, and length of grafts, respectively.

The AMF-exposed grafts in mice injected with KDR-MN were used to evaluate the ability of magnetic hyperthermia to ablate endometriotic lesions. The non-exposed grafts in the same mice were used to assess the effect of KDR-MN alone on the growth of endometriotic lesions. The effect of AMF alone on endometriotic lesions was tested using AMF-exposed grafts in mice injected with saline. The other grafts in saline-injected mice were used as non-treated controls. At the end of the study, blood samples were collected and submitted for biomarker analysis to the IDEXX laboratory (Portland, OR, USA).

MRI:

Mice bearing five subcutaneous endometriotic grafts were injected via tail vein with 200 μL of KDR-MN at a dose of 3 mg Fe/kg or with saline as a control. Tumor imaging by MRI was performed 24 hours after injection and immediately after euthanization (Bruker BioSpin GmbH 11.75 Tesla (T)/500 MHz horizontal magnet equipped with ParaVision version 5.1 software (Ettlingen, Germany)). The following imaging parameters were used: Gradient Images: T2*-weighted fast low angle shot (FLASH) gradient-echo sequence with a repetition time (TR) of 500 milliseconds (ms), a matrix size of 128×192 slice thickness of 1 mm, 30 slices, with flip angle set to 40 degrees. Varying echo times (TE) of 1.12, 3.0, 4.5, and 6.0 milliseconds were employed. The display field of view (DFOV) was 3.3×3.8 cm. T2 Images: T2 weighted rapid acquisition with relaxation enhancement (RARE) sequence with a TR 7000-8150 ms, TE of 23.65 ms, echo train length (ETL) of 8, a matrix size of 512×256, slice thickness of 0.5 mm, 60 slices and flip angle set to 180 degrees, and DFOV=3.5×3.5 cm.

Statistical Analysis:

Data were analyzed using descriptive statistics, two-tailed unpaired t-test, and presented as mean values±standard deviation (SD) from three to eight independent measurements. The comparison among groups was performed by one-way analysis of variance (ANOVA). The differences were considered significant at a level of $p<0.05$.

C. Results and Discussion

I. Preparation of Magnetic Nanoparticles with High Heating Efficiency

Figure 8:
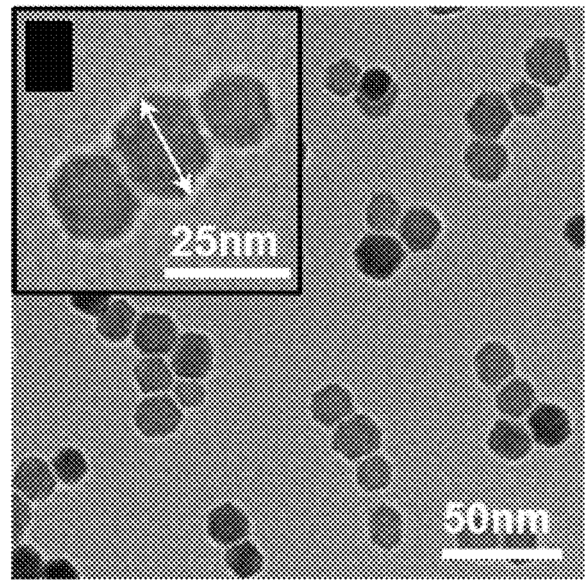
FIG. 8 is a TEM image of cobalt-doped iron oxide nanoparticles illustrating their hexagonal shape.
Figure 9:
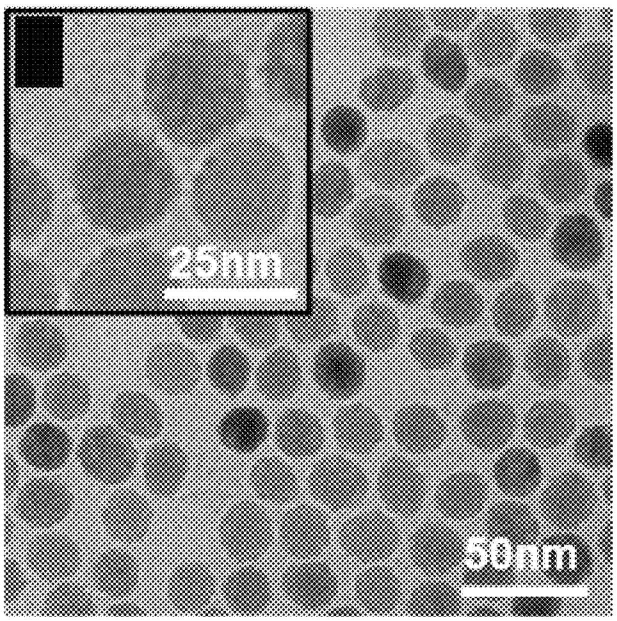
FIG. 9 is a TEM image of un-doped commercially available iron oxide nanoparticles illustrating their spherical shape.
Figure 10:
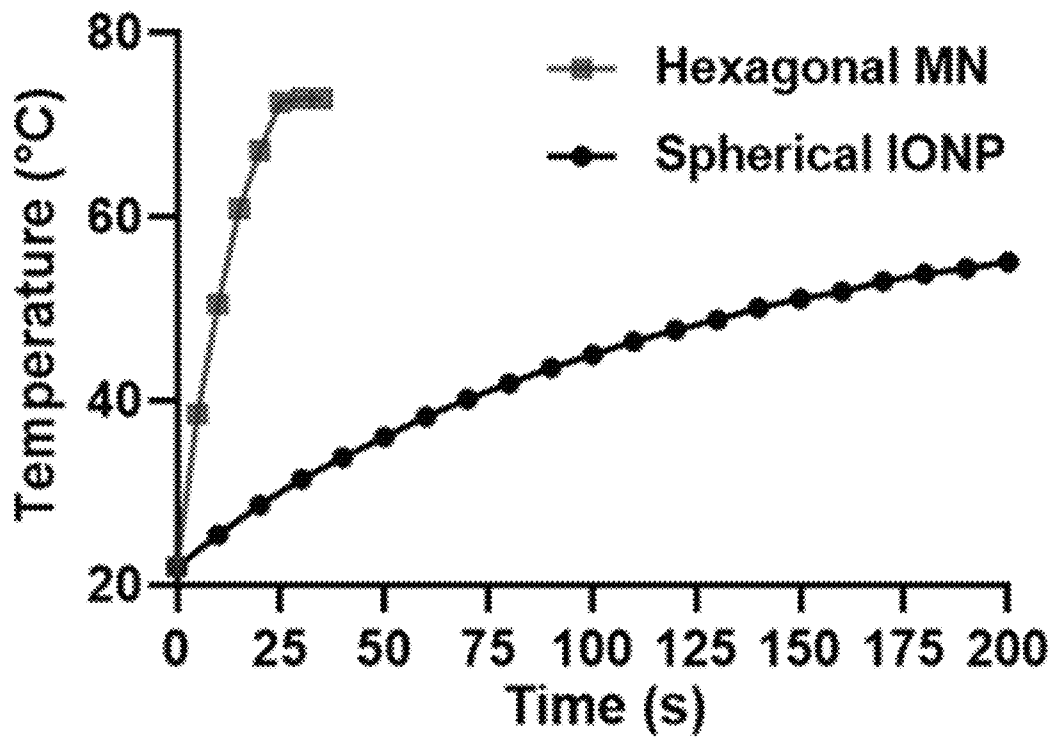
FIG. 10 is a graph of temperature versus time, illustrating the heating profiles of Co-doped hexagonal magnetic nanoparticles (Hexagonal MN) and spherical iron oxide nanoparticles (Spherical IONP) in THF (1.0 mg of Fe/mL) subjected to AMF (f=420 kHz, H=26.9 kA/m).

Novel iron oxide-based magnetic nanoparticles (MN) with high heating efficiency were synthesized by using a modified thermal decomposition approach. Transmission electron microscopy (TEM) analysis revealed that MN have an irregular hexagonal shape, and the average size is 18.9±1.8 nm (FIG. 8). The size of MN was measured as the longest distance between two opposite vertices of an irregular hexagon (FIG. 8 inset). Energy dispersive X-ray (EDX) analysis revealed that synthesized cobalt-doped MN contained about 1.3% Co. Measurements (FIG. 10) revealed that the heating efficiency of the synthesized hexagonal MN (specific absorption rate (SAR)=8057 W/g) upon exposure to AMF (f=420 kHz; H=26.9 kA/m) was 6.4 times higher than spherical iron oxide nanoparticles (SAR=1254 W/g) with a similar size 19.5±1.9 nm (FIG. 9).

Cobalt can be potentially toxic if it were to leach from the disclosed nanoparticles. However, it has previously been reported that the leaching of Co from nanoparticles doped with 8.1% Co (a significantly higher cobalt content that the disclosed nanoparticles) was negligible after incubation in serum at 37° C. for seven days and that nanoclusters were not genotoxic. Moreover, mice did not display any signs of toxicity after multiple injections of these nanoparticles. And a clinical trial with people who voluntarily ingested a cobalt supplement (0.080-0.19 mg Co/kg× day) over three months revealed no side effects. Additionally, the disclosed nanoparticles can be administered at a very low Co dose (<0.04 mg/kg) and still generate the necessary therapeutic intra-lesional temperatures upon exposure to AMF (>45° C.).

Figure 11:
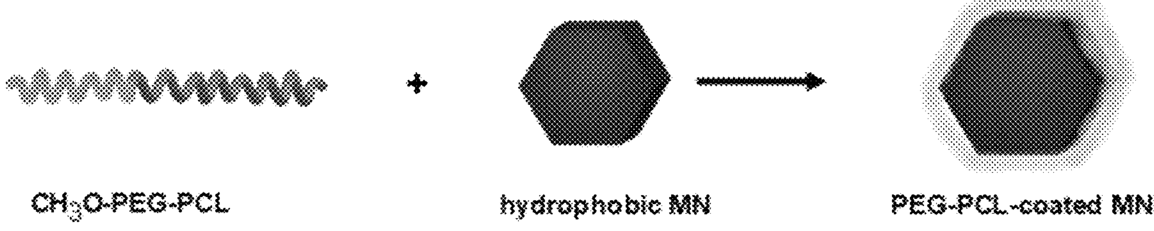
FIG. 11 is a schematic diagram illustrating how the disclosed Co-IONPs are encapsulated in an exemplary PEG-PCL polymer.
Figure 12:
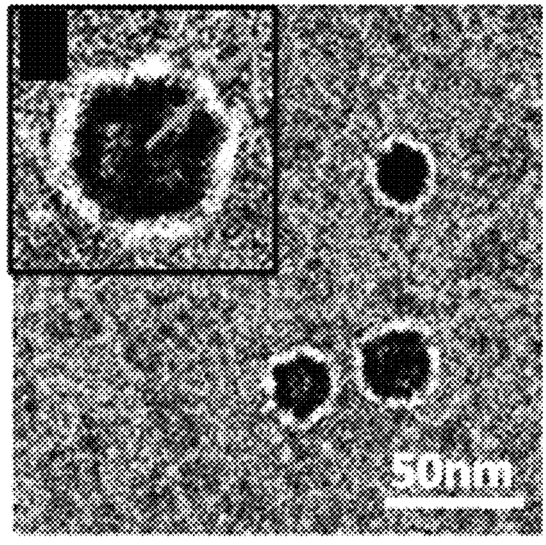
FIG. 12 is a TEM image illustrating the presence and thickness of a polymer coating on non-targeted magnetic nanoparticles.

To transfer hydrophobic MN coated with oleic acid to an aqueous phase, we encapsulated them into poly(ethylene glycol)-block-poly(ε-caprolactone) (PEG-PCL)-based nanocarriers by using the solvent evaporation approach (FIG. 11). PEG-PCL based nanocarriers are promising vehicles for systemic delivery of therapeutic and imaging agents due to high biocompatibility, biodegradability, long-circulation, and ease of conjugation by versatile coupling strategies. Cryo-TEM images demonstrated that MN are individually coated by PEG-PCL polymer and the thickness of the PEG-PCL layer is 3.6 nm (FIG. 12). Dynamic light scattering (DLS) analysis (FIG. 13) further demonstrates that PEG-PCL-coated MN have a hydrodynamic diameter of 30.5±11.1 nm with monodispersed size distribution (polydispersity index (PDI)=0.14), and a slightly negative charge (−1.31±0.19 mV). The inventors' have previously determined that after intravenous injection, dye-loaded PEG-PCL nanoparticles with similar parameters efficiently accumulate in endometriotic grafts via passive targeting, extravasate from blood vessels and penetrate endometriotic tissue (data not shown).

II. Preparation of Endometriosis-Targeted Magnetic Nanoparticles

Figure 13:
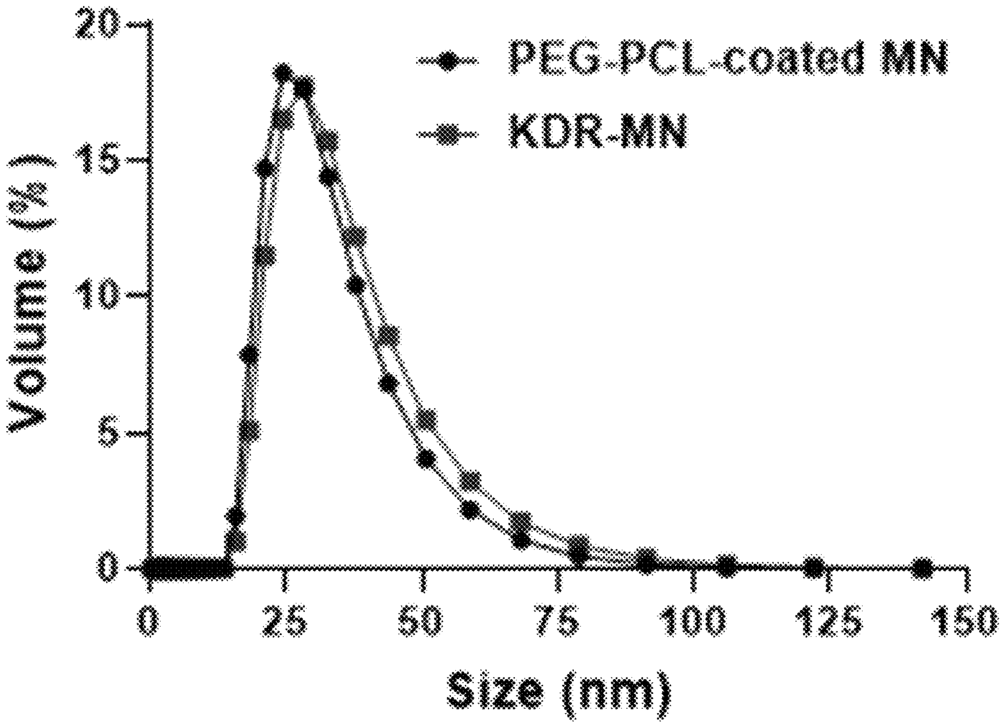
FIG. 13 is a graph of volume versus size, illustrating the dynamic light scattering profiles of non-targeted MN and KDR-targeted MN.
Figure 14:
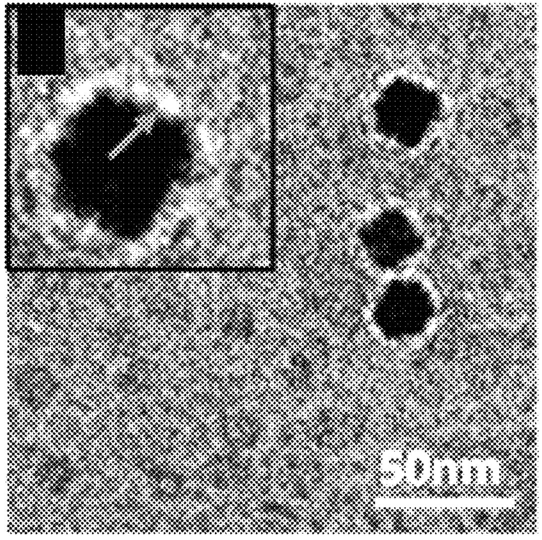
FIG. 14 is a TEM image illustrating the presence and thickness of a polymer coating on KDR-targeted magnetic nanoparticles.
Figure 15:
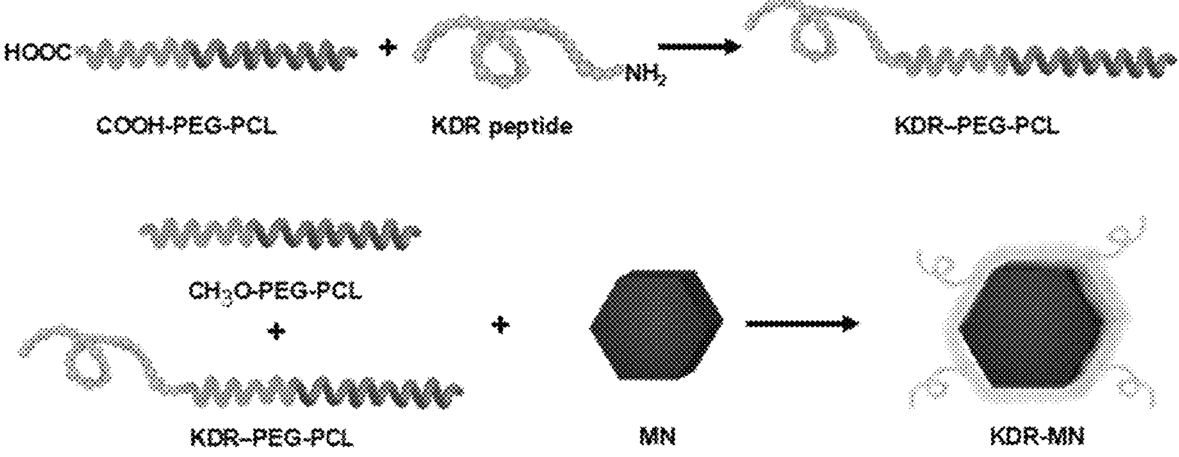
FIG. 15 is a schematic diagram illustrating one exemplary embodiment of how a targeted magnetic nanoparticle may be formed.

To enhance the accumulation and specificity of the PEG-PCL-coated MN for endometriotic cells, their surfaces were modified with peptides to target vascular endothelial growth factor receptor 2 (also known as KDR), that is overexpressed in endometriotic cells and minimally expressed or temporally restricted in other tissues. Heptapeptide (ATWLPPR; SEQ ID NO. 4) VEGFR/KDR antagonist was used as a targeting ligand, which demonstrated a high affinity for the KDR receptor. In the first step, carboxylic acid-terminated PEG-PCL was conjugated to this peptide by coupling the carboxylic group of PEG to the terminal amine group in the peptide sequence (FIG. 15). A quantitative fluorometric peptide assay validated that the KDR peptide was conjugated to the PEG-PCL polymer. In the second step, a mixture of the synthesized peptide-PEG-PCL and methoxy terminated PEG-PCL ($CH_3O$-PEG-PCL), used for the preparation of non-modified nanoparticles (FIGS. 11 and 12), was employed at ratio 1:9 to prepare KDR-targeted MN (KDR-MN, FIG. 15). DLS analysis revealed that an average hydrodynamic diameter of KDR-MN (33.5±13.6 nm, PDI=0.14) was 3 nm larger than non-targeted MN (30.5±11.1 nm, PDI=0.14) (FIG. 13). Zeta potential measurements demonstrated that both KDR-targeted MN (−1.47±0.32 mV) and non-targeted MN (−1.31±0.19 mV) had a slightly negative charge. Finally, cryo-TEM images indicate that KDR-MN were also individually coated by PEG-PCL polymer and the thickness of the PEG-PCL layer was similar to the non-targeted MN (FIG. 14).

III. In Vitro Evaluation of Cellular Uptake, Heating and Therapeutic Efficiency of Non-Targeted and KDR-Targeted MN.

Figure 16:
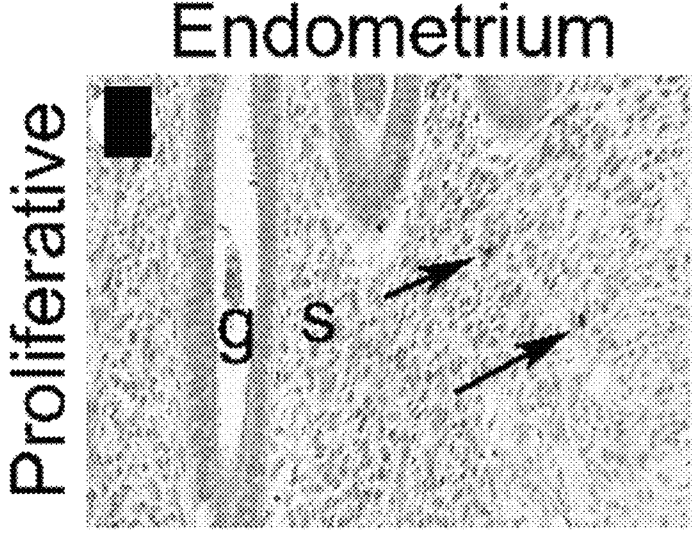
FIG. 16 is a digital image of macaque endometrium with immunostaining for KDR, illustrating that only vascular cells (arrows) show KDR staining in endometrium, with g indicating the gland.
Figure 17:
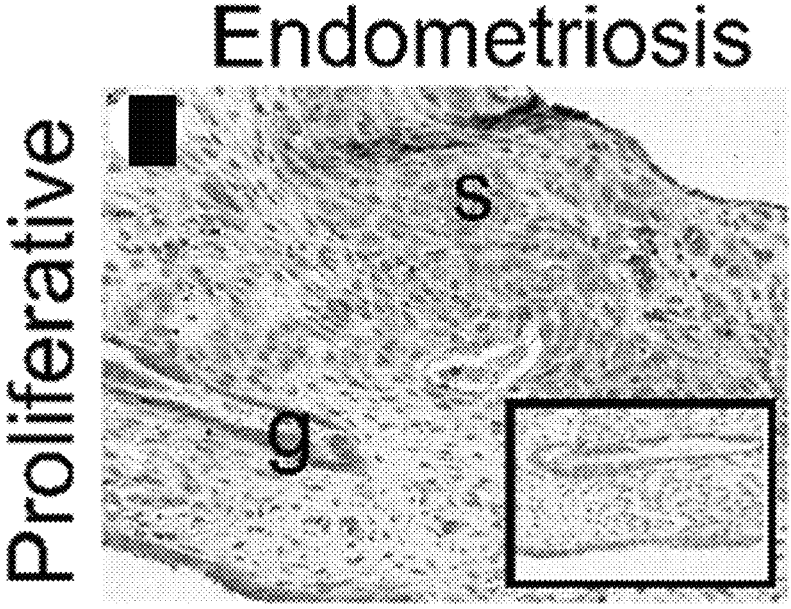
FIG. 17 is a digital image of macaque endometriosis with immunostaining for KDR, illustrating that KDR staining (brown) is stronger in stroma(S) in endometriosis, and with g indicating the gland, and the inset showning the negative control.
Figure 18:
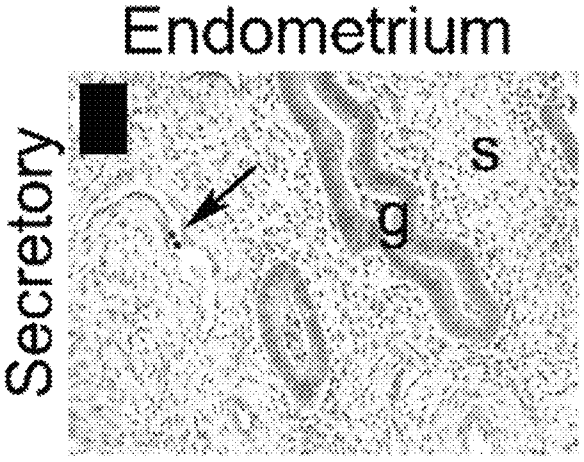
FIG. 18 is a digital image of macaque endometrium in secretory phase with immunostaining for KDR, illustrating that only vascular cells (arrows) show KDR staining in endometrium, with g indicating the gland.
Figure 19:
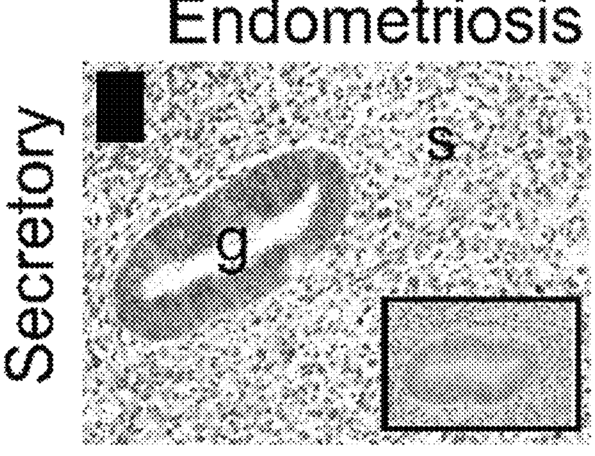
FIG. 19 is a digital image of macaque endometriosis with immunostaining for KDR, illustrating that KDR staining (brown) is stronger in stroma(S) in endometriosis, and with g indicating the gland, and the inset showning the negative control.
Figure 20:
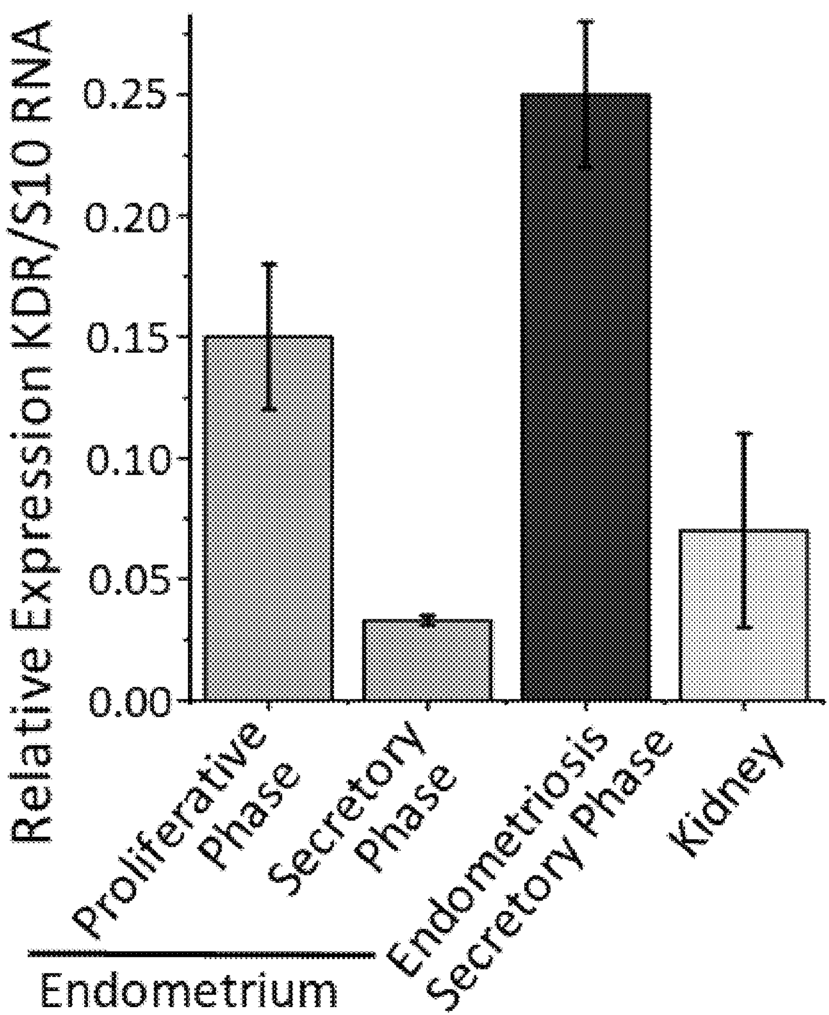
FIG. 20 is a graph of relative expression KDR/S10 RNA versus the tissue, illustrating the expression of KDR in macaque endometrium (proliferative and secretory phases), endometriosis (secretory phase), and kidneys, as determined by qPCR analysis.

The KDR receptor is known to play a pivotal role in the neovascularization of endometriosis. Previous reports and the inventors' results suggest that KDR expression levels are significantly higher in both human and macaque endometriosis lesions when compared to eutopic endometrium (FIGS. 16-20), while there was no significant difference of KDR expression in the eutopic endometrium between patients with endometriosis and healthy women. Hormonal regulation of KDR has been reported in the endometrium of women and macaques and was increased in the proliferative phase and reduced by progesterone in the secretory phase (FIGS. 16, 18 and 20). However, in endometriosis, KDR levels remained high throughout the cycle as a result of progesterone resistance in these tissues (FIGS. 17, 19 and 20). FIG. 20 also illustrates that KDR levels in macaque endometriosis lesions were about 10 times higher than endometrium tissue in the secretory phase. Thus, treatment with KDR-targeted nanoparticles in the late to mid luteal phase should minimize off-target effects on endometrium. The data also validate that KDR receptors are significantly overexpressed in endometriosis relative to organ tissues (e.g., kidney) (FIG. 20).

Figure 21:
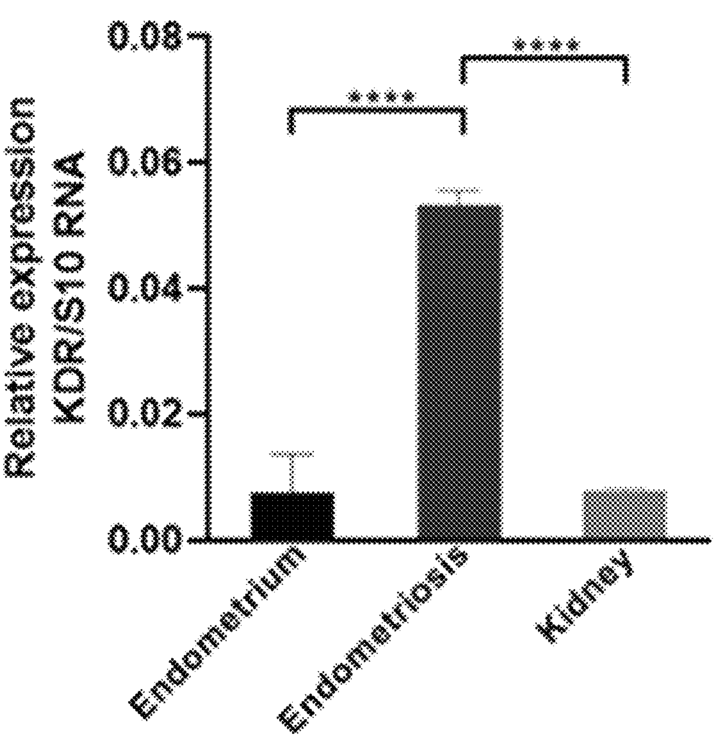
FIG. 21 is a graph illustrating the KDR mRNA expression in in macaque endometrium, endometriosis, and kidney cells, as determined by qPCR.
Figure 22:
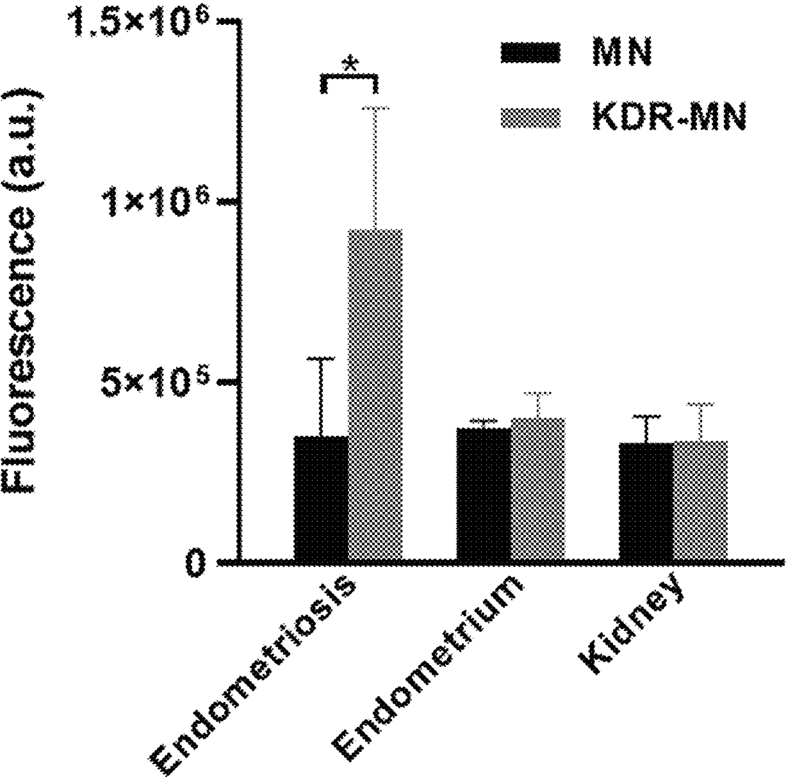
FIG. 22 is a graph of fluorescence versus cell type, illustrating flow cytometry analysis of cellular uptake of dye-labeled non-targeted (MN, black bar) and KDR-targeted magnetic nanoparticles (KDR-MN, red bar) by macaque endometriosis stroma cells, endometrium cells and kidney cells after 24 hours of incubation.

To evaluate the ability of KDR peptides to enhance internalization efficiency of MN into cells overexpressing KDR receptors, primary cells were isolated from macaque endometriosis lesions, endometrium and kidneys. qPCR analysis validated significantly higher KDR mRNA expression in cells isolated from macaque endometriotic lesions when compared to cells of normal endometrium (FIG. 21). Cultured cells were incubated for 24 hours with non-targeted and KDR-MN loaded with a fluorescent dye (Nile Red) and analyzed with flow cytometry. Flow cytometry results demonstrated that KDR peptide significantly enhanced nanoparticle uptake only into macaque endometriosis stromal cells, but not into endometrium and kidney cells (FIG. 22). The mean fluorescent intensity of endometriosis cells treated with KDR-targeted MN was 2.5 times higher when compared to non-modified nanoparticles (FIG. 22).

Figure 23:
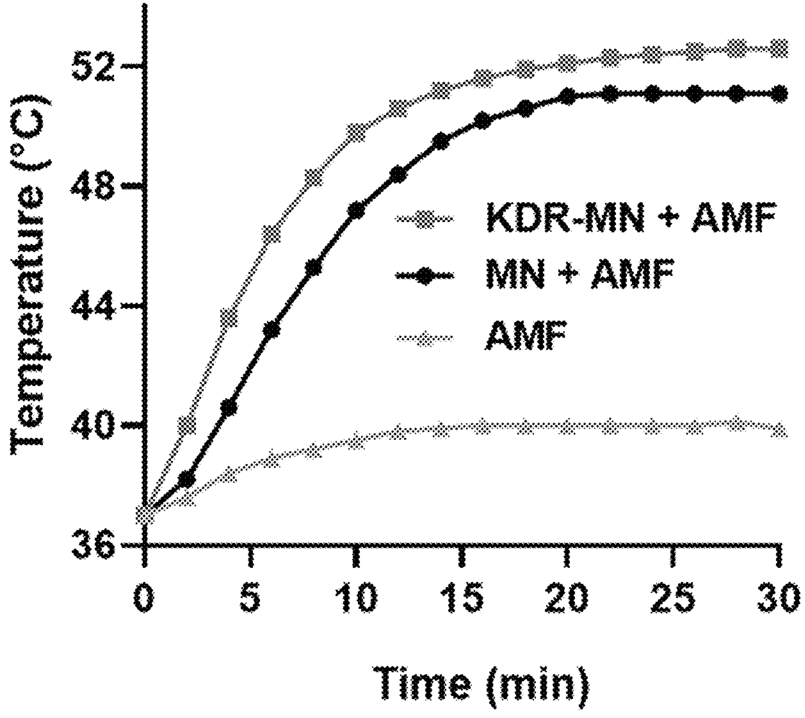
FIG. 23 is a graph of temperature versus time, illustrating representative heating profiles of endometriosis cells incubated with media only (AMF, gray curve), non-targeted MN (MN+AMF, black curve), and KDR targeted MN (KDR-MN+AMF, red curve) for 24 hours at the nanoparticle concentration of 25 μg Fe/mL and subjected to AMF (420 kHz, 26.9 kA/m) for 30 minutes.
Figure 24:
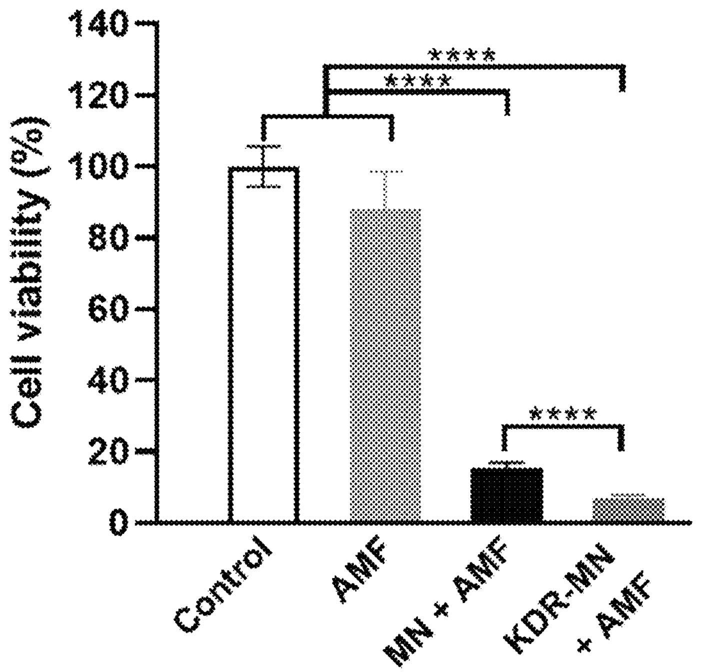
FIG. 24 is a graph of cell viability versus treatment, illustrating the viability of endometriosis cells after the treatments described in FIG. 23.

To compare the heating and therapeutic efficiency of both non-targeted and KDR-targeted MN in vitro, the pellets of macaque endometriosis cells incubated with the tested nanoparticles as described above were exposed to AMF (420 kHz; 26.9 kA/m) and the temperature changes were recorded with a fiber optic. The obtained temperature profiles revealed that due to the enhanced cellular uptake, KDR-MN exhibit superior cellular heating efficiency upon exposure to AMF than non-modified nanoparticles (FIG. 23). KDR-targeted MN increased cellular temperature from 37° C. to 52.6° C., reaching 42° C. inside the cell pellets within 190 seconds. In contrast, non-targeted nanoparticles raised the temperature of the cell pellets only up to 51° C., reaching 42° C. within 310 seconds under the same experimental conditions. Magnetic hyperthermia mediated by the non-targeted and KDR-MN decreased the viability of macaque endometriosis cells by 85% and 93%, respectively (FIG. 24). Of note, AMF exposure of cells only (without nanoparticles) resulted in negligible temperature changes and cell death (FIG. 24, gray bar).

IV. Endometriosis Mouse Model

The capacity for human and nonhuman primate tissues to grow in vivo in chimeric models of experimental endometriosis has proven to be useful for pre-clinical testing of novel therapies. Several laboratories have demonstrated that human and macaque endometrium as well as ectopic endometriosis can be transplanted into immunocompromised mice. Mouse strains previously employed for this purpose include athymic (nude) mice, Severe Combined Immunodeficient (SCID) mice, SCID beige mice and (Recombinant Activating Gene 2/rag2 null; Rag 2 null common cytokine receptor $\gamma$ chain ($\gamma$c) double null) mice. These mice lack a fully competent immune system with varying degress of immunodeficience associated with reduced or absence populations lymphocytes; therefore, do not mount an immune response against tissue xenografts. Importantly, experimental endometriosis can created using tissues obtained from subjects with and without endometriosis via endometrial biopsy, the collection of menstrual effluent or from laparoscopic surgical specimens. In each of these cases the resulting grafts display endometriotic stroma and glands similar to the clinical disease in women. To obtain the results described herein a model was used where rhesus macaque endometrium (or ectopic endometriosis) was engrafted into SCID mice. To induce cyclic growth of the engrafted primate tissues the mice were treated with hormone releasing pellets that produce human levels of E2 and progesterone (P4). In a typical experiment, mice were engrafted with endometrium or endometriotic tissue in mice treated with both E2 (90-day release) and P4 (14 day release). Then as P4 levels declined the tissues underwent a bleeding event similar to menstruation. This was followed by renewed angiogenesis similar to endometriotic lesions in both women and nonhuman primates. The xenografts were then allowed to grow for an additional 4-6 weeks with replacement of P-releacing pellets prior to further imaging studies. This artificial cycle treatment greatly reduced the effect of the initial graft surgery and acute inflammation on study outcomes.

V. In Vivo Evaluation of Nanoparticle-Mediated Magnetic Hyperthermia

Figure 25:
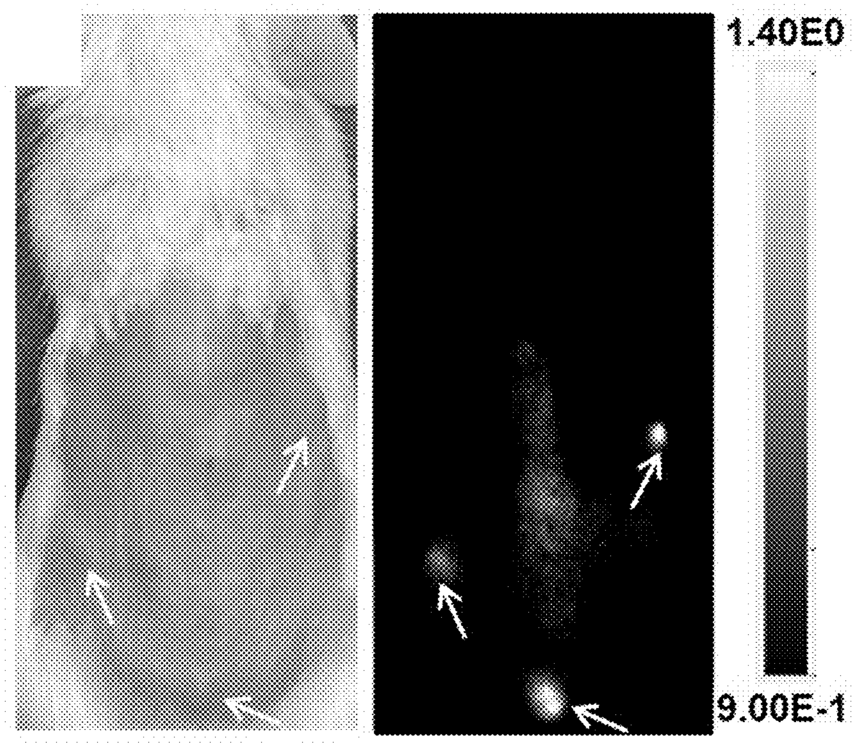
FIG. 25 provides digital image (left) and NIR fluorescence image (right) of a mouse bearing multiple endometriotic grafts (white arrows) at 5 days after IV injection of KDR targeted MN (3 mg Fe/kg) loaded with a NIR fluorescence dye (SiNc).
Figure 26:
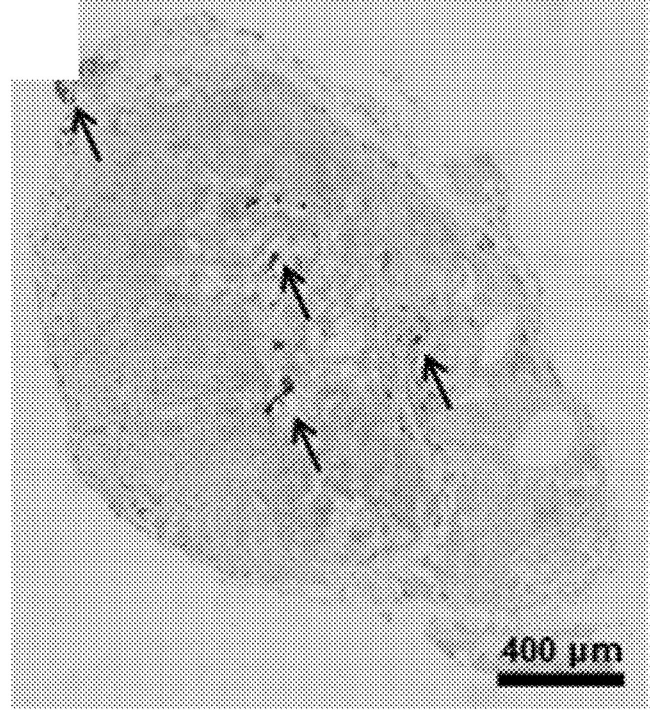
FIG. 26 is a digital image illustrating representative Prussian blue stained (black arrows) section of an endometriotic graft collected from a mouse at 5 days post-injection with KDR-MN.

To validate that the disclosed targeted nanoparticles efficiently accumulate in endometriotic lesions following systemic administration, mice bearing multiple grafts (FIG. 25) were IV injected with KDR-MN (3 mg Fe/kg) loaded with a NIR fluorescence dye (SiNc). The acquired images of mice revealed that a strong NIR fluorescence signal generated by the delivered SiNc is present in all endometriotic grafts (FIG. 25). To further confirm that PEG-PCL-based polymeric vehicles also delivered the developed iron oxide-based MN, endometriotic grafts were dissected and stained with Prussian blue used to detect iron. As shown in FIG. 26, Prussian blue staining was distributed throughout the endometriosis tissue from the edge to the center. These results demonstrated that systemically injected KDR-MN can efficiently reach the periphery of endometriotic grafts via passive targeting and penetrating their cores. The observed distribution of KDR-MN is an important criterion for homogeneous heating of endometriotic lesions and their efficient eradication. It has been widely recognized that the heterogeneous nanoparticle distribution within cancer tissues following intratumoral administration is an important issue for magnetic hyperthermia because it leads to the under-heating of regions within tumors.

Figure 27:
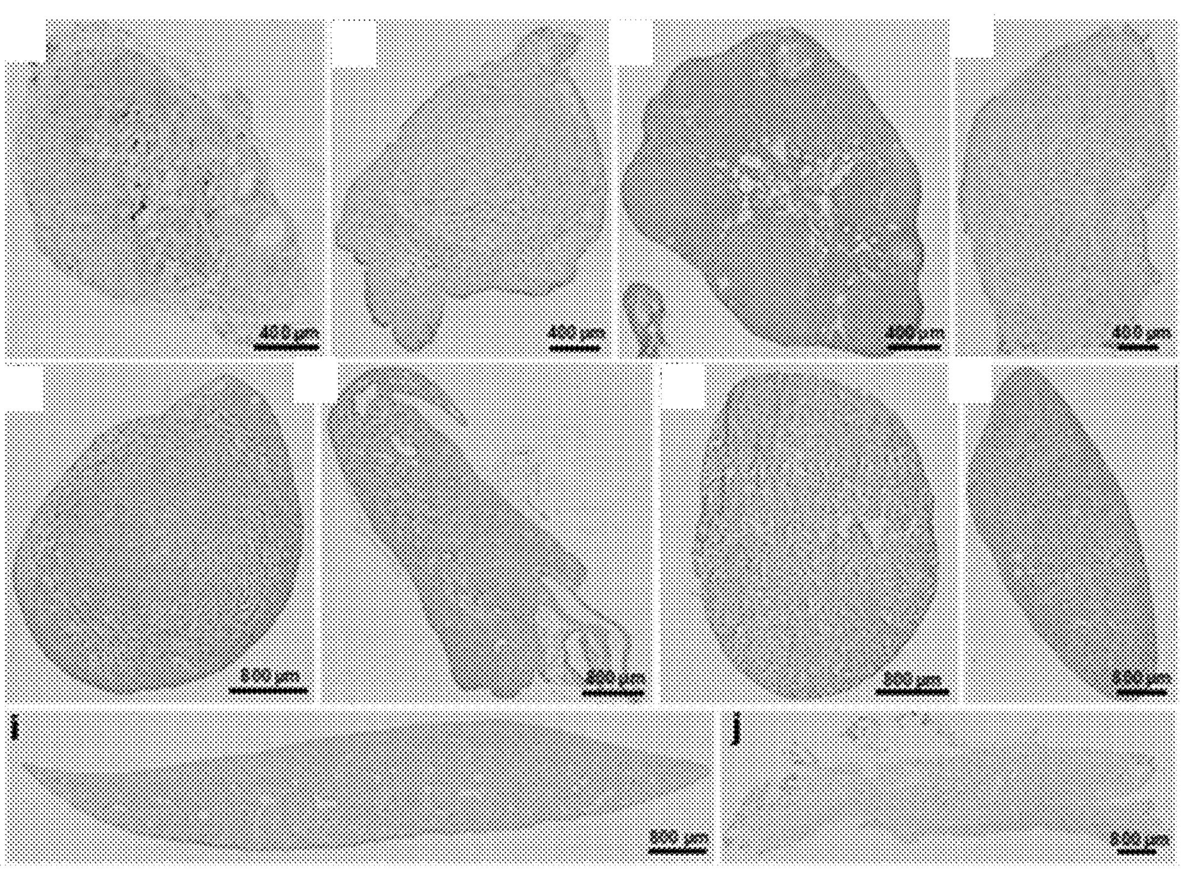
FIG. 27 provides digital images illustrating Prussian blue staining of sectioned tissues resected from mice bearing endometriotic grafts at 5 days after IV injection of KDR-MN (3 mg Fe/kg); from left to right, top row: Endometriotic graft; Uterus tract; Ovary; Bladder; middle row: Heart; Lung; Kidney; Spleen; bottom row: Liver; Tissue adjacent to a graft.

Microscopic analyses of Prussian blue-stained sections of various organs, including the uterus, revealed that systemically injected KDR-MN do not significantly accumulate in these tissues compared to the endometriosis grafts (FIG. 27). This demonstrated that during KDR-MN-mediated magnetic hyperthermia, potential collateral injury to the organs will be prevented.

Figure 28:
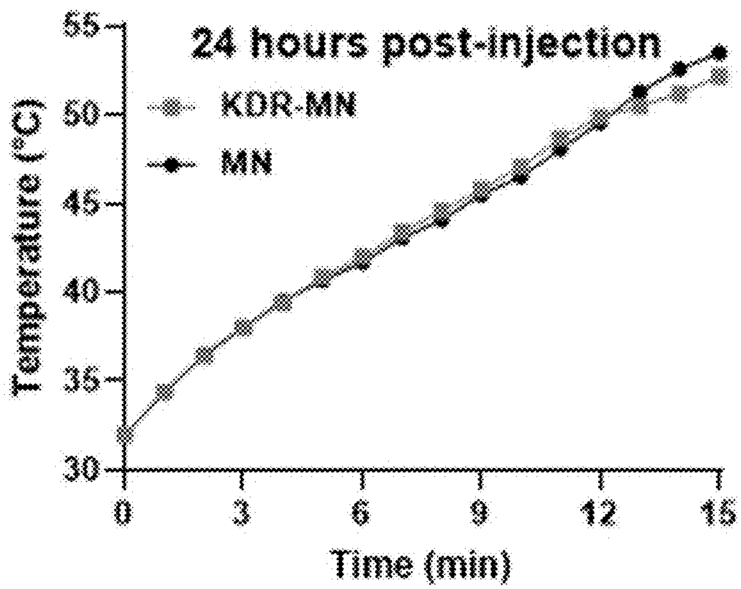
FIG. 28 is a graph of temperature versus time, illustrating the temperature profiles inside of endometriotic grafts during AMF (420 kHz, 26.9 kA/m) exposure at 24 hours after IV administration of non-targeted MN (3 mg Fe/kg) and KDR-MN (3 mg Fe/kg).
Figure 29:
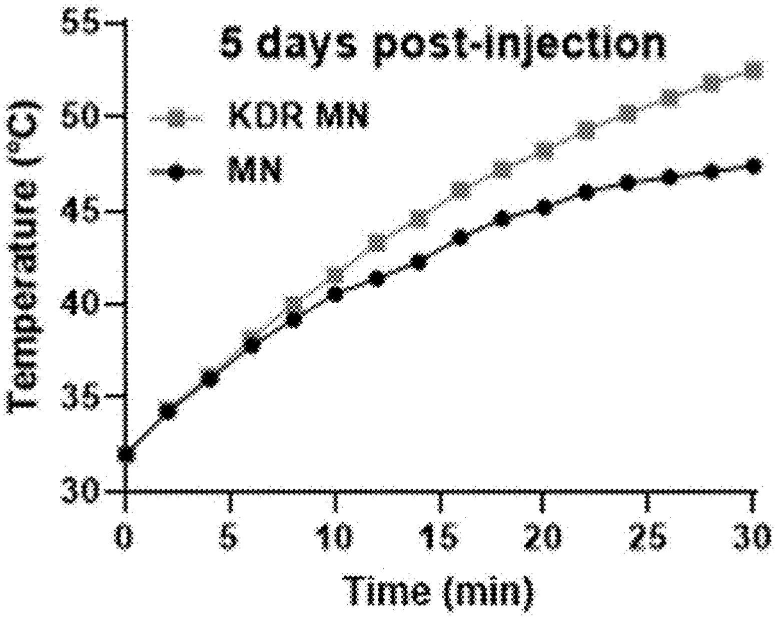
FIG. 29 is a graph of temperature versus time, illustrating the temperature profiles inside of endometriotic grafts during AMF (420 kHz, 26.9 kA/m) exposure at 5 days after IV administration of non-targeted MN (3 mg Fe/kg) and KDR-MN (3 mg Fe/kg).

In the next step, the ability of the systemically injected KDR-MN to generate heat in endometriotic grafts upon exposure to AMF (420 kHz; 26.9 kA/m) was evaluated. Temperature profiles were directly recorded using a fiber optic probe inserted into the grafts. The results demonstrated that 24 hours after IV injection at a low dose (3 mg Fe/kg), the KDR-MN rapidly increased the temperature inside of endometriotic grafts up to 52° C., reaching 42° C. within 6 minutes (FIG. 28, red curve, square data points). Furthermore, the acquired data demonstrate that even 5 days post-injection of the KDR-MN, a similar therapeutic temperature (52° C.) was attained in endometriotic tissue (FIG. 29, red curve, square data points). The ability of the KDR-MN to be retained in endometriotic tissue and generate the desirable therapeutic temperature for 5 days provided a long temporal window in which AMF can be applied and magnetic hyperthermia can be performed. It also enabled several sessions of magnetic hyperthermia to be performed during 5 days without the requirement for multiple nanoparticle injections.

The results suggested that KDR targeting significantly contributed to the ability of the developed nanoparticles to generate similar therapeutic temperatures during a 5-day time frame. FIG. 28 demonstrated that at 24 hours after injection, non-targeted and KDR-targeted nanoparticles had comparable heating profiles in endometriotic grafts, implying that both nanoparticles efficiently accumulate in endometriotic tissue via passive targeting within this period. However, only KDR-MN were able to elevate temperature in endometriotic grafts to 52° C. at 5 days post-injection (FIG. 29, red curve, square data points). In contrast, non-targeted MN raised the temperature to 47.4° C. under the same experimental conditions (FIG. 29, black curve, circle data points). Without being bound to a particular theory, the observed difference in heating profiles may be associated with increased retention of passively accumulated KDR-MN in endometriosis grafts compared to non-targeted MN. This was consistent with prior work showing that targeting ligands (e.g., KDR peptides) improve the internalization of passively delivered nanoparticles by cells expressing target receptors (e.g., VEGFR 2/KDR), resulting in their enhanced retention at disease sites (e.g., cancer or endometriosis) (data not shown). The results disclosed herein validated that the KDR peptide significantly increased MN uptake into the endometriotic stromal cells (FIG. 22).

Figure 30:
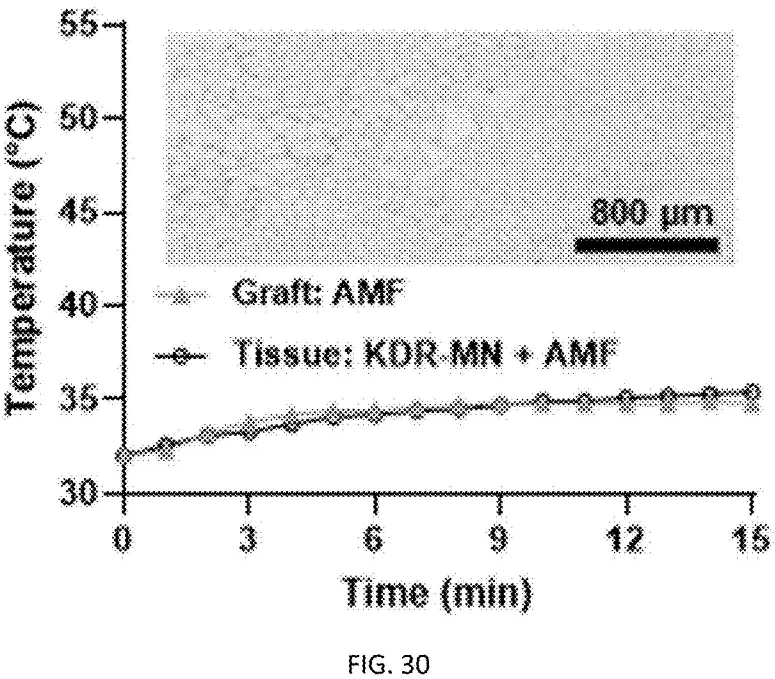
FIG. 30 is a graph of temperature versus time, illustrating the temperature profiles of an endometriotic graft (grey curve (triangles), graft: AMF) and tissue adjacent to a graft (black curve (circles), Tissue: KDR-MN+AMF), where prior to AMF exposure, mice were IV injected with a single dose of saline (AMF), or KDR-MN (3 mg Fe/kg), and then were exposed to AMF (420 kHz, 26 kA/m) at 5 days post-injection. Inset: Prussian blue staining of tissue adjacent to a graft resected from a mouse 5 days post-injection with KDR-MN.

The obtained data highlighted the superior in vivo heating efficiency of the developed KDR-MN compared to previously developed magnetic nanoparticles. For example, iron oxide nanoparticles co-doped with both manganese and cobalt could elevate the temperature of cancer tumors only up to 44° C. after intravenous injection and this intratumoral temperature can only be achieved at a higher dose (6 mg Fe/kg) (Albarqi, et al., *ACS Nano* 2019, 13, 6, 6383-6395). Importantly, the present results demonstrated that the increase in temperature of tissue immediately surrounding endometriotic grafts was negligible (FIG. 30, black curve (circles)) and was similar to the temperature increase in a graft exposed to AMF alone (no KDR-MN, (FIG. 30, gray curve (triangles)). The results suggested that systemically injected KDR-MN efficiently localized in endometriotic grafts, but not in tissue adjacent to the grafts (FIG. 30, inset and FIG. 27, bottom row, right) and heat transfer from a graft to the adjacent tissue is negligible. Moreover, the results validated that the employed AMF was safe because it significantly heated only tissues containing nanoparticles (FIGS. 29 and 30, black curve). The main requirement for AMF during magnetic hyperthermia is to minimize non-specific heating in tissue due to eddy currents generated by the AMF alone.

Figures 31, 32:
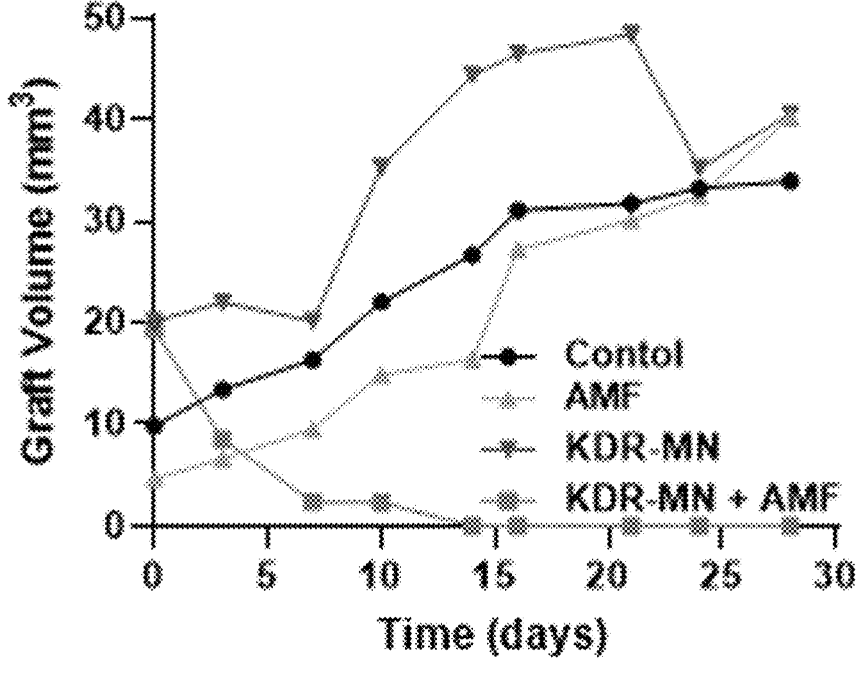
FIG. 31 is a graph of graft volume versus time, illustrating growth profiles of endometriotic grafts after the following treatments: (i) Control: mice were IV injected with saline; (ii) AMF: mice were IV injected with saline and exposed to AMF (420 kHz, 26 kA/m) for 20 minutes at 5 days post-injection; (iii) KDR-MN: mice were IV injected with KDR-MN (3 mg Fe/kg); (iv) KDR-MN+AMF: mice were IV injected with KDR-MN (3 mg Fe/kg) and exposed to AMF (420 kHz, 26 kA/m) for 20 minutes at 5 days post-injection.
FIG. 32 is digital images of a mouse bearing two macaque endometriotic grafts before, and 23 and 32 days (no skin) after treatment with one cycle of magnetic hyperthermia, after the mouse was injected intravenously with KDR-MN (3 mg Fe/kg) and with only lesion #1 being exposed to AMF (420 kHz, 26 kA/m) for 20 minutes on day 5 post-injection.

It was then validated that the endometriotic tissues in mice, intravenously injected with KDR-MN (3 mg Fe/kg) were completely eradicated after 20 minutes of exposure to AMF (420 kHz; 26.9 kA/m) at day 5 post-administration, with no recurrence (FIG. 31, red curve, squares). In contrast, endometriotic grafts were not affected by KDR-MN (FIG. 31, blue curve point down triangles) or AMF exposure alone (FIG. 31, gray curve, point up triangles), and these lesions had a similar growth tendency to the non-treated grafts (FIG. 31, black curve, circles).

Advantageously, the disclosed systemically delivered magnetic hyperthermia allow accurate lesion targeting because it selectively heats disease tissues with non-toxic nanoparticles, which are specifically activated by targeted non-toxic AMF. The focused AMF can be delivered to lesions, preventing the potential heating of normal tissues containing nanoparticles. The results show that by using focused AMF, it was possible to eradicate targeted endometriotic grafts without affecting nearby grafts containing KDR-MN (7 mm distance) in the same mouse (FIG. 32). The goal in this project was to develop nanoparticles for systemic delivery to endometriotic lesions that can be heated by currently available and future optimized magnetic hyperthermia systems.

Figure 33:
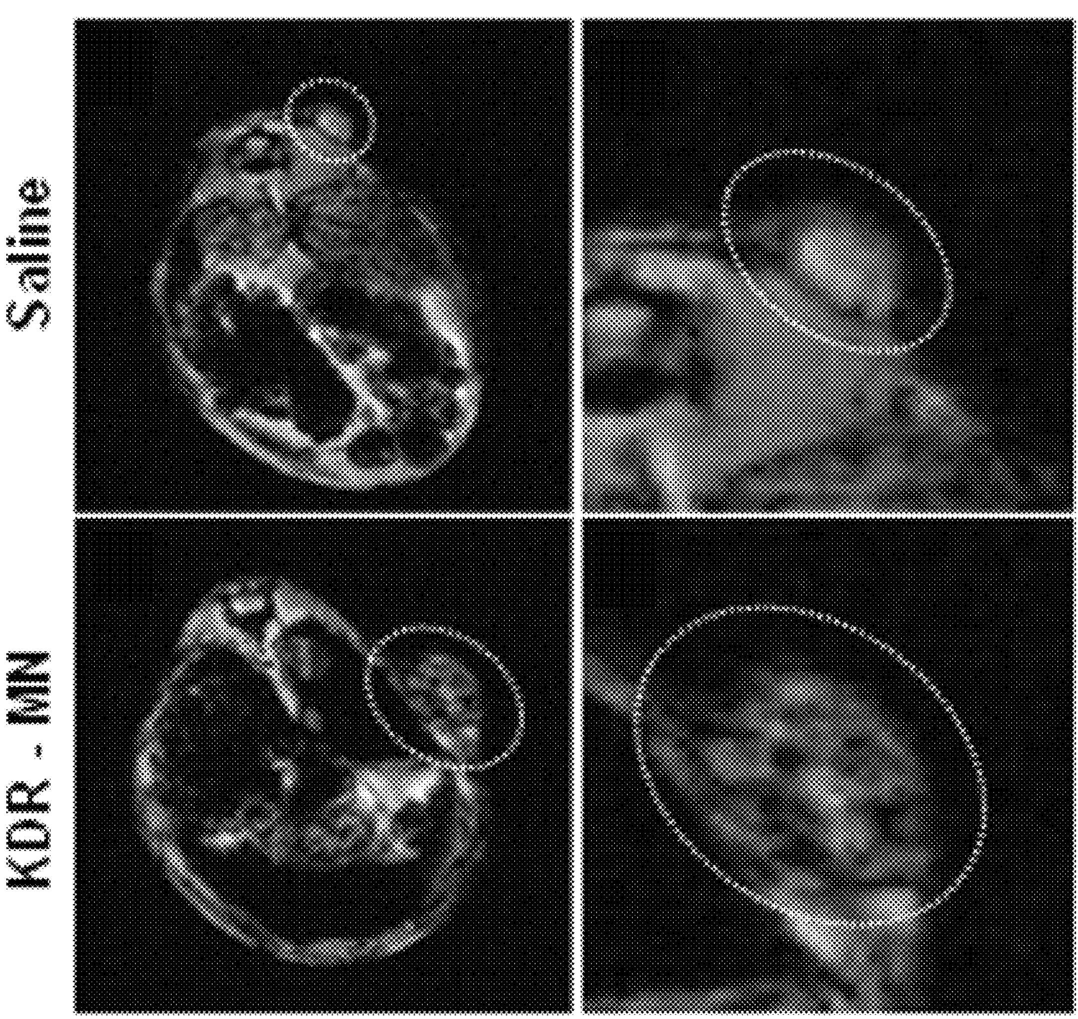
FIG. 33 is digital images of T2-weighted magnetic resonance images (MRI at TE 4.5 ms) that were obtained after 24 hours in mice injected intravenously with (top row) Saline and (bottom row) KDR-MN (3 mg Fe/kg) with the right side images being magnified images of the left side images.

In vivo studies also revealed the proof of concept of the disclosed KDR-MN as a molecular imaging agent in MRI to detect endometriosis grafts. FIG. 33 demonstrates representative T2-weighted MR images of endometriotic grafts in mice injected with saline and KDR-MN, respectively. A dashed circle depicts the graft area of each mouse. The acquired images demonstrate significant T2 signal dropout from the dephasing paramagnetic properties of KDR-MN in endometriotic grafts relative to the un-injected control at the concentration (3 mg Fe/kg) relevant for therapeutic hyperthermia. Therefore, these results demonstrate that MRI can be used before magnetic hyperthermia as a molecular imaging agent to detect the location of endometriotic lesions containing KDR-MN before focused AMF.

Figure 34:
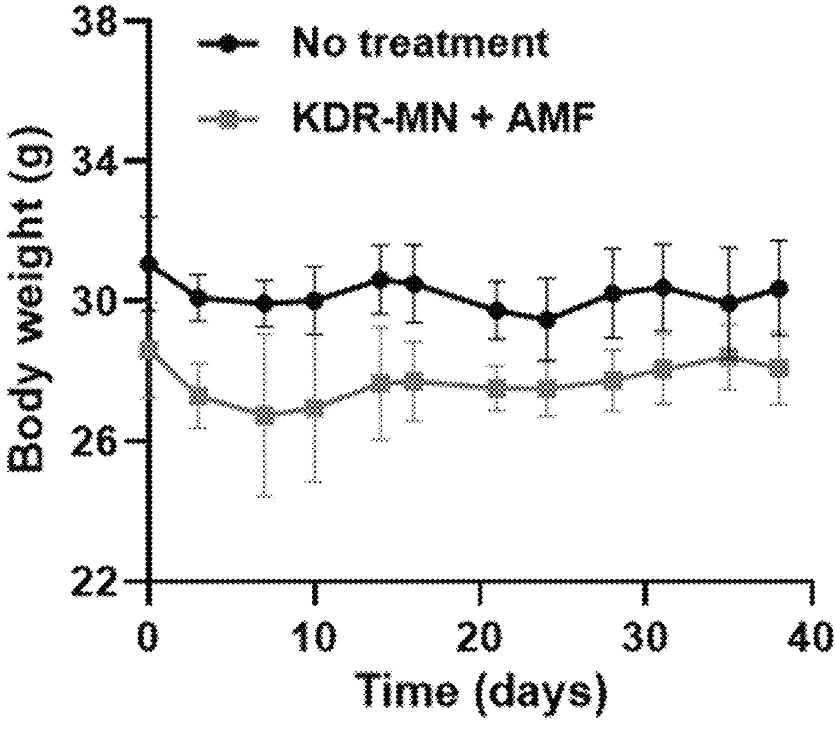
FIG. 34 is a graph of body weight versus time, illustrating the changes in body weights of non-treated mice (injected with saline) and mice exposed to magnetic hyperthermia (KDR-MN+AMF).
Figure 35:
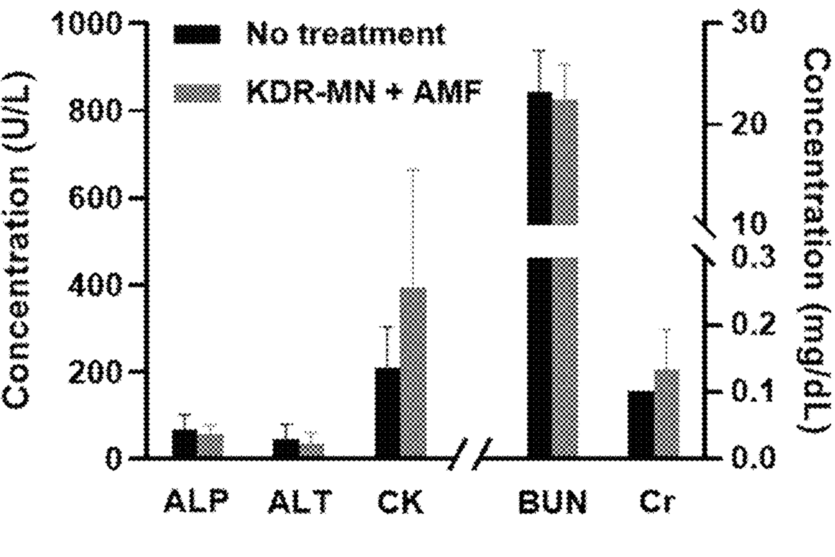
FIG. 35 is a graph of concentration versus biochemical marker, illustrating serum levels of biomarkers (alkaline phosphatase (ALP), aminotransferase (ALT), creatine kinase (CK), blood urea nitrogen (BUN), and creatinine (Cr)) in serum samples collected 42 days after treatment from non-treated mice and mice exposed to the magnetic hyperthermia.
Figure 36:
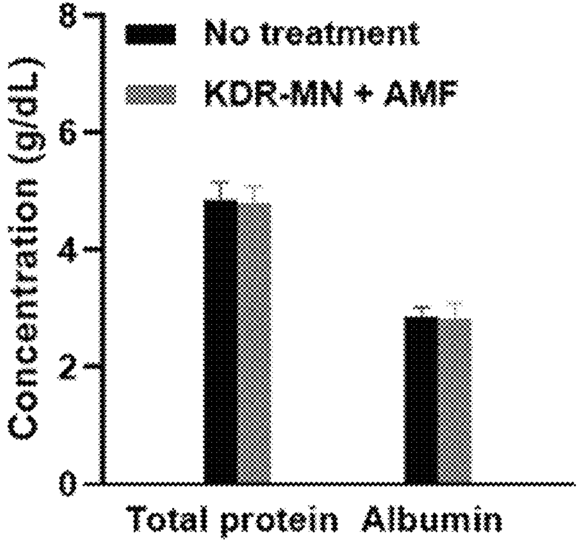
FIG. 36 is a graph of concentration versus biochemical marker, illustrating serum levels of total proetin and albumin in serum samples collected 42 days after treatment from non-treated mice and mice exposed to the magnetic hyperthermia.
Figure 37:
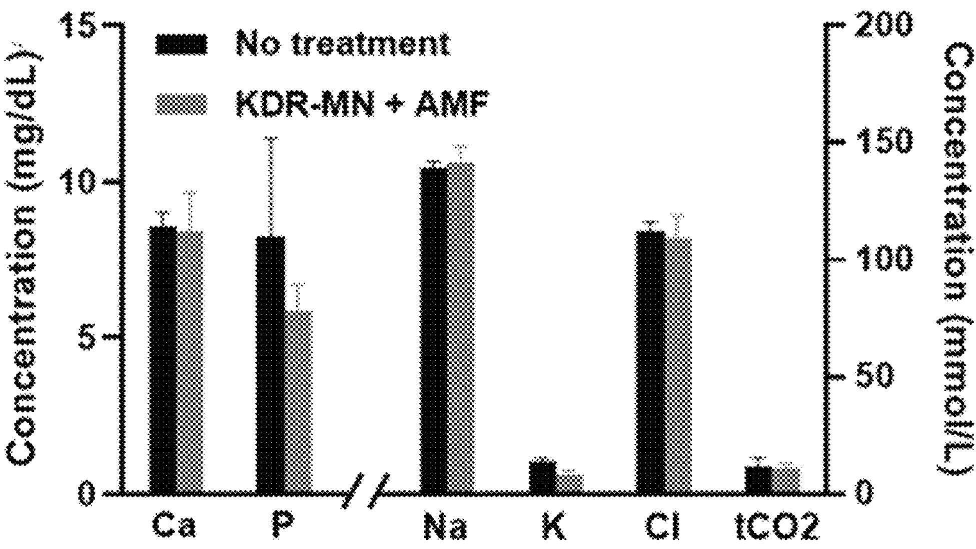
FIG. 37 is a graph of concentration versus biochemical marker, illustrating serum levels of blood electrolytes in serum samples collected 42 days after treatment from non-treated mice and mice exposed to the magnetic hyperthermia.

The results demonstrate that the KDR-MN-based magnetic hyperthermia is a safe therapy without noticeable adverse effects. None of the treated mice lost more than 10% of their body weight (FIG. 34), died, or exhibited any signs of toxicity during a 42-day study. The biochemical markers for the kidney function (blood urea nitrogen (BUN) and creatinine (Cr)), liver function (alanine aminotransferase (ALT), and alkaline phosphatase (ALP)), muscle and heart function (creatine kinase), as well as protein and electrolyte serum levels, were measured 42 days after the treatment (FIG. 35-37). All treated mice demonstrated normal serum biochemical values in comparison to control animals.

Conclusion

This study developed a novel non-surgical therapy named systemically delivered magnetic hyperthermia for safe and efficient eradication of endometriotic lesions. To realize the full potential of this treatment modality, novel endometriosis-targeted magnetic nanoparticles were engineered, that are capable of (i) efficient accumulation in endometriotic lesions following a single IV injection at a low dose (3 mg Fe/kg) and (ii) generation of therapeutic temperatures (>50° C.) in these lesions upon exposure to safe AMF. In vivo studies in mice bearing macaque endometriosis grafts validate that the developed nanoparticle completely ablate endometriotic grafts without adverse effects after a single 20-minute exposure to AMF. Furthermore, these nanoparticles demonstrated the potential to be employed as an MRI contrast agent to aid in the diagnosis of endometriotic lesions before AMF exposure. The obtained results suggested that nanoparticle-mediated magnetic hyperthermia can potentially provide an efficient non-surgical approach to eradicate endometriotic lesions and shift the paradigm for endometriosis treatment.

Example 4

Figure 38:
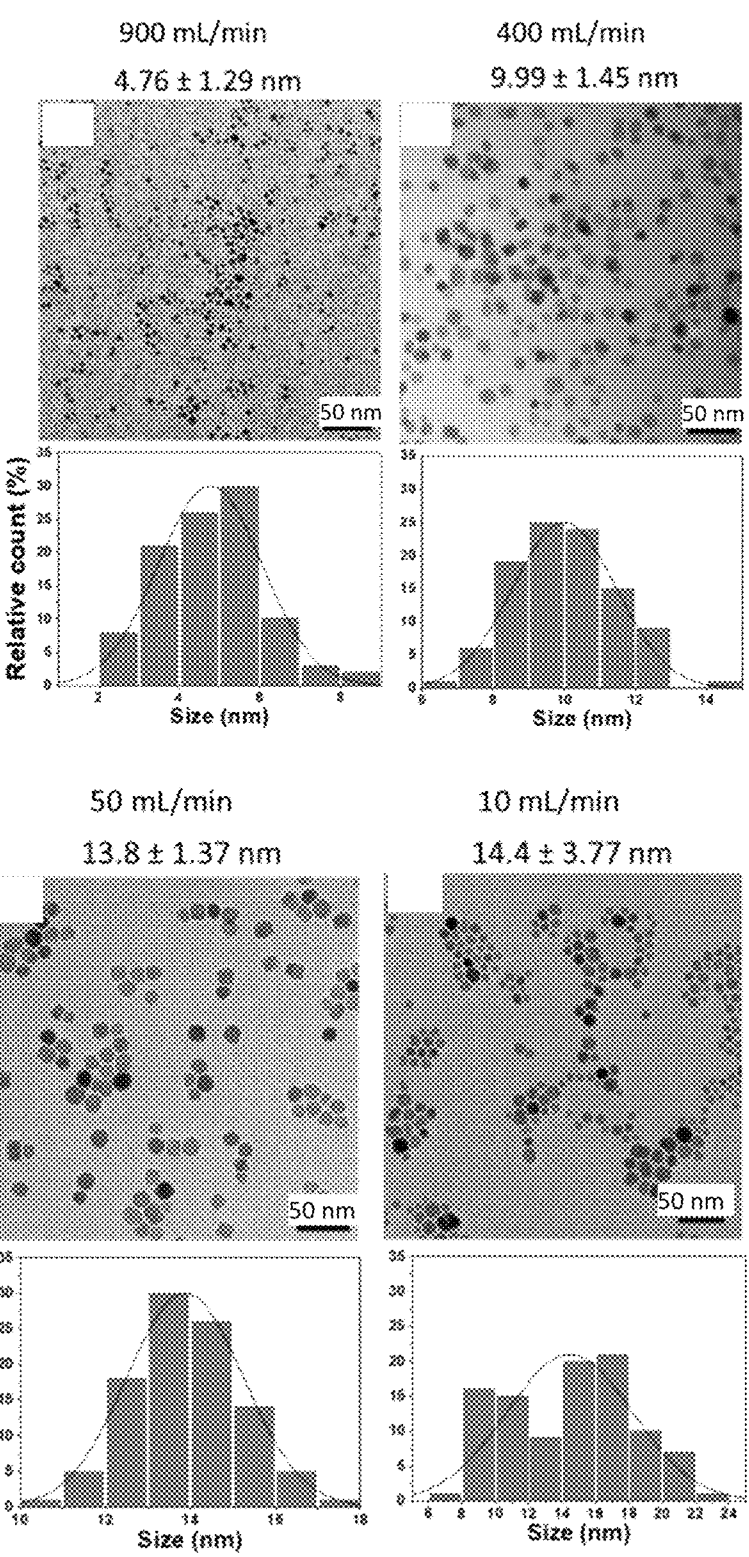
FIG. 38 provides TEM images of Co-IONPs synthesized at nitrogen flow rates of 900 mL/min, 400 mL/min, 50 mL/min and 10 mL/min, and their corresponding size distribution histograms.

Cobalt doped nanoparticles were prepared using four different amount of nitrogen input during synthesis (900, 400, 50, and 10 ml/min), in which the least nitrogen input allows for increased oxygen presence in the system than the highest nitrogen input. Hexagonal shaped iron oxide nanoparticles were synthesized to investigate the influence of inert gas flow rate on the nanoparticles (FIG. 38). Based on TEM imaging, the average diameter of Co-IONPs synthesized at 900, 400, 50, and 10 ml/min of $N_2$ flow rate was 4.76±1.29 nm, 9.99±1.45 nm, 13.8±1.37 nm, and 14.4±3.77 nm respectively with an overall irregular hexagonal shape (FIG. 38). In this measurement, the longest distance between two opposite vertices of the irregular hexagon was used to determine the size of Co-IONP.

Figure 39:
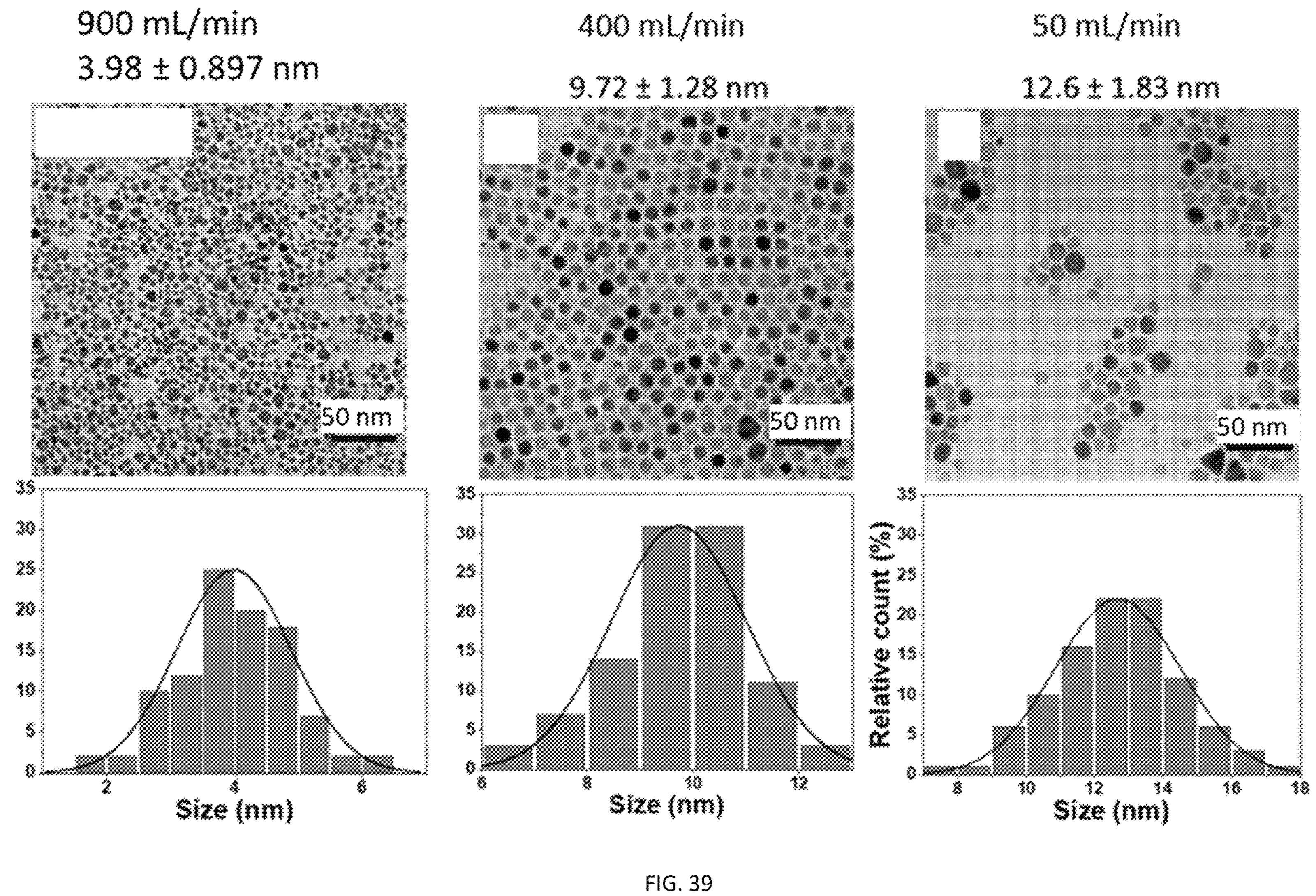
FIG. 39 provides TEM images of un-doped iron oxide nanoparticles synthesized at nitrogen flow rates of 900 mL/min, 400 mL/min, and 50 mL/min, and their corresponding size distribution histograms.
Figure 40:
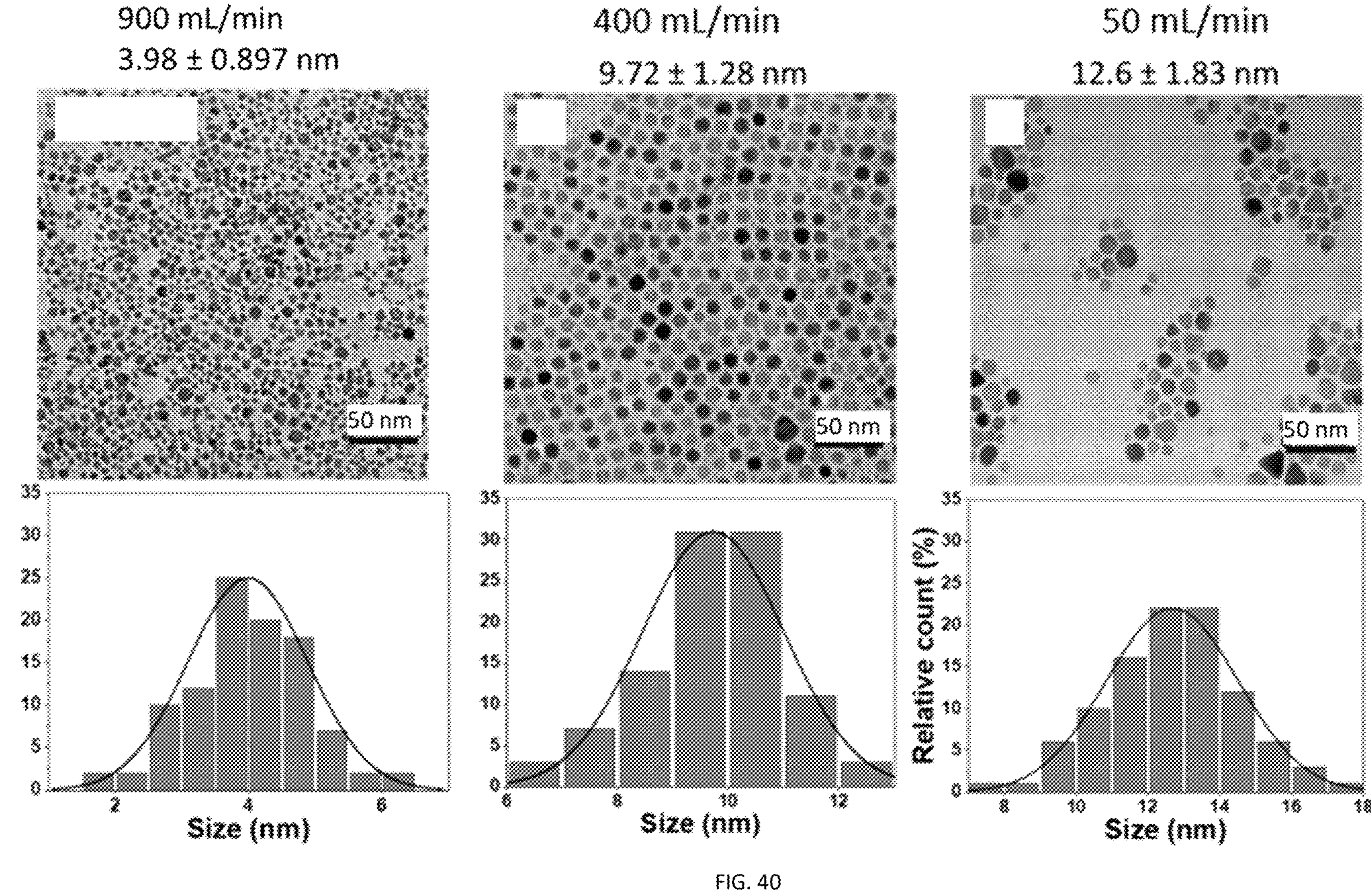
FIG. 40 provides TEM images of Nickel doped iron oxide nanoparticles synthesized at nitrogen flow rates of 900 mL/min, 400 mL/min, and 50 mL/min, and their corresponding size distribution histograms.

FIG. 38 also demonstrates that the size of nanoparticles was increased gradually from 5 nm to 14 nm by lowering the nitrogen flow rate into the system without any post-synthesis modifications. To test the generality of this trend, undoped (FIG. 39) and nickel doped (FIG. 40) iron oxide nanoparticles were synthesized in the same way. These nanoparticles likewise had an irregular hexagonal shape, and TEM imaging revealed that the average size of nanoparticles synthesized at 900, 400, and 50 ml/min of nitrogen flow rate increased as the nitrogen flow rate decreased (FIGS. 39 and 40).

Figure 41:
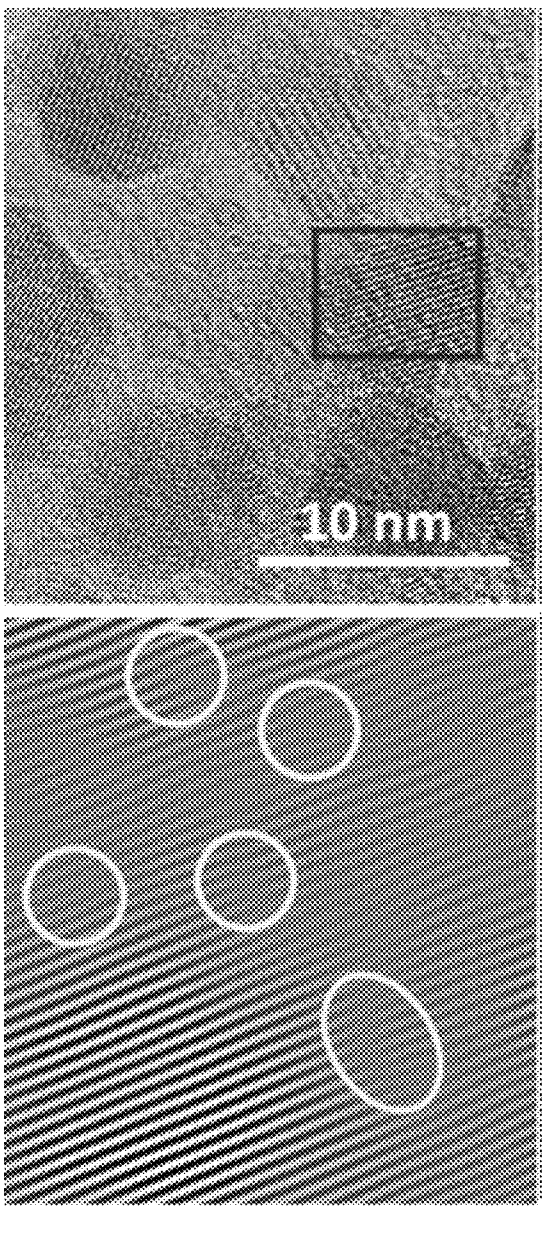
FIG. 41 provides a high-resolution TEM (HRTEM) image and the inverse FFT lattice fringe image of the highlighted area of exemplary Cobalt doped iron oxide nanoparticles synthesized at 900 mL/min nitrogen flow rate.
Figure 42:
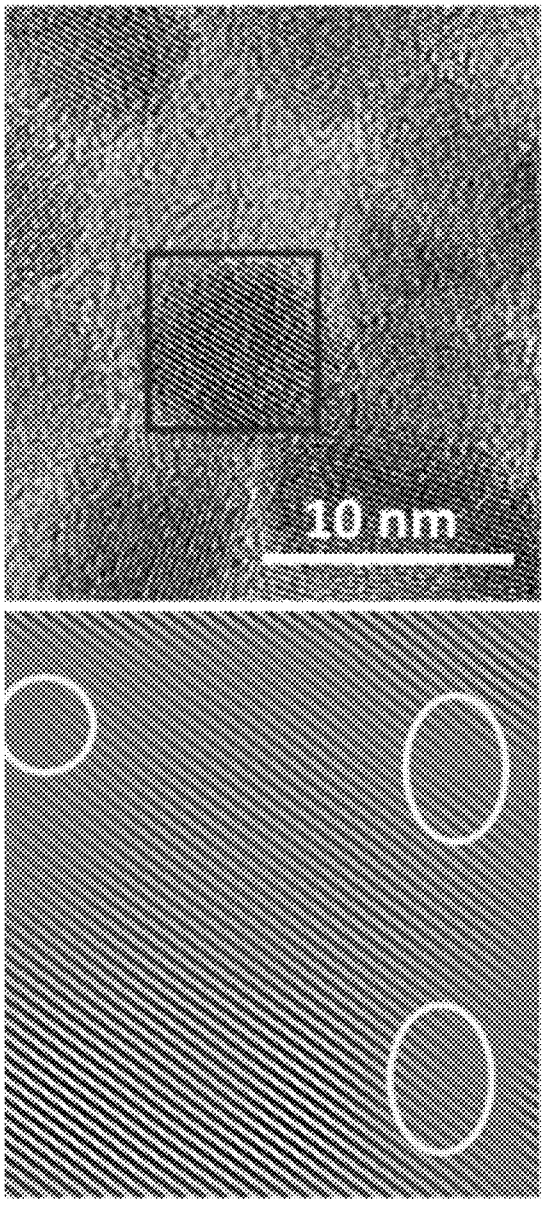
FIG. 42 provides a high-resolution TEM (HRTEM) image and the inverse FFT lattice fringe image of the highlighted area of exemplary Cobalt doped iron oxide nanoparticles synthesized at 400 mL/min nitrogen flow rate.
Figure 43:
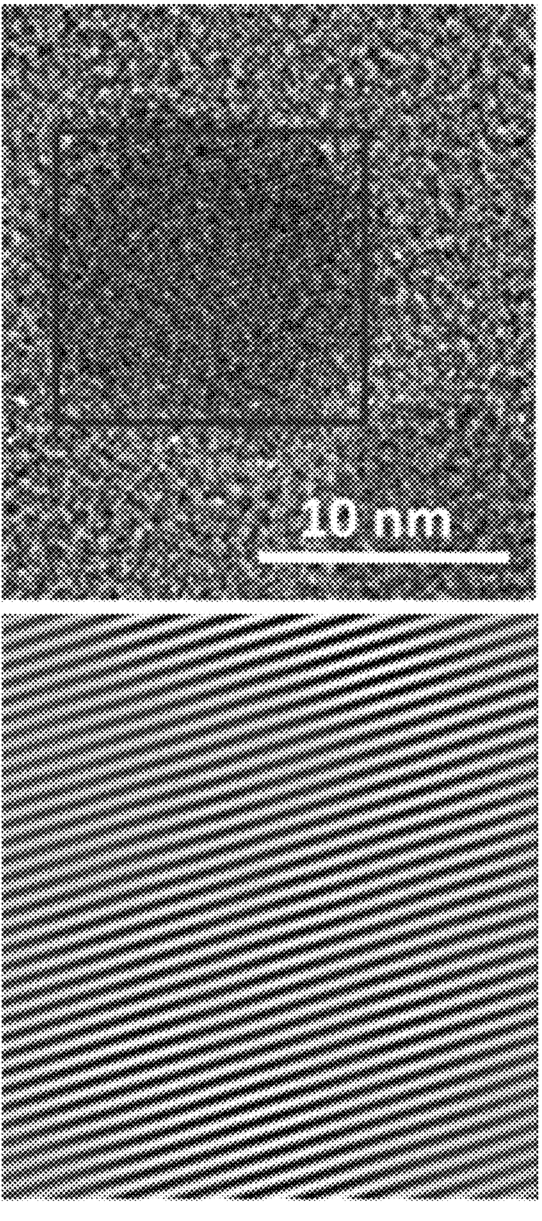
FIG. 43 provides a high-resolution TEM (HRTEM) image and the inverse FFT lattice fringe image of the highlighted area of exemplary Cobalt doped iron oxide nanoparticles synthesized at 50 mL/min nitrogen flow rate.
Figure 44:
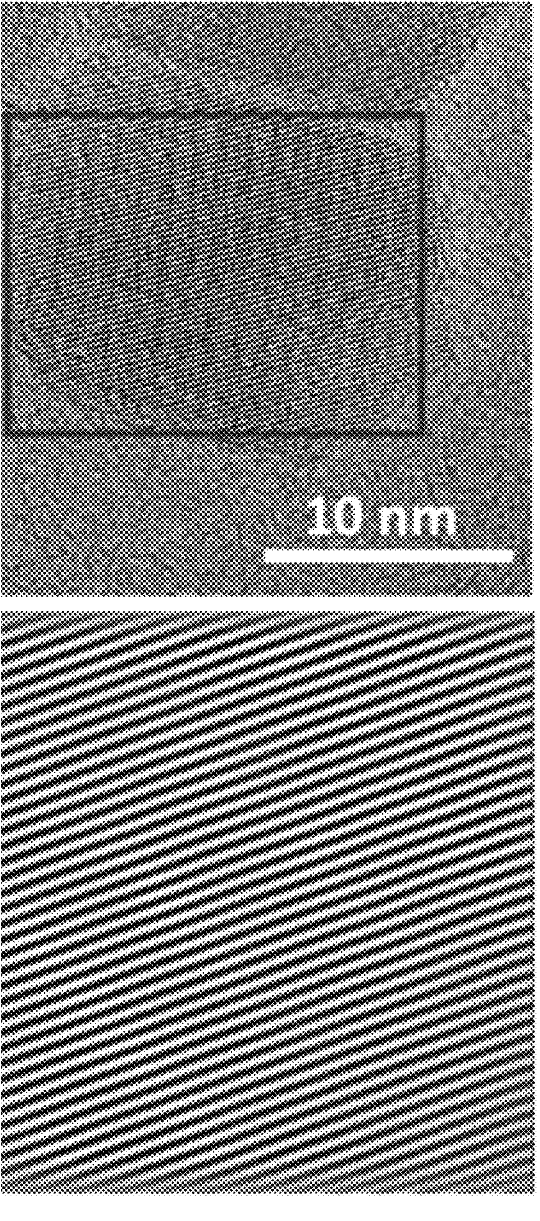
FIG. 44 provides a high-resolution TEM (HRTEM) image and the inverse FFT lattice fringe image of the highlighted area of exemplary Cobalt doped iron oxide nanoparticles synthesized at 10 mL/min nitrogen flow rate.

Next, internal crystal flaws in Co-IONPs were investigated further using a high-resolution TEM (HRTEM) (FIGS. 41-44). At first glance, the lattice fringes of all Co-IONPs appear to stretch across the entire particle in HRTEM images (FIGS. 41-44 upper image). However, Co-IONPs synthesized in 400 ml/min and 900 ml/min nitrogen flow rates were shown to poses evident lattice fringe defects in inverse Fourier transform (I-FFT) studies (FIGS. 41 and 42 lower image). These kind of crystalline defects have been shown to influence the nanoparticles' magnetic and hyperthermia related functional properties. The defect concentration observed in the 900 ml/min $N_2$ flow rate nanoparticles was observably higher than that of 400 ml/min $N_2$ flow rate nanoparticles as indicated in the images. On the other hand, nanoparticles synthesized under 50 ml/min and 10 ml/min $N_2$ flow rates did not show any crystal lattice defects in I-FFT studies (FIGS. 43 and 44 lower images). Therefore, low nitrogen input was used for the rest of the investigation.

Figure 47:
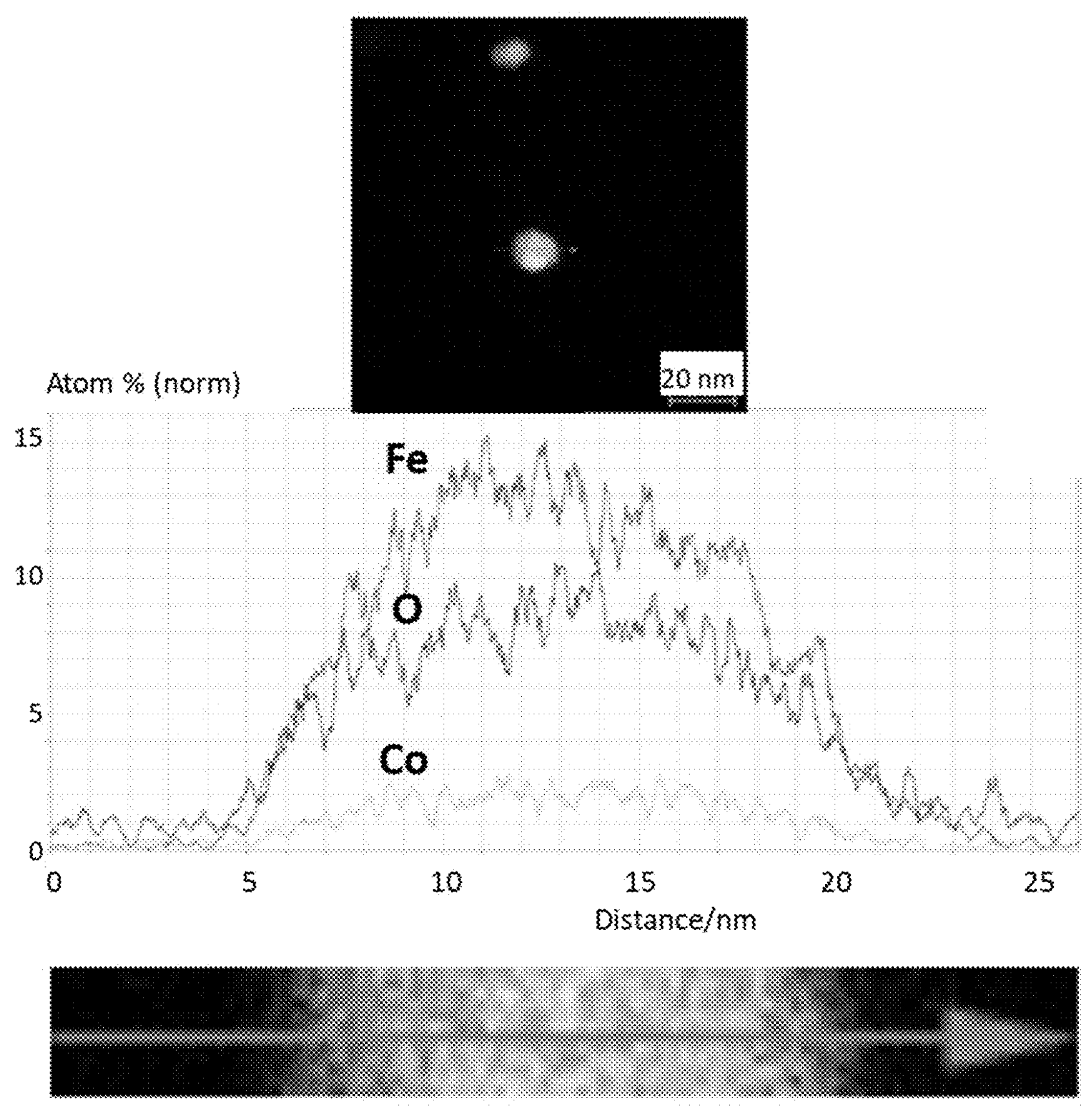
FIG. 47 is an energy-dispersive X-ray spectroscopy (EDX) line scan of the distribution of Cobalt, iron and oxygen through the synthesized 14 nm (1st layer) Co-IONPs under low nitrogen flow.
Figure 48:
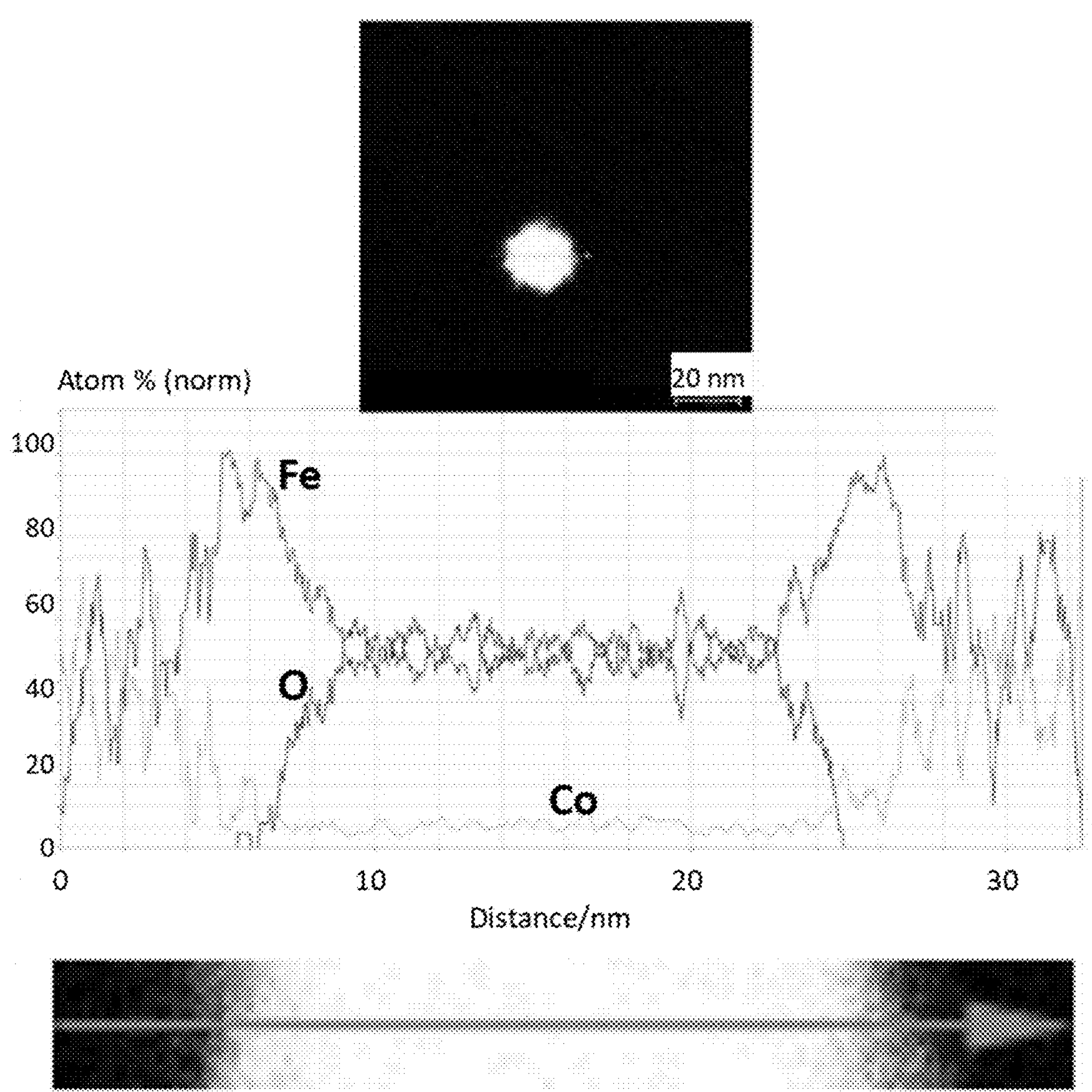
FIG. 48 is an energy-dispersive X-ray spectroscopy line scan of the distribution of Cobalt, iron and oxygen through the synthesized 21 nm (2st layer) Co-IONPs under low nitrogen flow.
Figure 49:
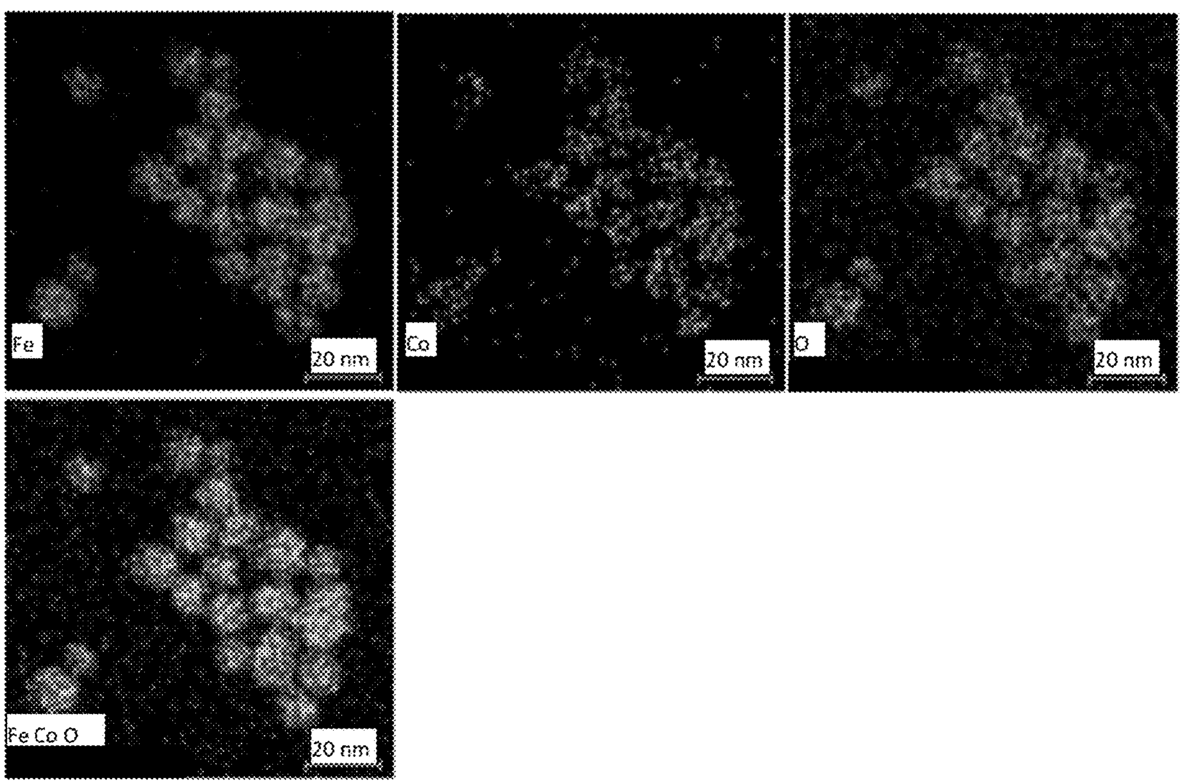
FIG. 49 is an energy-dispersive X-ray spectroscopy of 14 nm ($1^{st}$ layer) Co-IONPs under low nitrogen flow.
Figure 49:
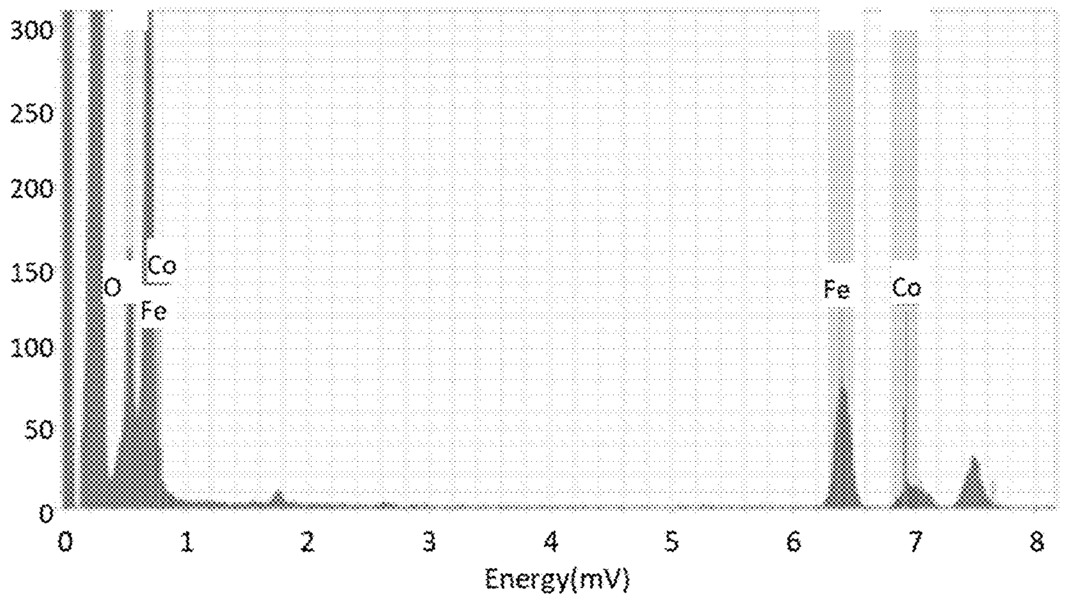
Figure 50:
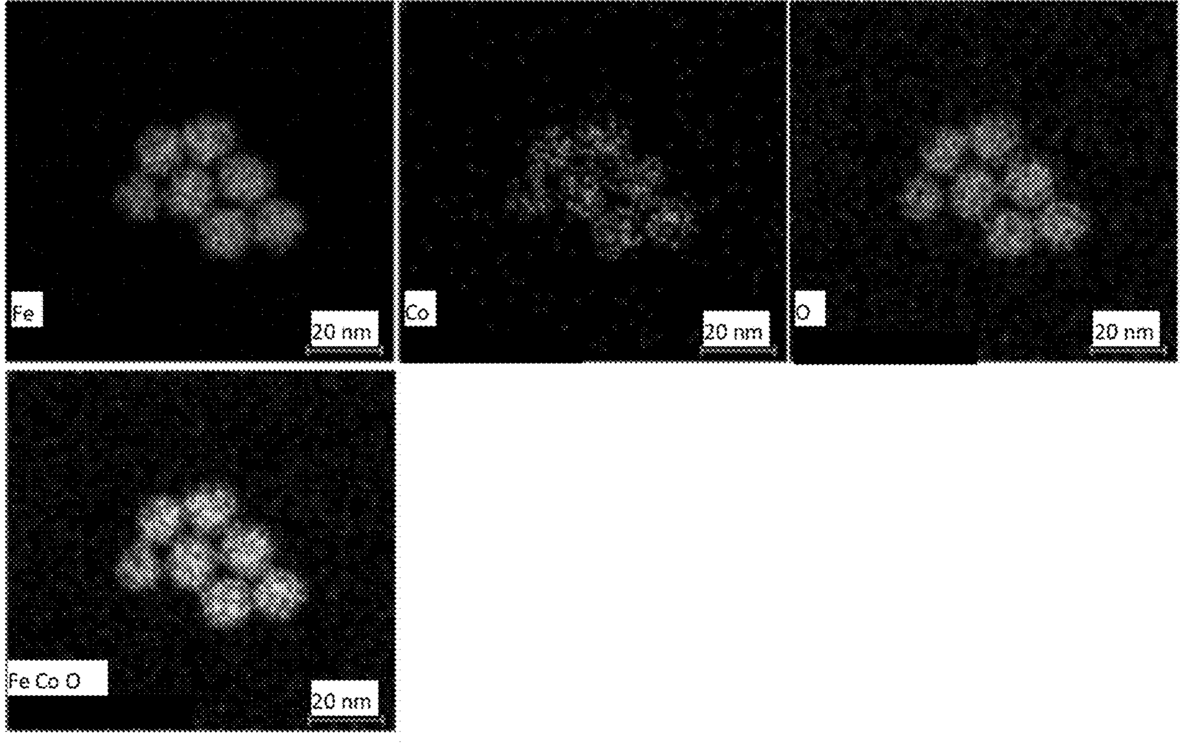
FIG. 50 is an energy-dispersive X-ray spectroscopy of 21 nm ($2^{st}$ layer) Co-IONPs under low nitrogen flow.
Figure 50:
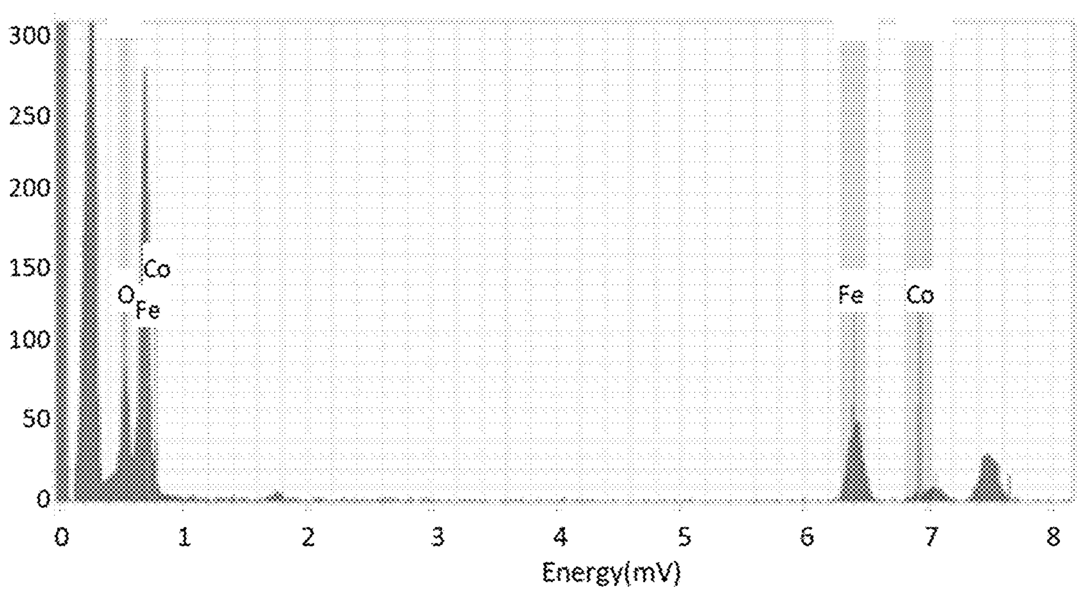

In order to enhance the heating performance and magnetic properties of the disclosed Co-IONP, seed-mediated growth method was used to increase size of nanoparticles from 14 nm to 21 nm (FIG. 45). I-FFT of the newly synthesized 21 nm Co-IONPs showed no observable crystalline defects (FIG. 46). The EDX (energy dispersive x-ray spectroscopy) spectrum of both 14 nm ($1^{st}$ layer) and 21 nm (2nd layer) Co-IONPs revealed the presence of Fe, Co, and O distributed across the magnetic nanoparticles (FIGS. 47 and 48). The amount of cobalt in both nanoparticles was rather minimal and consistent throughout the nanoparticle as shown in the figures. However, for 14 nm Co-IONPs, oxygen and iron concentrations were found to be highest at the nanoparticle's core and gradually drop as the particle approached its outer shell. The shell of 21 nm Co-IONP, on the other hand, was clearly dominated by iron, which decreased as it approached the core. However, the oxygen distribution in the 21 nm particle followed the same pattern as the 14 nm particle in the first layer. Furthermore, EDX spectroscopy analysis of multiple nanoparticles confirmed that 14 nm Co-IONPs contains 3.7% Co, 32.3% Fe and 64% O and 21 nm Co-IONPs contains 2.87% Co, 44.45% Fe and 52.68% O (FIGS. 49 and 50).

Figure 53:
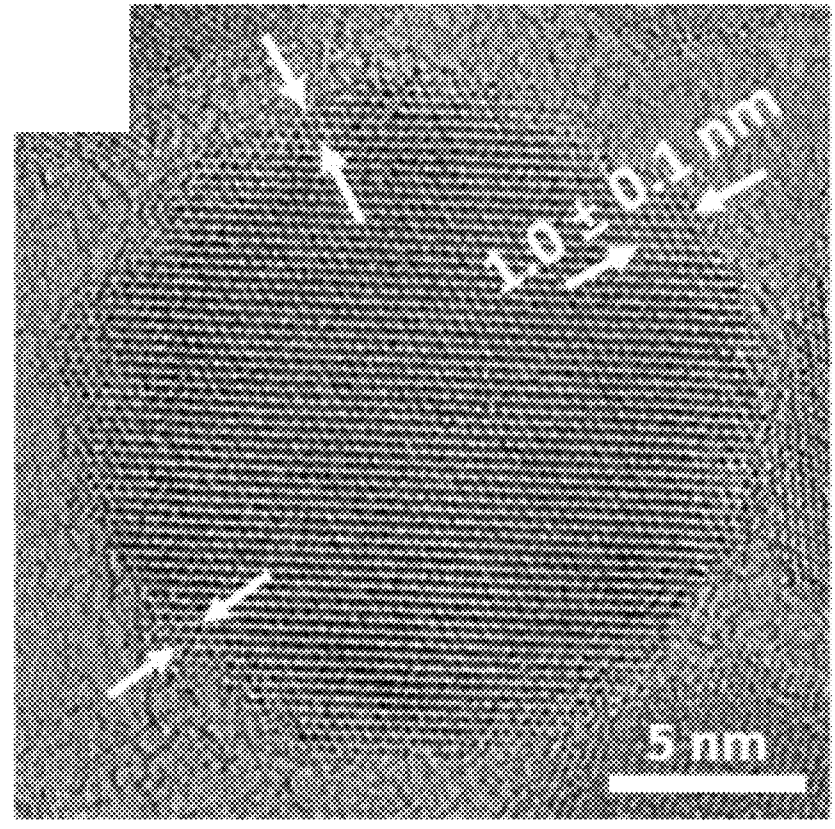
FIG. 53 is a high-resolution TEM image of a Co-doped iron ozide nanoparticle synthesized at a 50 mL/min nitrogen flow rate, with the shell of the nanoparticle indicated by the white arrows.
Figure 54:
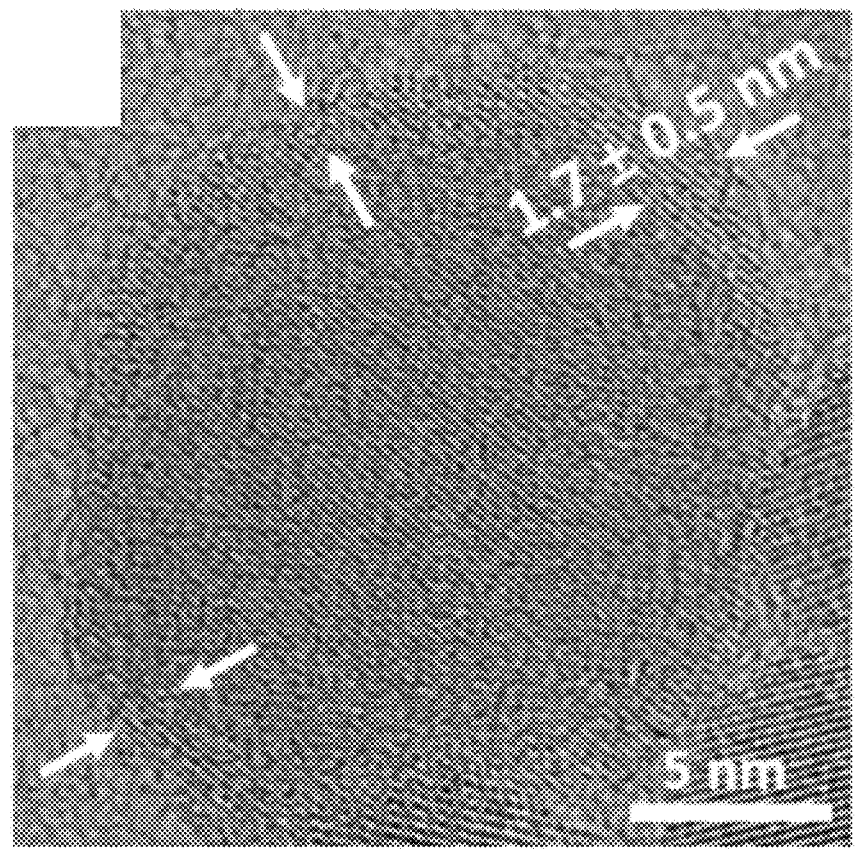
FIG. 54 is a high-resolution TEM image of a Co-doped iron ozide nanoparticle synthesized at a 10 mL/min nitrogen flow rate, with the shell of the nanoparticle indicated by the white arrows.
Figure 55:
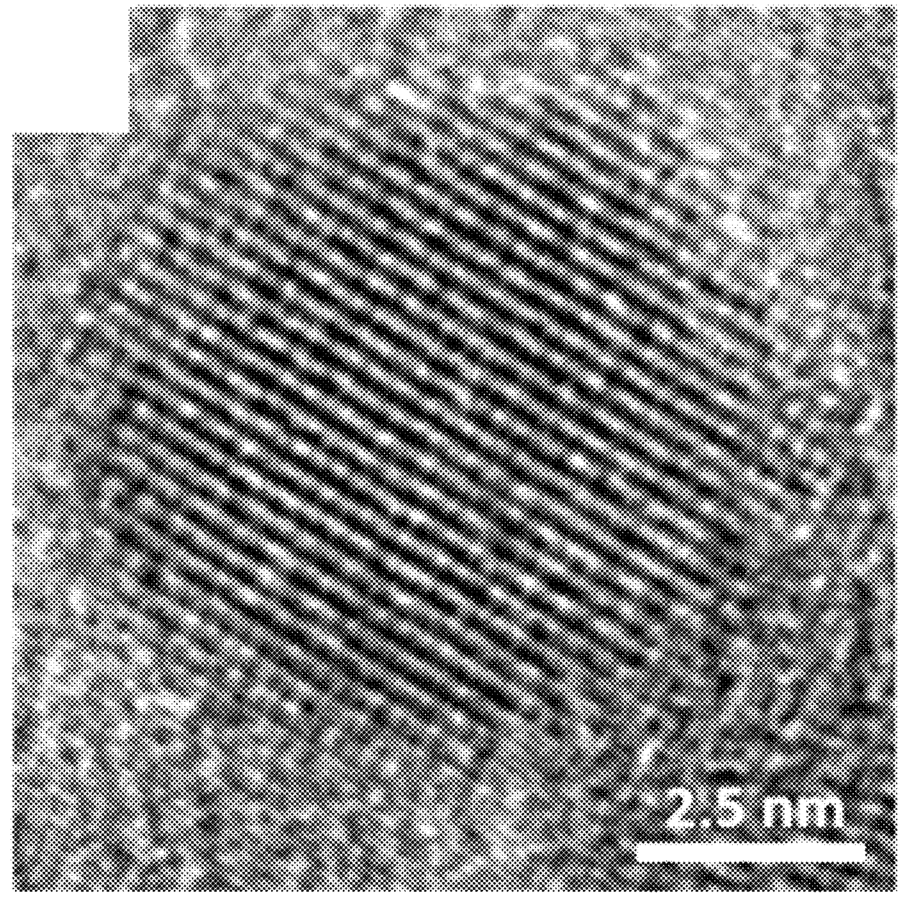
FIG. 55 is a high-resolution TEM image of a Co-doped iron ozide nanoparticle synthesized at a 4000 mL/min nitrogen flow rate, and illustrating the absence of a shell on the nanoparticle.

Because of the compositional changes between the core and the outer surface of the nanoparticles, they may be considered core/shell nanoparticles. For example, the 14 nm nanoparticles may be described as a cobalt-doped $Fe_3O_4/\gamma$-$Fe_2O_3$ core/shell nanoparticles (e.g., having a formula Co—$Fe_3O_4/\gamma$-$Fe_2O_3$ where the cobalt is distributed throughout the nanoparticle including the shell). In some embodiments, nanoparticles that are prepared with low nitrogen flow rates, such as below 400 mL/min (for example, 50 mL/min or lower) demonstrated a core/shell structure, as shown by FIGS. 53 and 54. However, at higher flow rates, such as 400 mL/min and above, the nanoparticles did not show a core/shell structure (FIG. 55) and tended to be of a smaller size (10 nm or less).

Figure 51:
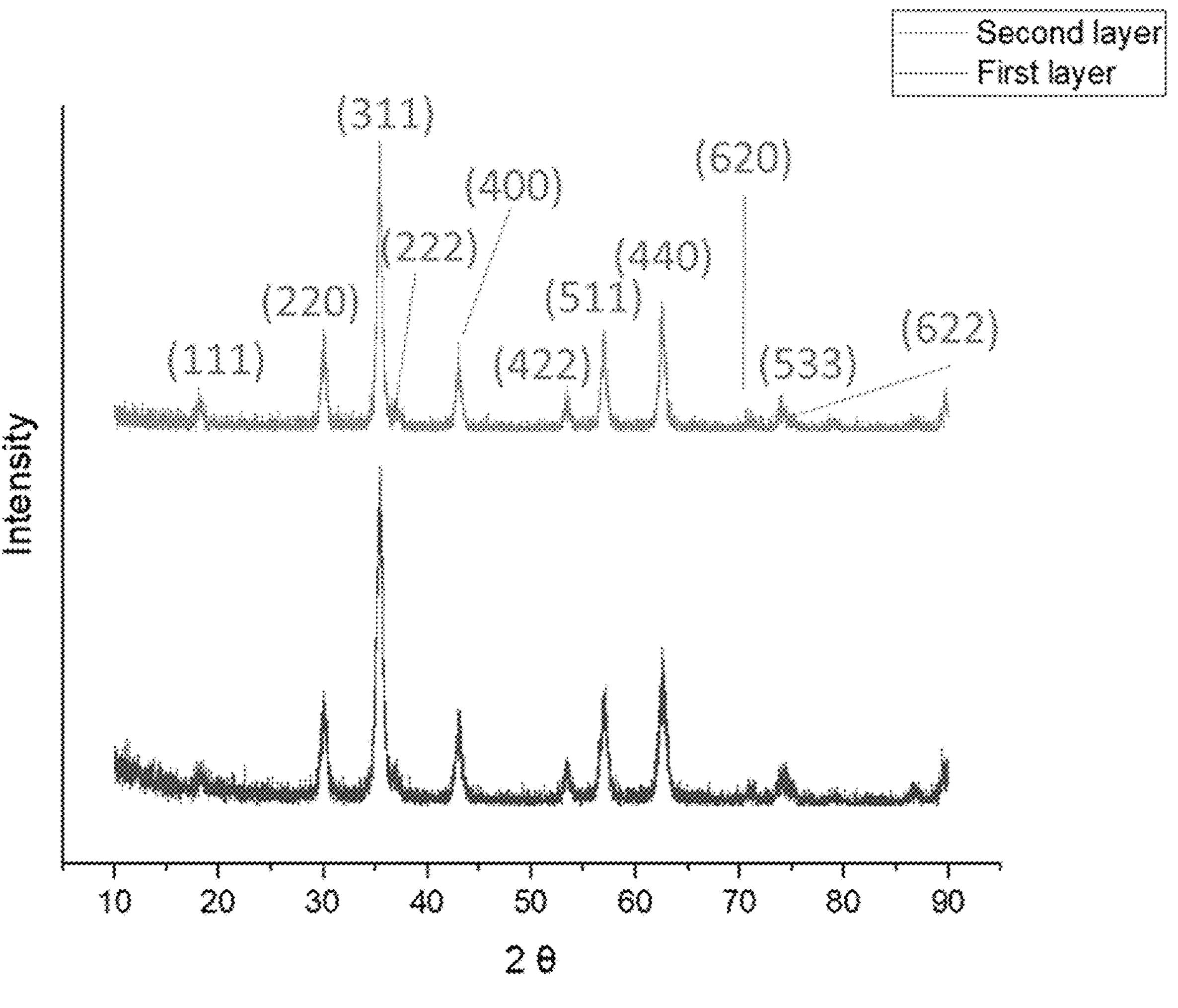
FIG. 51 is an X-ray diffractogram of the Co-IONPs synthesized under low nitrogen flow, with the lower graph (grey) corresponding to the $1^{st}$ layer and the upper graph (red) corresponding to the 2nd layer.

X-ray diffraction (XRD) pattern was recorded for $1^{st}$ layer 14 nm and $2^{nd}$ layer 21 nm Co-IONPs (FIG. 51). It can be clearly seen from the diffraction pattern that synthesized nanoparticles have all peaks corresponding to cobalt doped iron oxide nanoparticles with high consistency with ICDD No. 221086.

Conclusions

Nanoparticle Size Increased with Decreased Inert Gas Flow Rate

Cobalt doped nanoparticles were prepared using four different amounts of nitrogen input during synthesis (900, 400, 50, and 10 ml/min), in which the least nitrogen input allows for increased oxygen presence in the system than the highest nitrogen input. Based on TEM imaging, the average diameter of Co-IONPs synthesized at 900, 400, 50, and 10 ml/min of $N_2$ flow rate was 4.8±1.3 nm, 10±1.5 nm, 13.8±1.4 nm, and 14.4±3.8 nm respectively with an overall irregular hexagonal shape. These results demonstrates that the precise size of iron oxide nanoparticles was controlled through the regulated introduction of inert gas flow into the thermal decomposition reaction. Lower nitrogen flow rate results in higher nanoparticle sizes in both doped and undoped iron oxide nanoparticles.

Crystalline Defects Decrease with Decreased Flow Rate

Co-IONPs synthesized in higher nitrogen flow rates (such as 400 ml/min and 900 ml/min) were shown to poses evident lattice fringe defects in inverse Fourier transform (I-FFT) studies. The defect concentration in 900 ml/min $N_2$ flow rate was observably higher than that of 400 ml/min $N_2$ flow as indicated in the images. On the other hand, nanoparticles synthesized under 50 ml/min and 10 ml/min $N_2$ flow rates did not have any observable crystal lattice defects in I-FFT studies.

Heating Performance Increase with Decreased Nitrogen Flow Rate

The specific absorption rate of Co-IONPs synthesized at 900, 400, 50, and 10 mL/min of $N_2$ flow rate was 75.8, 1165, 4535, and 9412.9 W/g respectively. As the nitrogen flow rate decreased, the SAR increased. Without being bound to a particular theory the increased SAR might be due, at least in part, to the increase in size with the lower nitrogen flow.

Saturation Magnetization Increase with Decreased Nitrogen Flow Rate

The saturation magnetization of Co-IONPs synthesized at 900, 400, and 50 mL/min of $N_2$ flow rate was 18.7, 50.4, and 53 $Am^2/Kg$ respectively. Therefore lower nitrogen input resulted in higher saturation magnetization.

Seeded Mediated Nanoparticle Growth from 14 to 21 nm Under Lowest Nitrogen Input of 10 mL/Min and the Elemental Distribution Analysis Using EDX In order to enhance the heating performance of Co-IONPs synthesized at a low nitrogen flow rate, a seed-mediated growth method was used to increase the size of nanoparticles from 14 nm to 21 nm. The EDX (energy dispersive x-ray spectroscopy) spectrum of both 14 nm ($1^{st}$ layer) and 21 nm ($2^{nd}$ layer) Co-IONPs revealed the presence of Fe, Co, and O distributed across the magnetic nanoparticles. The amount of cobalt in both nanoparticles was rather minimal and consistent throughout the nanoparticle. However, for 14 nm Co-IONPs, oxygen, and iron concentrations were found to be highest at the nanoparticle's core and gradually drop as the particle approached its outer shell. The shell of 21 nm Co-IONP, on the other hand, was clearly dominated by iron, which decreased as it approached the core. However, the oxygen distribution in the 21 nm particle followed the same pattern as the 14 nm particle in the first layer. Furthermore, EDX spectroscopy analysis of nanoparticles confirmed that 14 nm Co-IONPs contains 3.7% Co, 32.3% Fe and 64% O and 21 nm Co-IONPs contains 2.87% Co, 44.45% Fe and 52.68% O.

IX. Exemplary Embodiments

The following numbered paragraphs illustrate exemplary embodiments of the disclosed technology.

Paragraph 1. A nanoparticle, comprising from greater than zero to 5 atom % cobalt, from 18 atom % to 60 atom % iron, and from greater than 35 atom % to 82 atom % oxygen, in amounts relative to each other, such that the total amount of cobalt, iron and oxygen is 100 atom %; and wherein the nanoparticle has a non-spherical shape.

Paragraph 2. The nanoparticle of paragraph 1, wherein the nanoparticle is substantially free of crystalline defects.

Paragraph 3. The nanoparticle of paragraph 1 or paragraph 2, wherein the nanoparticle has a specific absorption rate of from 2500 W $g^{-1}$ to 15000 W $g^{-1}$.

Paragraph 4. The nanoparticle of any one of paragraphs 1-3, wherein the nanoparticle has a size of from 4 nm to less than 50 nm.

Paragraph 5. The nanoparticle of paragraph 4, wherein the nanoparticle has a size of from 10 nm to 50 nm.

Paragraph 6. The nanoparticle of paragraph 4, wherein the nanoparticle has a size of from 14 nm to 30 nm.

Paragraph 7. The nanoparticle of any one of paragraphs 1-6, wherein the nanoparticle comprises from 1 atom % to 5 atom % cobalt.

Paragraph 8. The nanoparticle of any one of paragraphs 1-7, wherein the nanoparticle comprises from 1 atom % to 3 atom % cobalt.

Paragraph 9. The nanoparticle of any one of paragraphs 1-8, wherein the nanoparticle comprises from 18 atom % to 45 atom % iron.

Paragraph 10. The nanoparticle of any one of paragraphs 1-9, wherein the nanoparticle comprises from 35 atom % to 80 atom % oxygen.

Paragraph 11. The nanoparticle of any one of paragraphs 1-10, wherein the nanoparticle comprises from 2 atom % to 4 atom % cobalt, from 30 atom % to 45 atom % iron, and from 51 atom % to 65 atom % oxygen.

Paragraph 12. The nanoparticle of any one of paragraphs 1-10, wherein the nanoparticle comprises from 2 atom % to 4 atom % cobalt, from 18 atom % to 25 atom % iron, and from 60 atom % to 80 atom % oxygen.

Paragraph 13. The nanoparticle of any one of paragraphs 1-12, wherein the nanoparticle has an irregular hexagon shape, and the size is measured as the longest distance between two opposite vertices.

Paragraph 14. The nanoparticle of paragraph 1, wherein the nanoparticle is substantially defect free, comprises from 2 atom % to 4 atom % cobalt, from 30 atom % to 35 atom % iron and sufficient oxygen to make a total amount of cobalt, iron and oxygen is 100 atom %, and has a size of 14 nm.

Paragraph 15. The nanoparticle of paragraph 1, wherein the nanoparticle is substantially defect free, comprises from 2 atom % to 4 atom % cobalt, from 40 atom % to 50 atom % iron and sufficient oxygen to make a total amount of cobalt, iron and oxygen is 100 atom %, and has a size of 21 nm.

Paragraph 16. A method of making the nanoparticle of any one of paragraphs 1-15, the method comprising:

combine a first cobalt compound and a first iron compound in a first solvent system to form a first mixture;

heat the first mixture to a first temperature under a first nitrogen flow;

cool the first mixture to room temperature and precipitate a solid intermediate;

heat the solid intermediate with a second cobalt compound and a second iron compound in a second solvent system to a second temperature and under a second nitrogen flow;

cool and isolate the nanoparticle.

Paragraph 17. The method of paragraph 17, wherein the first cobalt compound and the second cobalt compound independently is selected from cobalt (II) chloride ($CoCl_2$), cobalt (II) chloride hexahydrate ($CoCl_2$ $6H_2O$), cobalt (II) sulphate ($CoSO_4$), cobalt (II) sulphate heptahydrate ($CoSO_4$ $7H_2O$), cobalt (II) nitrate hexahydrate ($Co(NO_3)_2$ $6H_2O$), cobalt (II) carbonate ($CoCO_3$), or a combination thereof.

Paragraph 18. The method of paragraph 17, wherein the first cobalt compound and the second cobalt compound are the same.

Paragraph 19. The method of paragraph 17, wherein the first cobalt compound and the second cobalt compound are both cobalt (II) chloride hexahydrate.

Paragraph 20. The method of any one of paragraphs 16-19, wherein the first iron compound and the second iron compound independently is selected from (Zero-valent) $Fe(CO)_5$, iron (III) acetylacetonate ($Fe(acac)_3$), iron (II) sulfate (ferrous sulfate, $FeSO_4$), iron (II) chloride ($FeCl_2$, ferrous chloride), iron (III) nitrate ($Fe(NO_3)_3$, ferric nitrate), iron (III) sulfate ($Fe(SO_4)_3$, ferric sulfate), iron (III) chloride ($FeCl_3$, ferric chloride), or a combination thereof.

Paragraph 21. The method of paragraph 20, wherein the first iron compound and the second iron compound are the same.

Paragraph 22. The method of paragraph 21, wherein the first iron compound and the second iron compound are both iron (III) acetylacetone.

Paragraph 23. The method of any one of paragraphs 16-22, wherein the first solvent system and the second solvent system independently comprise a solvent selected from trioctylamine, docosane, n-octylether, benzyl ether, or a combination thereof.

Paragraph 24. The method of any one of paragraphs 16-23, wherein the first solvent system and the second solvent system independently comprise a surfactant selected from oleic acid, oleylamine, 1-octadecane, or a combination thereof.

Paragraph 25. The method of any one of paragraphs 16-24, wherein the first solvent system and the second solvent system are the same.

Paragraph 26. The method of any one of paragraphs 16-25, wherein the first solvent system and the second solvent system are both oleic acid, oleylamine and n-octyl ether.

Paragraph 27. The method of any one of paragraphs 16-26, wherein each of the first temperature and the second temperature independently is from 180° C. to 900° C.

Paragraph 28. The method of paragraph 27, wherein each of the first temperature and the second temperature independently is from 180° C. to 500° C.

Paragraph 29. The method of paragraph 27, wherein each of the first temperature and the second temperature independently is from 250° C. to 400° C.

Paragraph 30. The method of paragraph 27, wherein the first temperature and the second temperature both are 300° C.

Paragraph 31. The method of any one of paragraphs 16-30, wherein each of the first nitrogen flow and the second nitrogen flow independently is from greater than zero to 900 mL/min nitrogen.

Paragraph 32. The method of paragraph 31, wherein each of the first nitrogen flow and the second nitrogen flow independently is from 1 mL/min to 400 mL/min nitrogen.

Paragraph 33. The method of paragraph 31, wherein each of the first nitrogen flow and the second nitrogen flow independently is from 1 mL/min to 100 mL/min nitrogen.

Paragraph 34. The method of paragraph 31, wherein each of the first nitrogen flow and the second nitrogen flow independently is from 10 mL/min to 50 mL/min.

Paragraph 35. A composition comprising a nanoparticle according to any one of paragraphs 1-15, and a polymer.

Paragraph 36. The composition of paragraph 35, wherein the nanoparticle is encapsulated in the polymer.

Paragraph 37. The composition of paragraph 35 or paragraph 36, wherein the polymer is selected from polyethylene glycol-block-polycaprolactone (PEG-b-PCL), methoxy polyethylene glycol-block-polycaprolactone (mPEG-b-PCL), polyethylene glycol-block-polyvalerolactone (PEG-b-PVL), polyethylene glycol-block-polylactic acid (PEG-b-PLA) or polyethylene glycol-block-poly(lactic acid-co-glycolic acid) (PEG-b-PLGA).

Paragraph 38. The composition of paragraph 37, wherein the polymer comprises a PEG moiety.

Paragraph 39. The composition of paragraph 38, wherein the polymer is a PEG-PCL polymer.

Paragraph 40. The composition of any one of paragraphs 35-39, wherein the polymer has a molecular weight of from 10,000 Da to 20,000 Da.

Paragraph 41. The composition of any one of paragraphs 35-40, wherein the polymer has a molecular weight of from 13,000 Da to 17,000 Da.

Paragraph 42. The composition of any one of paragraphs 35-41, wherein the polymer has a molecular weight of about 15,000 Da.

Paragraph 43. The composition of any one of paragraphs 35-42, wherein the composition further comprises a targeting moiety conjugated to the polymer.

Paragraph 44. The composition of paragraph 43, wherein the targeting moiety is selected from a peptide, protein, small molecule, nucleic acid sequence, antibody, or a combination thereof.

Paragraph 45. The composition of paragraph 43 or paragraph 44, wherein the targeting moiety is an EGFR (Epidermal growth factor receptor), Integrin $\alpha v\beta 6$, Neuropilin-1, PD-L1, a HER2 receptor, or a combination thereof.

Paragraph 46. The composition of paragraph 43 or paragraph 44, wherein the targeting moiety is a targeting moiety for ovarian cancer.

Paragraph 47. The composition of paragraph 46, wherein the targeting moiety is a LHRH peptide, $\alpha$-3 integrin receptor, ROR1 (Receptor tyrosine kinase-like orphan receptor1), HE4 (Human epididymis protein 4), 5-Protein signature (OVA1), or a combination thereof.

Paragraph 48. The composition of paragraph 43 or paragraph 44, wherein the targeting moiety is a targeting moiety for endometriosis.

Paragraph 49. The composition of paragraph 48, wherein the targeting moiety is CD44, EphB4, CXCL13, CTLA4, CD10, vascular endothelial growth factor receptor 2 (KDR) or a combination thereof.

Paragraph 50. The composition of paragraph 48, wherein the targeting moiety is a KDR targeting peptide.

Paragraph 51. A method, comprising:

forming a solution or suspension comprising a nanoparticle of any one of paragraphs 1-15 and a first organic solvent;

forming a mixture comprising the solution or suspension and a polymer in a second organic solvent; and isolating a composition comprising the nanoparticle and the polymer.

Paragraph 52. The method of paragraph 51, wherein the composition is a composition according to any one of paragraphs 35-42.

Paragraph 53. The method of paragraph 51, wherein the polymer comprises a targeting moiety.

Paragraph 54. The method of paragraph 53, wherein the composition is a composition according to any one of paragraphs 43-50.

Paragraph 55. The method of any one of paragraphs 51-54, wherein the first and second organic solvents are the same solvent.

Paragraph 56. The method of any one of paragraphs 51-55, wherein isolating the composition comprises adding water and evaporating the first and second organic solvents.

Paragraph 57. The method of any one of paragraphs 51-56, wherein isolating the composition comprises separating the composition from any non-encapsulated nanoparticles and any non-soluble polymer molecules.

Paragraph 58. A method, comprising administering the nanoparticle of any one of paragraphs 1-15, or the composition of any one of paragraphs 35-50, to a subject in need thereof.

Paragraph 59. The method of paragraph 58, wherein the method is a method of treating cancer.

Paragraph 60. The method of paragraph 59, wherein the cancer is ovarian cancer.

Paragraph 61. The method of paragraph 60, wherein the method is a method of treating non-cancerous lesions.

Paragraph 62. The method of paragraph 58, wherein the method is a method of treating endometriosis.

Paragraph 63. The method of any one of paragraphs 58-62, wherein the method is a method hyperthermia treatment method.

Paragraph 64. The method of any one of paragraphs 58-63, wherein administering comprises injecting the nanoparticle or the composition.

Paragraph 65. The method of paragraph 64, wherein the nanoparticle or the composition is injected systemically.

Paragraph 66. The method of paragraph 64, wherein the nanoparticle or the composition is injected locally.

Paragraph 67. The method of any one of paragraphs 58-66, wherein the method further comprises applying an alternating magnetic field to the nanoparticle or composition.

Paragraph 68. The method of paragraph 67, wherein the alternating magnetic field has:

a field strength of from 1 kA/m to 100 kA/m;

a frequency of from 50 kHz to 900 kHz; or a combination thereof.

Paragraph 69. The method of any one of paragraphs 58-68, wherein the nanoparticle or composition is administered in an amount sufficient to provide from 1 mg to 100 mgs of iron per kg weight of the subject.

Paragraph 70. The method of paragraph 69, wherein the amount administered is sufficient to provide from 1 mg to 50 mgs of iron per kg weight of the subject.

Paragraph 71. The method of paragraph 70, wherein the amount administered is sufficient to provide from 1 mg to 10 mgs of iron per kg weight of the subject.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A composition comprising:

a polymer; and a non-spherical nanoparticle comprising from greater than zero to 5 atom % cobalt, from 18 atom % to 60 atom % iron, and from greater than 35 atom % to 82 atom % oxygen, in amounts relative to each other, such that the total amount of cobalt, iron and oxygen is 100 atom %; wherein the nanoparticle has a specific absorption rate of from 2,500 W $g^{-1}$ to 20,000 W $g^{-1}$.

2. The composition of claim 1, wherein:

the nanoparticle has no observable crystalline defects under high resolution TEM;

the nanoparticle has a size of from 4 nm to less than 50 nm;

or a combination thereof.

3. The composition of claim 1, wherein the nanoparticles comprises:

from 1 atom % to 5 atom % cobalt;

from 18 atom % to 45 atom % iron;

from 35 atom % to 80 atom % oxygen;

or a combination thereof.

4. The composition of claim 1, wherein the nanoparticle has a size of from 14 nm to 30 nm.

5. The composition of claim 1, wherein the nanoparticle comprises from 2 atom % to 4 atom % cobalt, from 30 atom % to 45 atom % iron, and from 51 atom % to 65 atom % oxygen.

6. The composition of claim 1, wherein the nanoparticle is encapsulated in the polymer.

7. The composition of claim 1, wherein the polymer is selected from polyethylene glycol-block-polycaprolactone (PEG-b-PCL), methoxy polyethylene glycol-block-polycaprolactone (mPEG-b-PCL), polyethylene glycol-block-polyvalerolactone (PEG-b-PVL), polyethylene glycol-block-polylactic acid (PEG-b-PLA) or polyethylene glycol-block-poly(lactic acid-co-glycolic acid) (PEG-b-PLGA).

8. The composition of claim 1, wherein the polymer is a PEG-PCL polymer.

9. The composition of claim 1, wherein the polymer has a molecular weight of from 10,000 Da to 20,000 Da.

10. The composition of claim 1, wherein the polymer has a molecular weight of about 15,000 Da.

11. The composition of claim 1, wherein the composition further comprises a targeting moiety conjugated to the polymer.

12. The composition of claim 11, wherein the targeting moiety is selected from a peptide, protein, small molecule, nucleic acid sequence, antibody, or a combination thereof.

13. The composition of claim 11, wherein the targeting moiety is a targeting moiety for ovarian cancer or endometriosis.

14. The composition of claim 11, wherein the targeting moiety is an EGFR (Epidermal growth factor receptor), Integrin αvβ6, Neuropilin-1, PD-L1, a HER2 receptor, a LHRH peptide, α-3 integrin receptor, ROR1 (Receptor tyrosine kinase-like orphan receptor1), HE4 (Human epididymis protein 4), 5-Protein signature (OVA1), CD44, EphB4, CXCL13, CTLA4, CD10, vascular endothelial growth factor receptor 2 (KDR), or a combination thereof.

15. The composition of claim 11, wherein the targeting moiety is a targeting moiety for ovarian cancer and is selected from a LHRH peptide, α-3 integrin receptor, ROR1 (Receptor tyrosine kinase-like orphan receptor1), HE4 (Human epididymis protein 4), 5-Protein signature (OVA1), or a combination thereof.

16. The composition of claim 11, wherein the targeting moiety is a targeting moiety for endometriosis and is selected from CD44, EphB4, CXCL13, CTLA4, CD10, vascular endothelial growth factor receptor 2 (KDR) or a combination thereof.

17. The composition of claim 1, the composition comprising:

a nanoparticle comprising from 1 atom % to 5 atom % cobalt, from 18 atom % to 45 atom % iron, and from 35 atom % to 80 atom % oxygen, such that a total amount of cobalt, iron and oxygen in the nanoparticle is 100%, the nanoparticle having a size of from 4 nm to less than 50 nm, a specific absorption rate of from 2,500 W $g^{-1}$ to 20,000 W $g^{-1}$, and no observable crystalline defects under high resolution TEM;

a PEG-PCL polymer encapsulating the nanoparticle, the polymer having a molecular weight of from 13,000 Da to 17,000 Da; and a targeting moiety for ovarian cancer or endometriosis conjugated to the polymer.

18. A non-spherical nanoparticle comprising from 1 atom % to 5 atom % cobalt, from 18 atom % to 45 atom % iron, and from 35 atom % to 80 atom % oxygen, such that a total amount of cobalt, iron and oxygen in the nanoparticle is 100%, the nanoparticle having a size of from 4 nm to less than 50 nm, a specific absorption rate of from 2,500 W $g^{-1}$ to 20,000 W $g^{-1}$, and no observable crystalline defects under high resolution TEM.

19. A method, comprising:

forming a solution or suspension comprising a first organic solvent and a non-spherical nanoparticle having a specific absorption rate of from 2,500 W $g^{-1}$ to 20,000 W $g^{-1}$, the non-spherical nanoparticle comprising from greater than zero to 5 atom % cobalt, from 18 atom % to 60 atom % iron, and from greater than 35 atom % to 82 atom % oxygen, in amounts relative to each other, such that the total amount of cobalt, iron and oxygen is 100 atom %;

forming a mixture comprising the solution or suspension and a polymer in a second organic solvent; and isolating a composition comprising the non-spherical nanoparticle and the polymer.

20. A method, comprising administering the composition of claim 1, to a subject in need of hyperthermia treatment, and applying an alternating magnetic field to the composition.

* * * * *

SEQUENCE LISTING

```
Sequence total quantity: 6
SEQ ID NO: 1            moltype = AA  length = 9
FEATURE                 Location/Qualifiers
REGION                  1..9
                        note = Synthetic peptide
source                  1..9
                        mol_type = protein
                        organism = synthetic construct
VARIANT                 6
                        note = X is D-Lysine or D-Cysteine
SEQUENCE: 1
QHWSYXLRP                                                       9

SEQ ID NO: 2            moltype = AA  length = 10
FEATURE                 Location/Qualifiers
REGION                  1..10
                        note = Synthetic peptide
SITE                    1
                        note = X is Pyroglutamic acid (Glp)
SITE                    6
                        note = X is D-Lysine
source                  1..10
                        mol_type = protein
                        organism = synthetic construct
SEQUENCE: 2
XHWSYXLRPG                                                      10

SEQ ID NO: 3            moltype = AA  length = 10
FEATURE                 Location/Qualifiers
REGION                  1..10
                        note = Synthetic peptide
SITE                    1
                        note = X is Pyroglutamic acid (Glp)
source                  1..10
                        mol_type = protein
                        organism = synthetic construct
SEQUENCE: 3
XHWSHDWKPG                                                      10
```

-continued

```
SEQ ID NO: 4            moltype = AA  length = 7
FEATURE                 Location/Qualifiers
REGION                  1..7
                        note = Synthetic peptide
source                  1..7
                        mol_type = protein
                        organism = synthetic construct
SEQUENCE: 4
ATWLPPR                                                     7

SEQ ID NO: 5            moltype = AA  length = 6
FEATURE                 Location/Qualifiers
REGION                  1..6
                        note = Synthetic peptide
source                  1..6
                        mol_type = protein
                        organism = synthetic construct
SEQUENCE: 5
DGWGPN                                                      6

SEQ ID NO: 6            moltype = AA  length = 21
FEATURE                 Location/Qualifiers
REGION                  1..21
                        note = Synthetic peptide
source                  1..21
                        mol_type = protein
                        organism = synthetic construct
SEQUENCE: 6
VATNGKEVVS STGVLFVKFG P                                     21
```